United States Patent
Becker et al.

(10) Patent No.: US 11,103,613 B2
(45) Date of Patent: Aug. 31, 2021

(54) PHOSPHORYLATED POLY (ESTER-UREA) BASED DEGRADABLE BONE ADHESIVES

(71) Applicant: THE UNIVERSITY OF AKRON, Akron, OH (US)

(72) Inventors: Matthew Becker, Chapel Hill, NC (US); Vrushali Dinkar Bhagat, Cuyahoga Falls, OH (US)

(73) Assignee: The University of Akron, Akron, OH (US)

( * ) Notice: Subject to any disclaimer, the term of this patent is extended or adjusted under 35 U.S.C. 154(b) by 15 days.

(21) Appl. No.: 16/095,718

(22) PCT Filed: Apr. 25, 2017

(86) PCT No.: PCT/US2017/029342
§ 371 (c)(1),
(2) Date: Oct. 23, 2018

(87) PCT Pub. No.: WO2017/189534
PCT Pub. Date: Nov. 2, 2017

(65) Prior Publication Data
US 2019/0167838 A1    Jun. 6, 2019

Related U.S. Application Data

(60) Provisional application No. 62/328,653, filed on Apr. 28, 2016.

(51) Int. Cl.
*A61L 24/04* (2006.01)
*C08L 75/02* (2006.01)
(Continued)

(52) U.S. Cl.
CPC ......... *A61L 24/0042* (2013.01); *A61L 24/046* (2013.01); *C08K 3/16* (2013.01);
(Continued)

(58) Field of Classification Search
None
See application file for complete search history.

(56) References Cited

U.S. PATENT DOCUMENTS

| 9,023,972 B2 | 5/2015 | Chu et al. |
| 2007/0128250 A1* | 6/2007 | Katsarava ............... C08L 75/02 424/426 |
| 2013/0071930 A1* | 3/2013 | Chu ........................ A61K 47/34 435/377 |

FOREIGN PATENT DOCUMENTS

| WO | 2015066173 A1 | 5/2015 |
| WO | 2015171854 A1 | 11/2015 |
| WO | 2016014471 A1 | 1/2016 |

OTHER PUBLICATIONS

Addison JB, Ashton NN, Weber WS, Stewart RJ, Holland GP, Yarger JL. β-Sheet nanocrystalline domains formed from phosphorylated serine-rich motifs in caddisfly larval silk: a solid state NMR and XRD study. Biomacromolecules. Apr. 8, 2013; 14(4): 1140-8. (Year: 2013).*

(Continued)

*Primary Examiner* — Nissa M Westerberg
(74) *Attorney, Agent, or Firm* — Renner, Kenner, Greive, Bobak Taylor & Weber

(57) ABSTRACT

In various aspects, the present invention provides a degradable and resorbable novel phosphate functionalized amino acid-based poly(ester urea) adhesive and related methods for its synthesis and use. These adhesives are formed from phosphate functionalized PEU polymers and copolymers crosslinked using one or more divalent metal crosslinking agents. The phosphate functionalized amino acid-based poly (ester urea) adhesives of various embodiments of the present invention have been found particularly effective in bonding bone to either bone or metal and have demonstrated adhesive strengths on bone samples that were significant and (Continued)

comparable to commercially available poly(methyl methacrylate) bone cement.

20 Claims, 28 Drawing Sheets

(51) Int. Cl.
*A61L 24/00* (2006.01)
*C08K 3/16* (2006.01)
*C08L 77/04* (2006.01)

(52) U.S. Cl.
CPC ............... *C08L 75/02* (2013.01); *C08L 77/04* (2013.01); *C08K 2003/162* (2013.01); *C08K 2003/166* (2013.01); *C08K 2003/168* (2013.01); *C08L 2203/02* (2013.01)

(56) References Cited

OTHER PUBLICATIONS

Bhagat, et al. Caddisfly Inspired Phosphorylated Poly (ester urea)-Based Degradable Bone Adhesives Biomacromolecules, vol. 17, Published Jul. 12, 2016, pp. 3016-3024 and Supporting Information, pp. 1-18.

* cited by examiner

Bone surface with an array of positive and negative charges

- P(pSer-co-Val)

• - Ca²⁺ as crosslinking agent

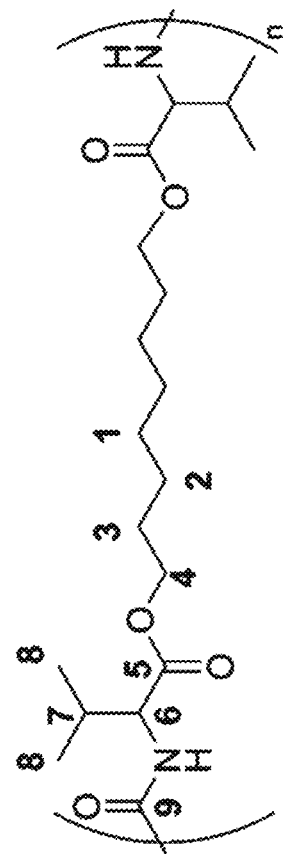
FIG. 23
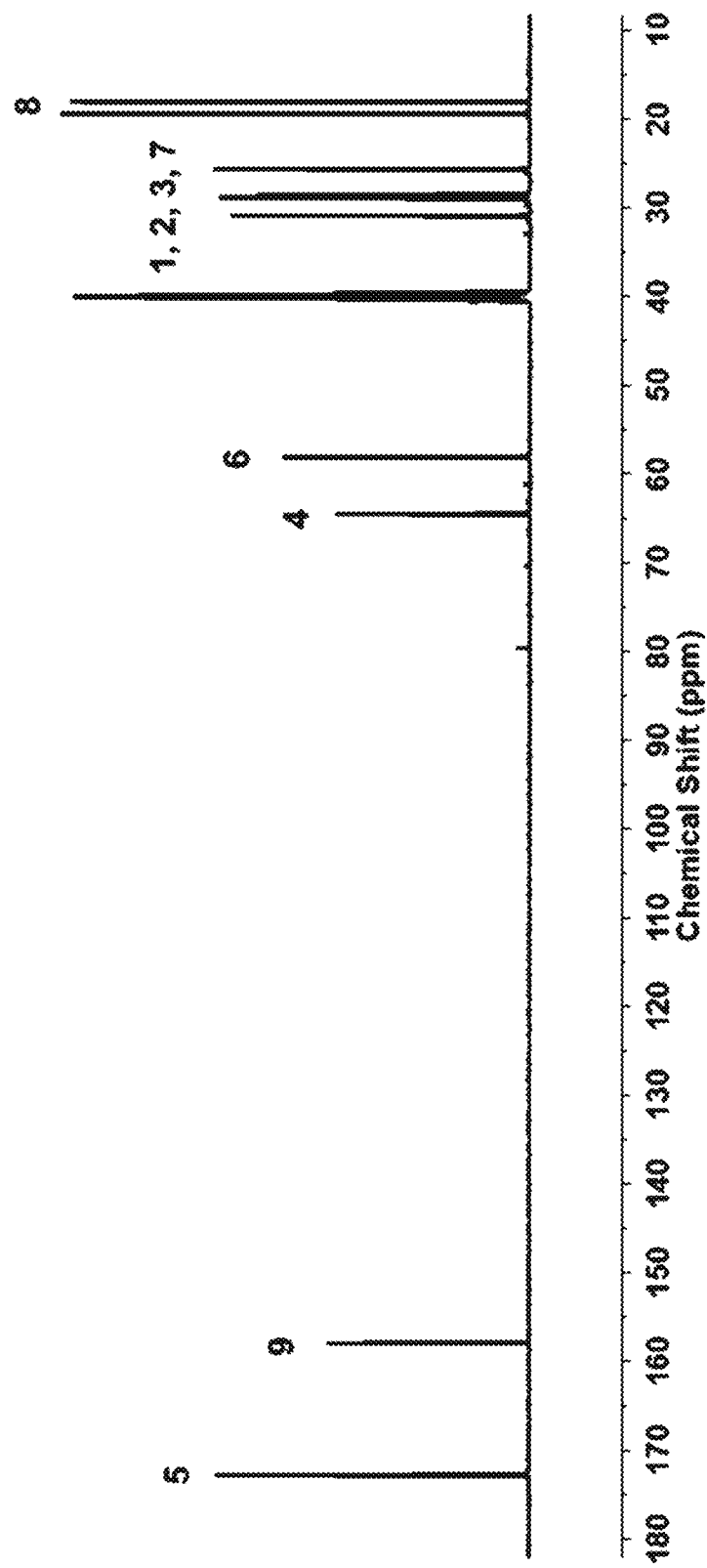

PHOSPHORYLATED POLY (ESTER-UREA) BASED DEGRADABLE BONE ADHESIVES

CROSS REFERENCE TO RELATED APPLICATIONS

This application claims the benefit of U.S. provisional patent application Ser. No. 62/328,653 entitled "Phosphorylated Poly(ester-urea) Based Degradable Bone Adhesives," filed Apr. 28, 2016, and incorporated herein by reference in its entirety.

STATEMENT REGARDING FEDERALLY SPONSORED RESEARCH OR DEVELOPMENT SUPPORT

This invention was made with government support under contract numbers DMR-1507420 and DMR-1359321 awarded by the National Science Foundation and contract number W81XWH-15-1-0718 from the Department of Defense Medical Research and Development Program, Combat Casualty Care. The government has certain rights in the invention

FIELD OF THE INVENTION

One or more embodiments of the present invention relates to degradable and resorbable medical and biological adhesives. In certain embodiments, the present invention relates to phosphorylated poly(ester-urea) (PEU) based to degradable and resorbable adhesives, particularly useful as bone adhesives.

BACKGROUND OF THE INVENTION

Bone and tissue adhesives are essential in surgeries for their assistance in wound healing, hemostasis, tissue reconstruction and drug delivery. Classical structural alternatives in bone surgeries include use of metallic plates, pins and screws as support medium. These options while safe and serviceable suffer from aseptic loosening, poor anchorage to the bone, cause irritation to the neighboring soft tissue, cause discomfort to the patient and need to be replaced or removed after the bone regeneration. Poly(methyl methacrylate) (PMMA) bone cement is also commonly used in bone surgeries but has significant drawbacks. In particular, PMMA bone cements are not adhesive in nature, lack chemical interaction, can cause significant heat generation and are prone to shrinkage. Attempts to use synthetic glues like cyanoacrylate, polyurethane, epoxy resin and calcium or magnesium phosphate ceramic bone cement as bone adhesives have failed either due to lack of interaction with the bone surface or poor strength. Alternative, bone adhesives with degradable properties and high adhesion strengths are currently an attractive clinical target.

Phosphate based compounds have been used as adhesion promoters for decades in underwater coatings, dental applications, bone implants, fillers and metal substrates. Several studies have demonstrated adhesion or bonding strength and osteoconductive potential of phosphate functionalized polymeric bone grafts showing significant improvement in bone bonding. Certain marine organisms like mussels, barnacles, starfish, sandcastle worms and caddisflies have evolved to synthesize their own underwater adhesive with strong bonding characteristics. Studies on caddisfly adhesive silk have confirmed the presence of phosphoserine (pSer) residues in the form of $(SX)_4$ motifs where S is serine and X is usually valine or isoleucine. Elemental analysis also showed the presence of divalent cations like $Ca^{2+}$ and $Mg^{2-}$ which undergo strong electrostatic interaction with the phosphate groups in pSer to impart strength to the fibers. The adhesive nature of caddisflies is attributed to the heavily phosphorylated regions in the adhesive filament.

Poly(ester urea)s (PEU)s are a class of polymers well suited for biomaterial applications because of their attractive properties including degradation into metabolic components, tunable mechanical properties, wide range of functionality and nontoxicity in vitro and in vivo. What is needed in the art is an adhesive for use with bone that has the adhesive properties seen in the caddisfly adhesive silk and the beneficial properties seen in PEU polymers.

SUMMARY OF THE INVENTION

In various aspects, the present invention provides a degradable and resorbable novel phosphate functionalized amino acid-based poly(ester urea) adhesive and related methods for its synthesis and use. These adhesives are formed from phosphate functionalized PEU polymers and copolymers crosslinked using one or more divalent metal crosslinking agents and were designed and created to mimic the properties of caddisfly adhesive silk. The phosphate functionalized amino acid-based poly(ester urea) adhesives of various embodiments of the present invention have been found particularly effective in bonding bone to either bone or metal and have demonstrated adhesive strengths on bone samples that were significant (439±203 KPa) and comparable to commercially available poly(methyl methacrylate) bone cement (530±133 KPa). It is believed that these phosphate functionalized PEU polymers and copolymers have significant potential as orthopaedic adhesives, scaffold materials for spinal cord injury and orthopaedic repairs in the presence of growth peptides like OGP or BMP-2 and are degradable in vitro and in vivo.

In a first aspect, the present invention is directed to a poly(ester urea) (PEU) based adhesive comprising: a PEU polymer backbone having one or more side chains comprising a phosphate group and a crosslinking agent comprising a divalent metal salt. In some embodiments, the PEU polymer chain comprises the residue of an amino acid selected from the group consisting of alanine (ala—A), glycine (gly—G), isoleucine (ile—I), leucine (leu—L), methionine (met—M), phenylalanine (phe—F), threonine (thr—T), tryptophan (trp—W), tyrosine (tyr—Y), or valine (val—V). In one or more embodiments, the poly(ester urea) (PEU) based adhesive of the present invention includes any one or more of the above referenced embodiments of the first aspect of the present invention wherein the PEU polymer chain comprises the residue of one or more phosphorylated L-serine molecules.

In one or more embodiments, the poly(ester urea) (PEU) based adhesive of the present invention includes any one or more of the above referenced embodiments of the first aspect of the present invention wherein the PEU polymer backbone having one or more side chains comprising a phosphate group further comprises: a residue of a first amino acid based polyester monomer comprising two phosphorylated amino acids separated by from 2 to 20 carbon atoms; and a residue of a second amino acid based polyester monomer comprising two amino acids separated by from 2 to 20 carbon atoms. In one or more embodiments, the poly(ester urea) (PEU) based adhesive of the present invention includes any one or more of the above referenced embodiments of the first aspect of the present invention wherein the first amino acid based polyester monomer comprises two phosphorylated L-serine molecules.

In one or more embodiments, the poly(ester urea) (PEU) based adhesive of the present invention includes any one or more of the above referenced embodiments of the first aspect of the present invention wherein the first amino acid based polyester monomer has the formula:

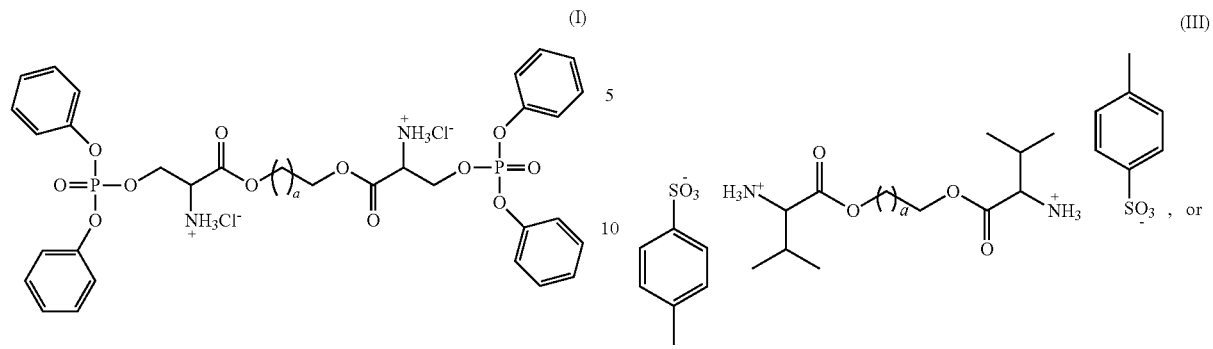

(I)

where a is an integer from about 1 to about 20.

In one or more embodiments, the poly(ester urea) (PEU) based adhesive of the present invention includes any one or more of the above referenced embodiments of the first aspect of the present invention wherein the second amino acid based polyester monomer comprises two amino acids selected from the group consisting of alanine (ala—A), glycine (gly—G), isoleucine (ile—I), leucine (leu—L), methionine (met—M), phenylalanine (phe—F), threonine (thr—T), tryptophan (trp—W), tyrosine (tyr—Y), or valine (val—V). In one or more embodiments, the poly(ester urea) (PEU) based adhesive of the present invention includes any one or more of the above referenced embodiments of the first aspect of the present invention wherein the second amino acid based polyester monomer comprises valine or isoleucine.

In one or more embodiments, the poly(ester urea) (PEU) based adhesive of the present invention includes any one or more of the above referenced embodiments of the first aspect of the present invention wherein the second amino acid based polyester monomer has the formula:

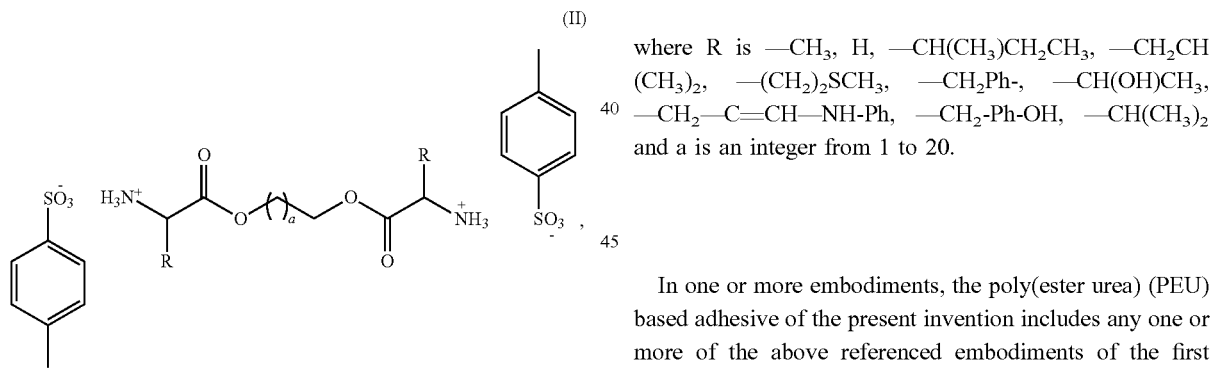

(II), (III), (IV)

where R is —CH$_3$, H, —CH(CH$_3$)CH$_2$CH$_3$, —CH$_2$CH(CH$_3$)$_2$, —(CH$_2$)$_2$SCH$_3$, —CH$_2$Ph-, —CH(OH)CH$_3$, —CH$_2$—C=CH—NH-Ph, —CH$_2$-Ph-OH, —CH(CH$_3$)$_2$ and a is an integer from 1 to 20.

In one or more embodiments, the poly(ester urea) (PEU) based adhesive of the present invention includes any one or more of the above referenced embodiments of the first aspect of the present invention having the formula:

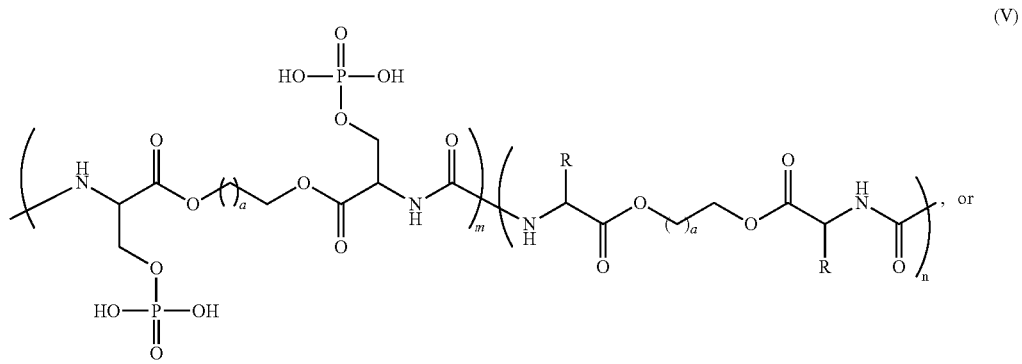

(V)

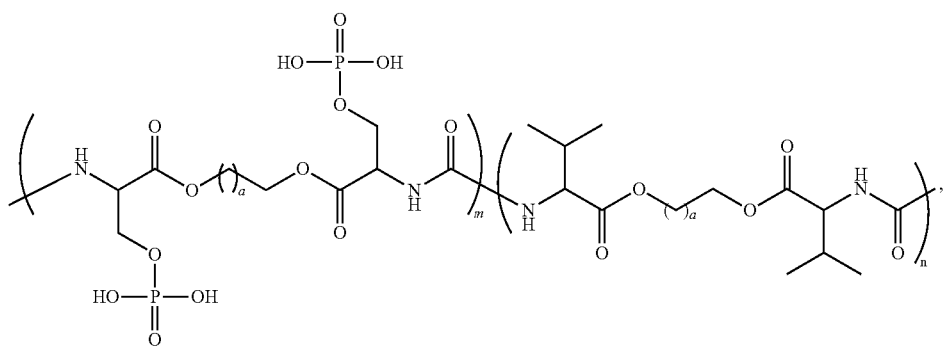

where R is —CH₃, H, —CH(CH₃)CH₂CH₃, —CH₂CH(CH₃)₂, —(CH₂)₂SCH₃, —CH₂Ph-, —CH(OH)CH₃, —CH₂—C=CH—NH-Ph, —CH₂-Ph-OH, —CH(CH₃)₂; a is an integer from 1 to 20; m is a mole percent of from about 1% to about 20%; and n is a mole percent from about 80% to about 99%.

In one or more embodiments, the poly(ester urea) (PEU) based adhesive of the present invention includes any one or more of the above referenced embodiments of the first aspect of the present invention wherein the crosslinking agent is a divalent salt of a metal selected from the group consisting of calcium, magnesium, strontium, barium, zinc, and combinations thereof. In one or more embodiments, the poly(ester urea) (PEU) based adhesive of the present invention includes any one or more of the above referenced embodiments of the first aspect of the present invention wherein the crosslinking agent comprises from about 1 mole percent to about 20 mole percent of the PEU based adhesive.

In a second aspect, the present invention is directed to a method of making a poly(ester urea) (PEU) based adhesive comprising: preparing a PEU polymer having one or more side chains comprising a phosphate group; adding a crosslinking agent comprising a divalent metal salt. In some embodiments, molar ratio of the PEU polymer having one or more side chains comprising a phosphate group to the crosslinking agent comprising a divalent metal salt is from about 1:1 to about 10:1 In one or more embodiments, the poly(ester urea) (PEU) based adhesive of the present invention includes any one or more of the above referenced embodiments of the second aspect of the present invention wherein the PEU polymer having one or more side chains comprising a phosphate group has formula V or VI, above.

In one or more embodiments, the poly(ester urea) (PEU) based adhesive of the present invention includes any one or more of the above referenced embodiments of the second aspect of the present invention wherein the step of preparing a PEU polymer further comprises: preparing a first amino acid based polyester monomer comprising two phosphorylated amino acids separated by from 1 to 20 carbon atoms; preparing a second amino acid based polyester monomer comprising two amino acids separated by from 2 to 20 carbon atoms; reacting the first amino acid based polyester monomer and the second amino acid based polyester monomer with phosgene, diphosgene or triphosgene to introduce urea bonds between and among the first and second amino acid based polyester monomer to form the PEU polymer. In one or more embodiments, the poly(ester urea) (PEU) based adhesive of the present invention includes any one or more of the above referenced embodiments of the second aspect of the present invention wherein the first amino acid based polyester monomer comprises two phosphorylated serine molecules separated by from 2 to 20 carbon atoms.

In one or more embodiments, the poly(ester urea) (PEU) based adhesive of the present invention includes any one or more of the above referenced embodiments of the second aspect of the present invention wherein the second amino acid based polyester monomer comprises two amino acids selected from the group consisting of alanine (ala—A), glycine (gly—G), isoleucine (ile—I), leucine (leu—L), methionine (met—M), phenylalanine (phe—F), threonine (thr—T), tryptophan (trp—W), tyrosine (tyr—Y), or valine (val—V), separated by from 2 to 20 carbon atoms. In one or more embodiments, the poly(ester urea) (PEU) based adhesive of the present invention includes any one or more of the above referenced embodiments of the second aspect of the present invention wherein the second amino acid based polyester monomer comprises valine or isoleucine molecules.

In a third aspect, the present invention is directed to a method of bonding bone to bone or bone to metal using the poly(ester urea) (PEU) based adhesive comprising: preparing a first surface and second surface to be joined; preparing a PEU polymer having one or more side chains comprising a phosphate group; mixing a crosslinking agent comprising a divalent metal salt into the PEU polymer to form a poly(ester urea) (PEU) based adhesive; applying the PEU polymer/crosslinking agent mixture to one or both of the first and second surfaces to be joined; placing the first and the second surfaces to be joined in contact with each other; and allowing the poly(ester urea) (PEU) based adhesive to crosslink, thereby forming a bond between the first surface and the second surface.

BRIEF DESCRIPTION OF THE DRAWINGS

For a more complete understanding of the features and advantages of the present invention, reference is now made to the detailed description of the invention along with the accompanying figures.

The inset in (FIG. 2A) shows magnification from δ=7.1-7.3 ppm of $^1$H NMR spectra; characteristic peaks of the diphenyl protecting groups disappear after deprotection and δ=4.0-4.5 ppm. A triplet at δ=~4.37 ppm is characteristic of the proton environment on the methylene group attached to the deprotected phosphate group, which is not prominent before deprotection (DMSO-$d_6$, 500 MHz, 30° C.).

Figure 3:
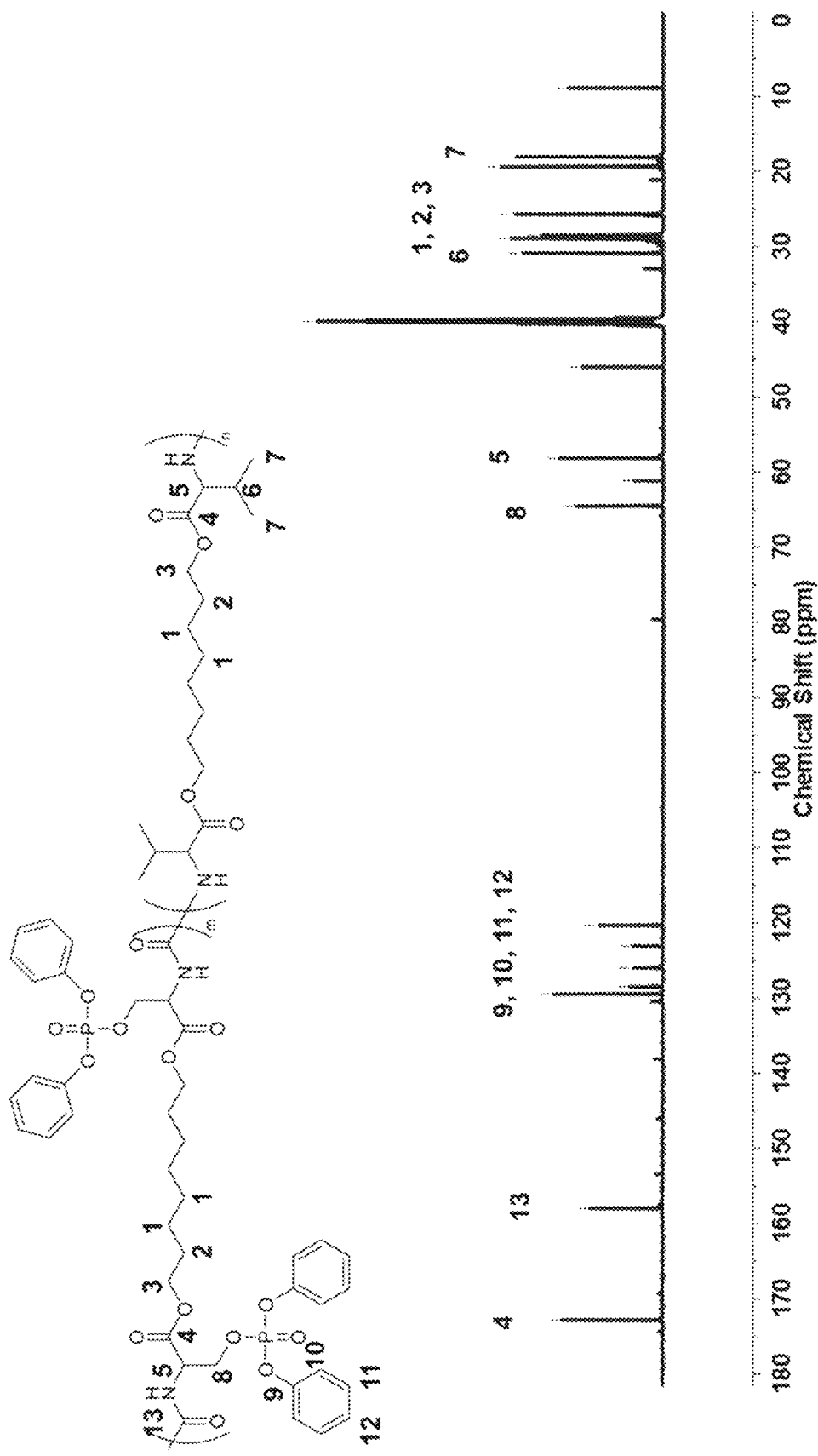

FIG. 3 is a $^{13}$C NMR spectra of 5% Poly(SerDPP-co-Val) (DMSO-$d_6$, 500 MHz, 30° C.).

Figure 4:
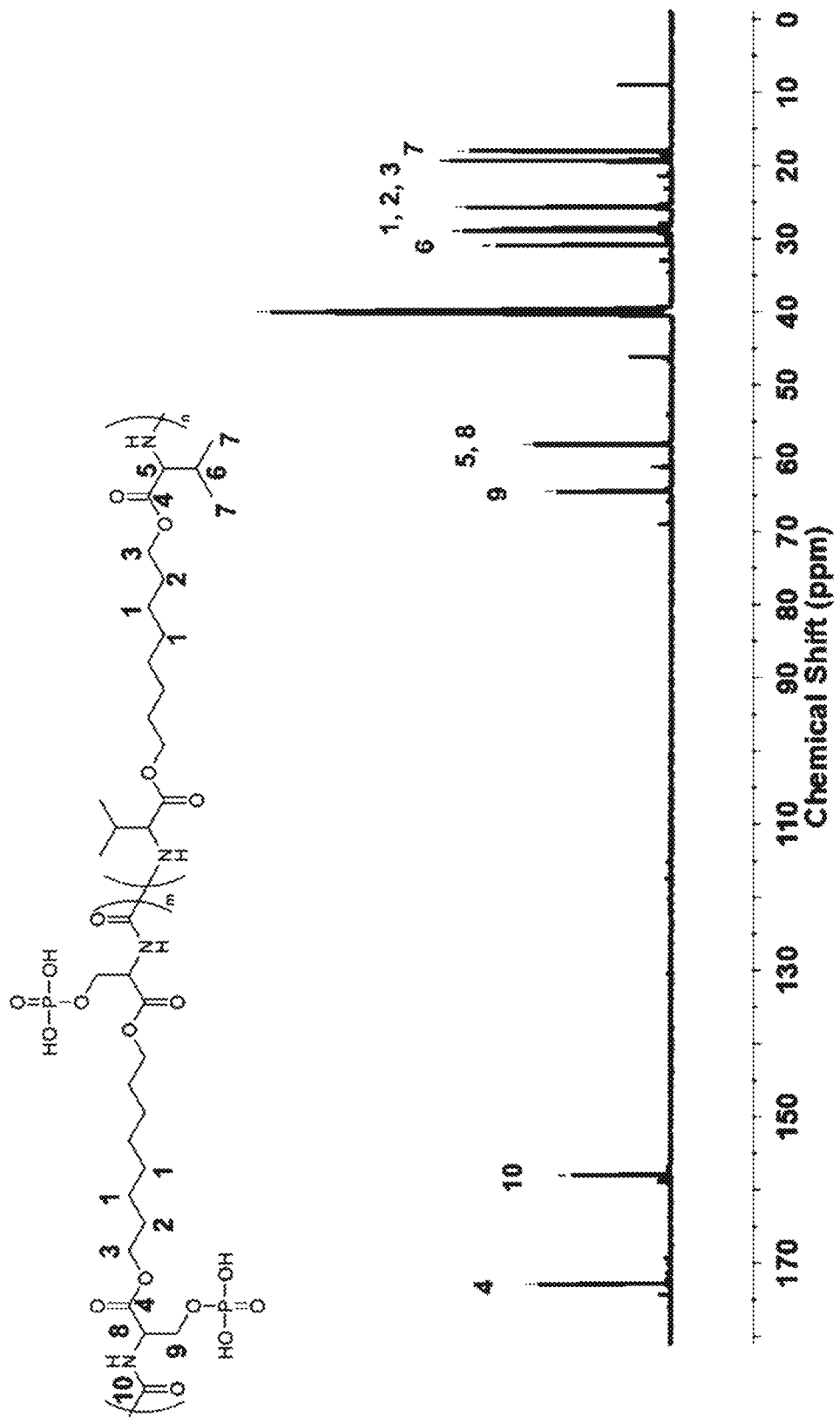

FIG. 4 is a $^{13}$C NMR spectra of 5% Poly(pSer-co-Val) (DMSO-$d_6$, 500 MHz, 30° C.).

Figure 5:
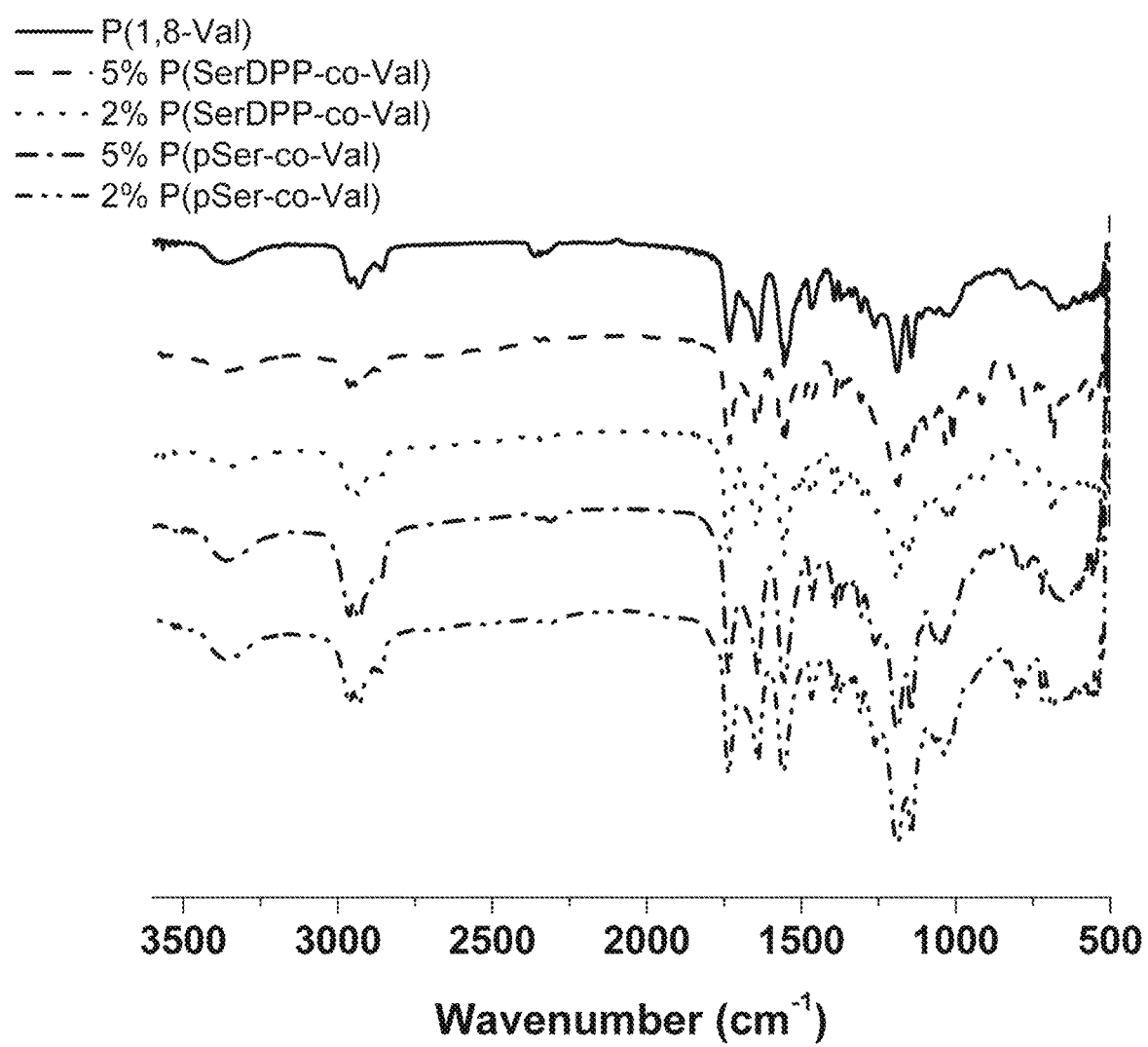

FIG. 5 is a schematic showing the ATR-IR spectra of Poly(1,8-Val), Poly(SerDPP-co-Val) and Poly(pSer-co-Val) with the peaks corresponding to the P=O (1040 cm$^{-1}$) and P—O stretching (710-675 cm$^{-1}$) highlighted and labelled.

Figure 6:
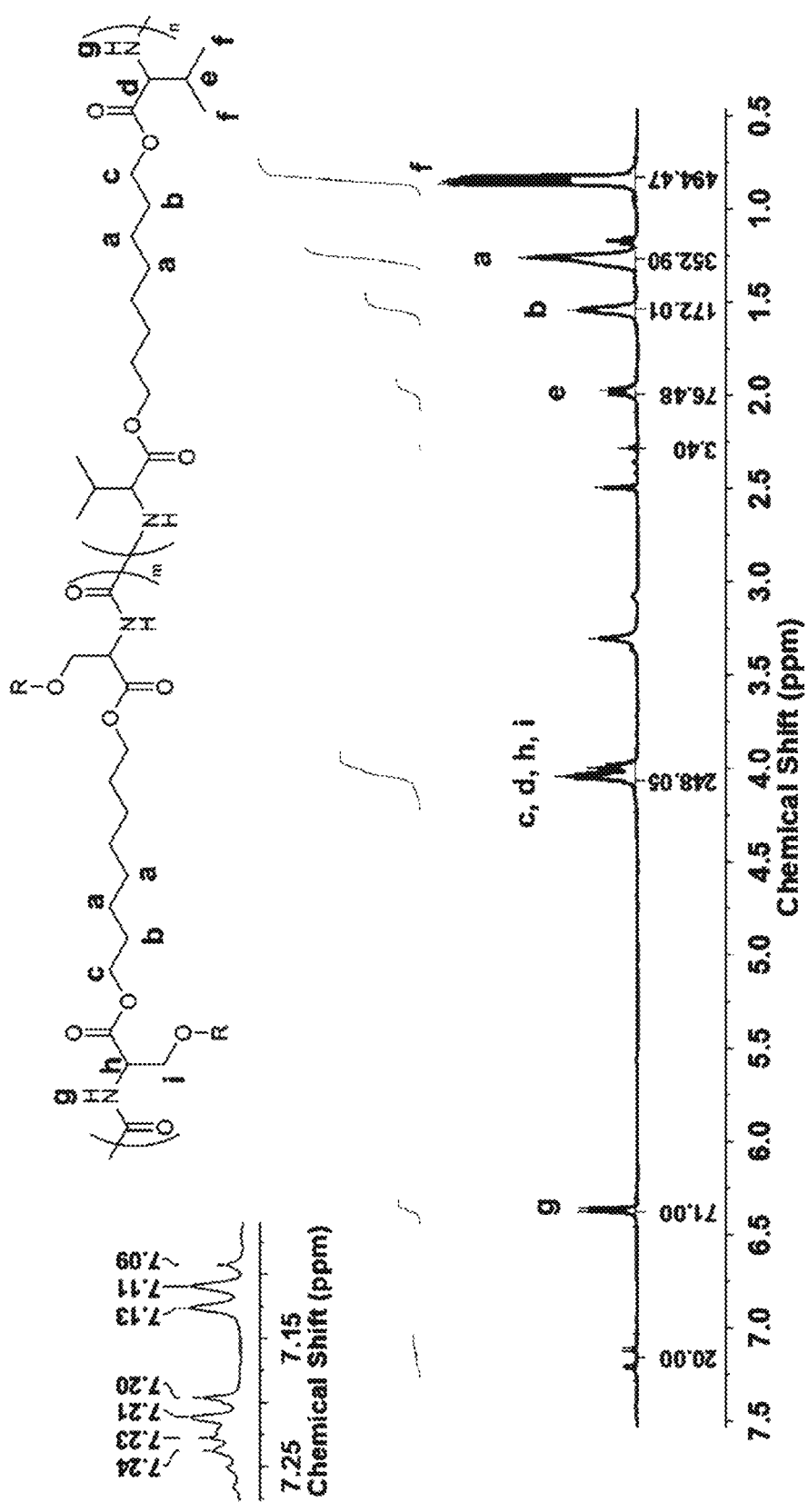

FIG. 6 is a $^1$H NMR spectra of 2% Poly(SerDPP-co-Val). R group denotes diphenyl protected phosphate groups. The inset shows aromatic peaks from the diphenyl protecting groups (DMSO-$d_6$, 500 MHz, 30° C.).

Figure 7:
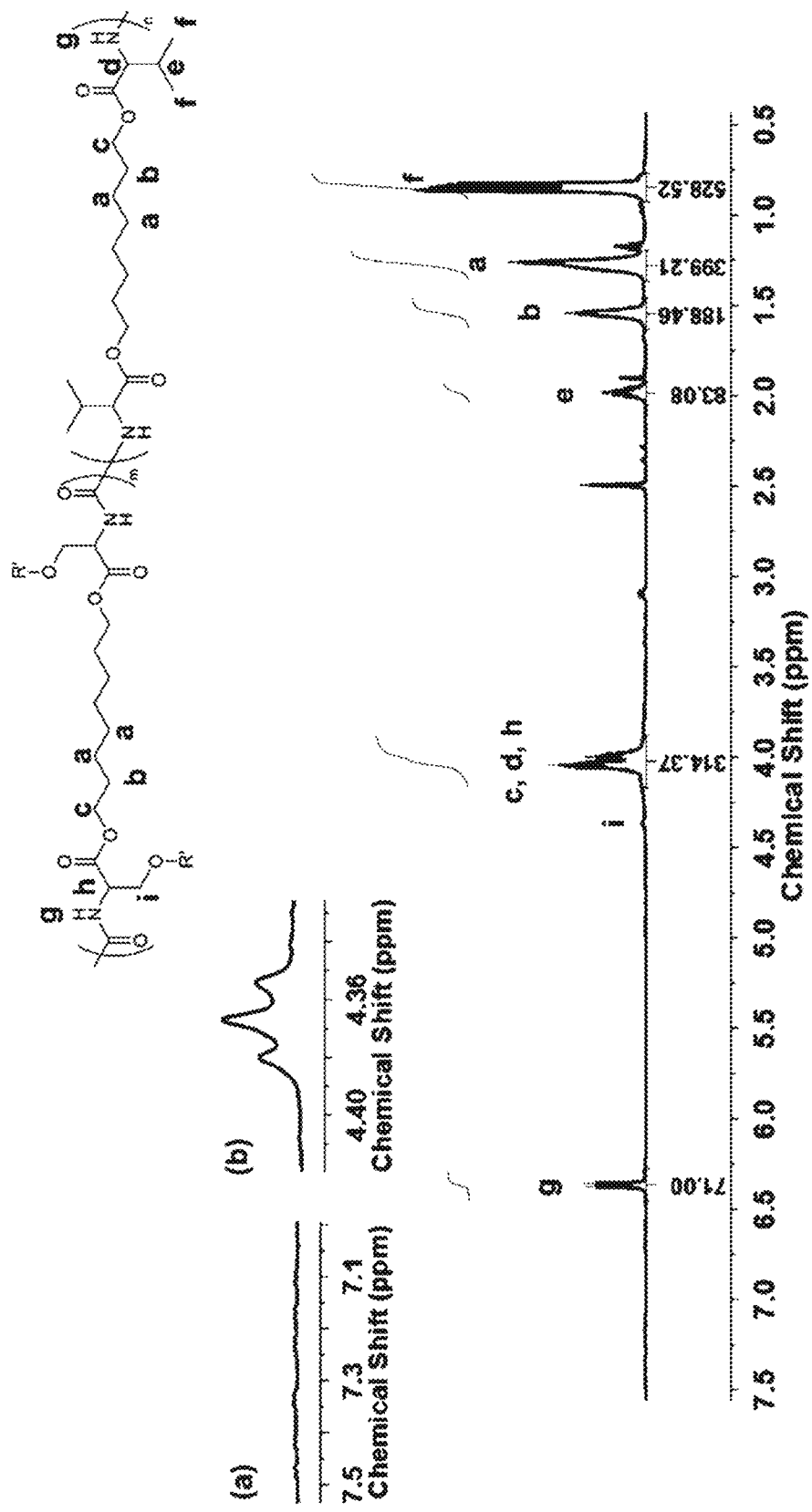

FIG. 7 is a $^1$H NMR spectra of 2% Poly(pSer-co-Val). R' denotes deprotected phosphate groups. Inset (a) shows disappearance of the aromatic peaks between 7.0-7.25 ppm confirming deprotection of the diphenyl groups; and insert (b) shows the presence of a triplet around 4.36 ppm, corresponding to the proton environment on methylene group attached to the deprotected phosphate group (DMSO-$d_6$, 500 MHz, 30° C.).

Figure 8:
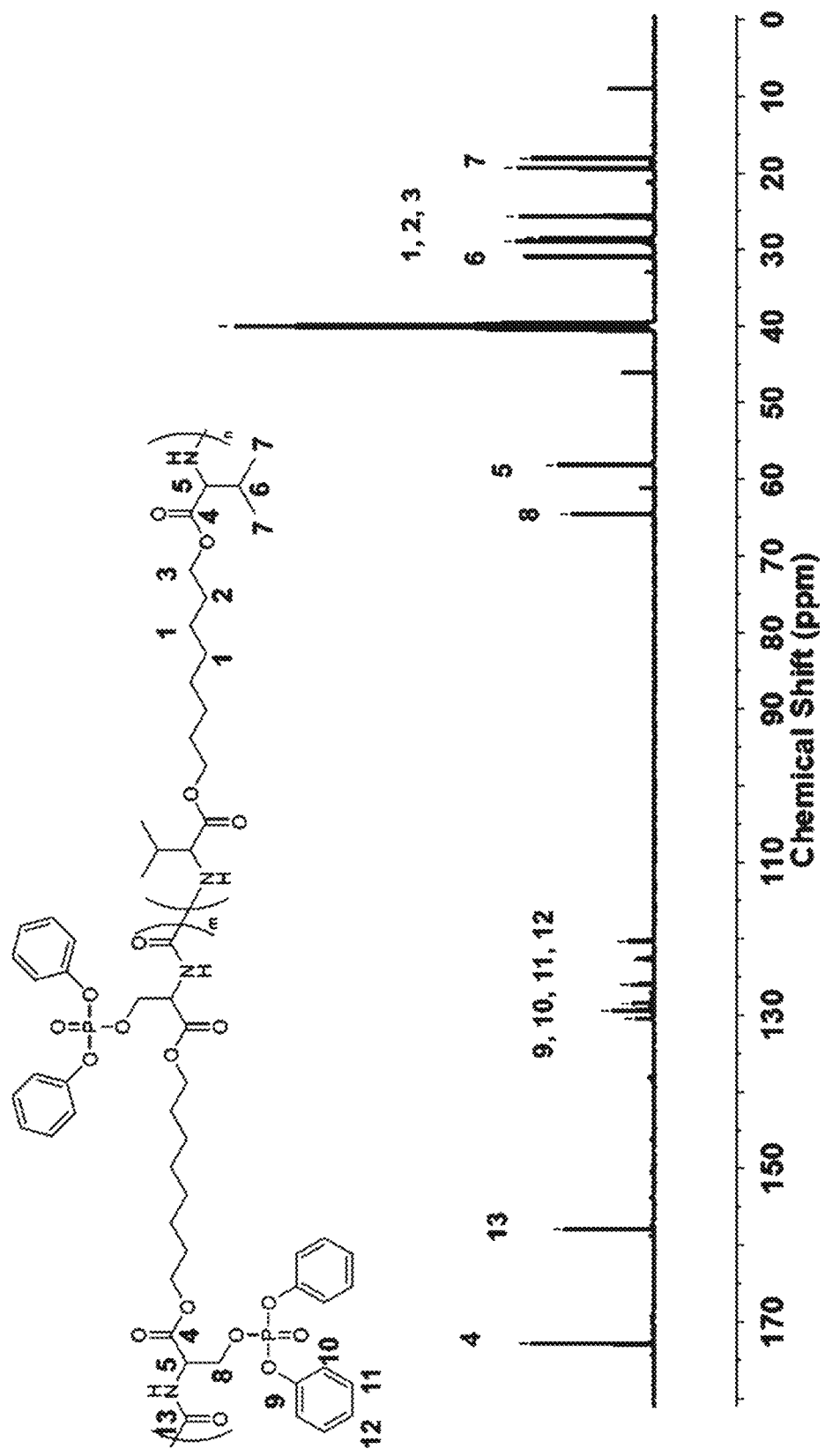

FIG. 8 is a $^{13}$C NMR spectra of 2% Poly(SerDPP-co-Val) (DMSO-$d_6$, 500 MHz, 30° C.).

Figure 9:
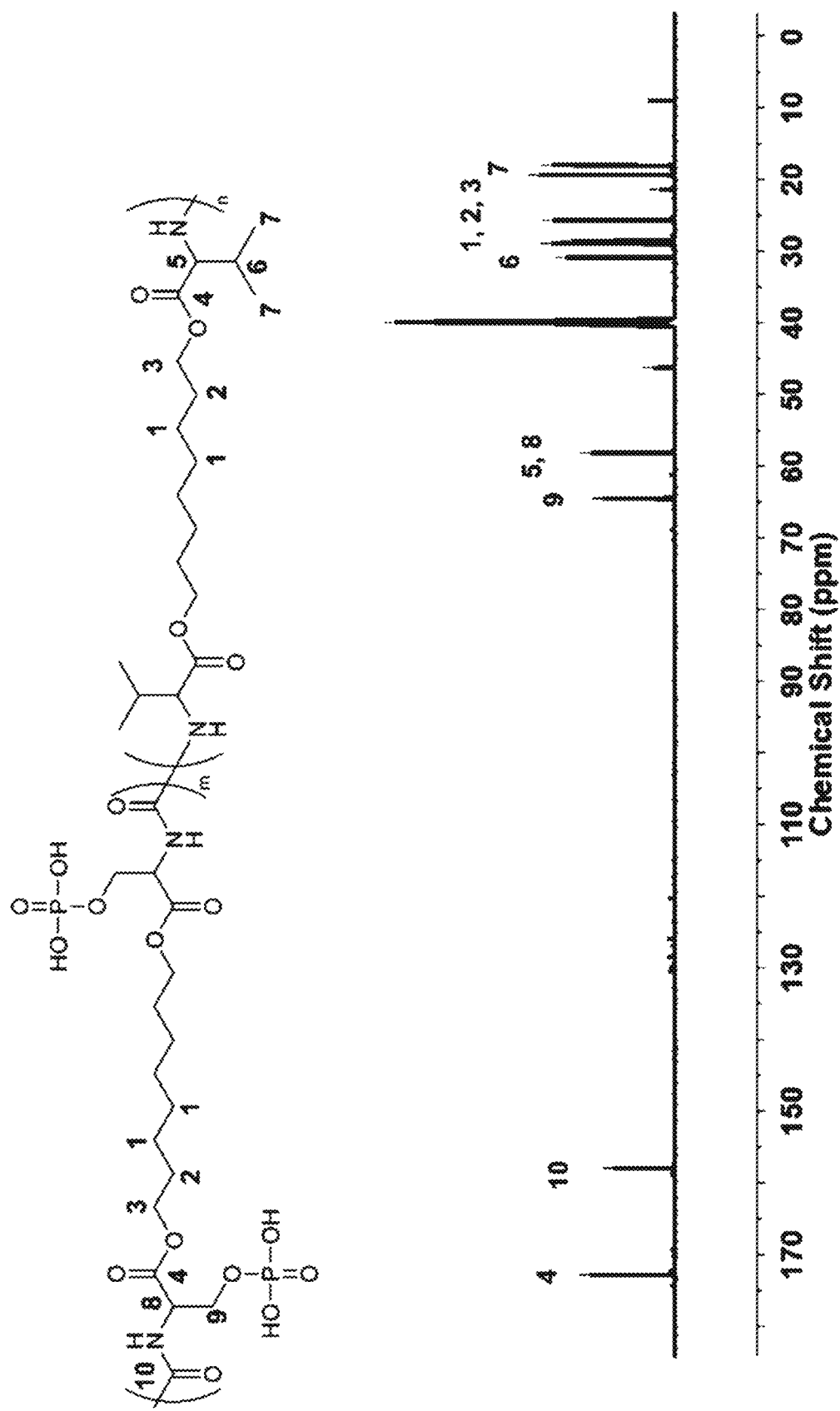

FIG. 9 is a $^{13}$C NMR spectra of 2% Poly(pSer-co-Val) (DMSO-$d_6$, 500 MHz, 30° C.).

Figure 10:
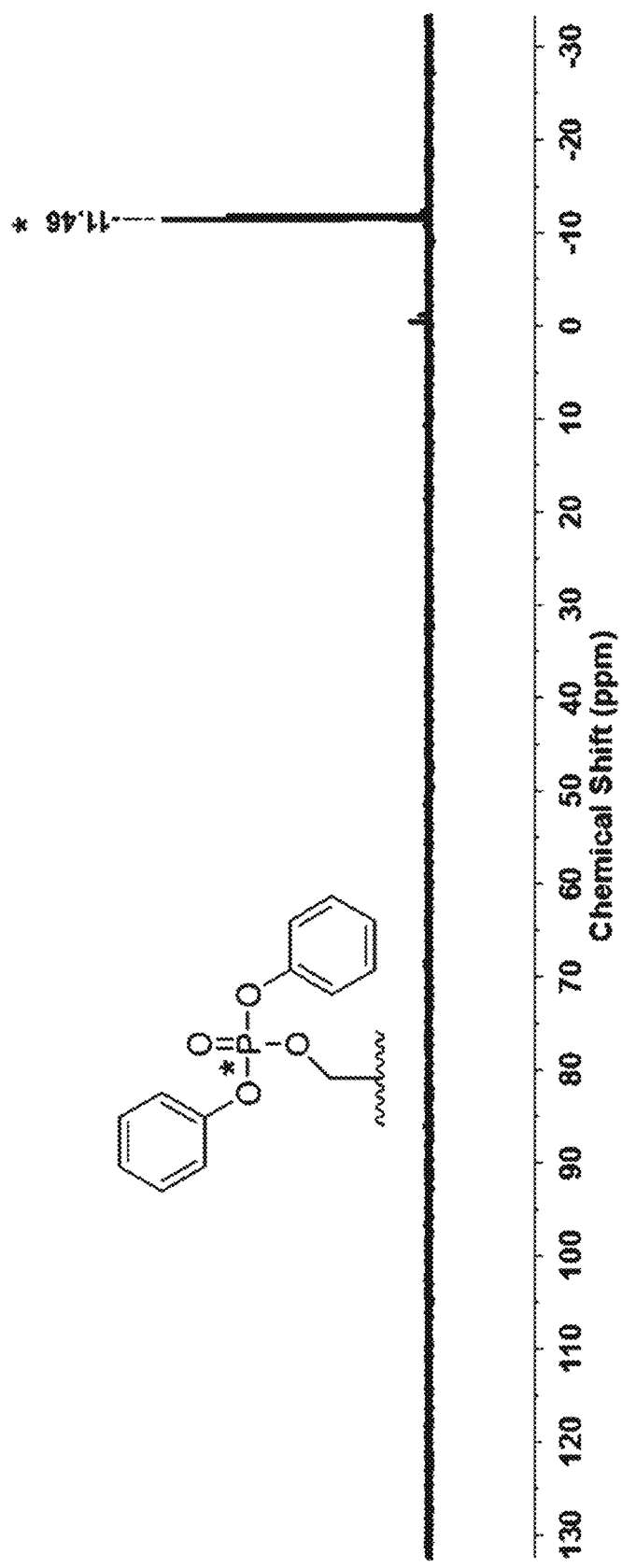

FIG. 10 is a $^{31}$P NMR spectra of 2% Poly(SerDPP-co-Val) (DMSO-$d_6$, 500 MHz, 30° C.).

Figure 11:
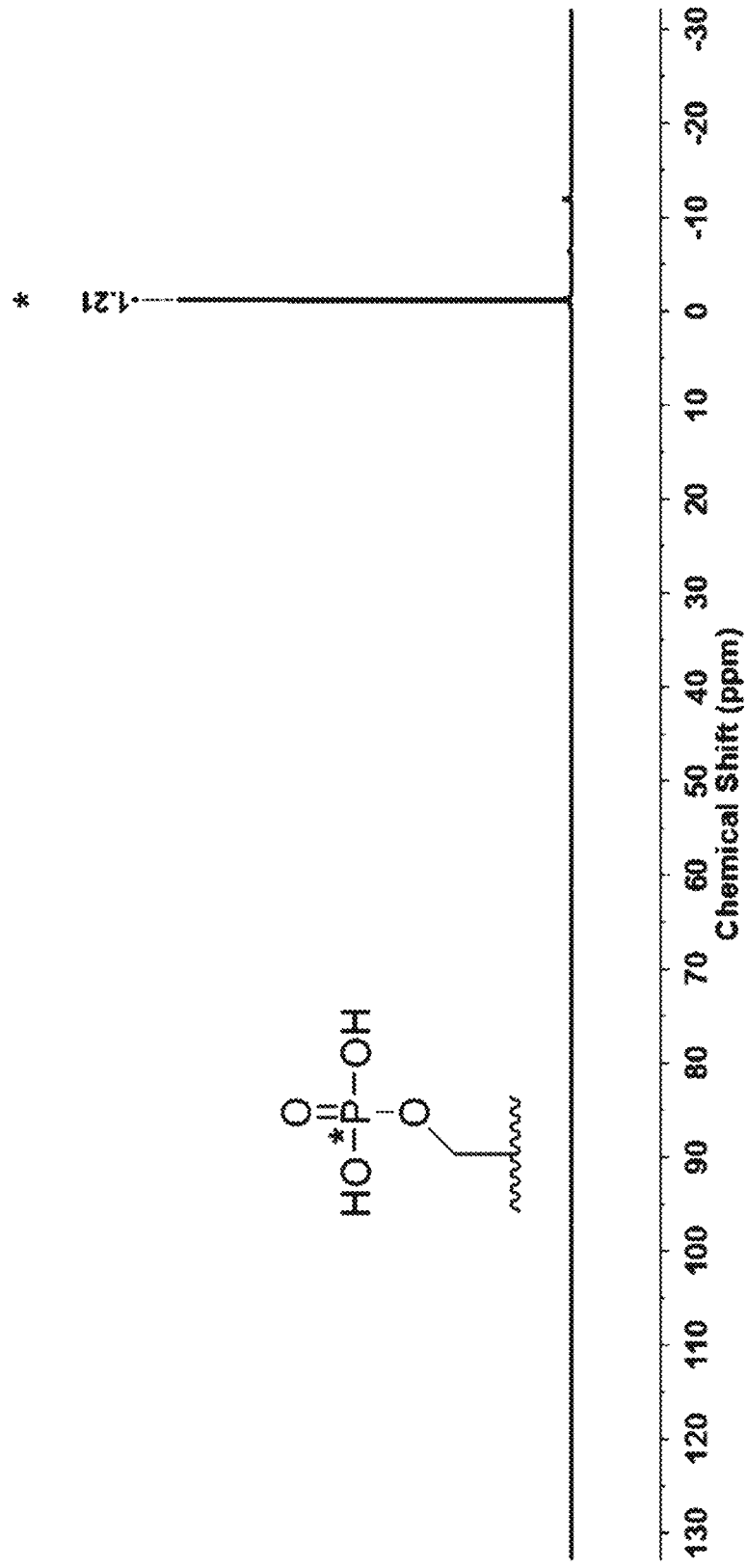

FIG. 11 is a $^{31}$P NMR spectra of 2% Poly(pSer-co-Val) (DMSO-$d_6$, 500 MHz, 30° C.).

Figure 12:
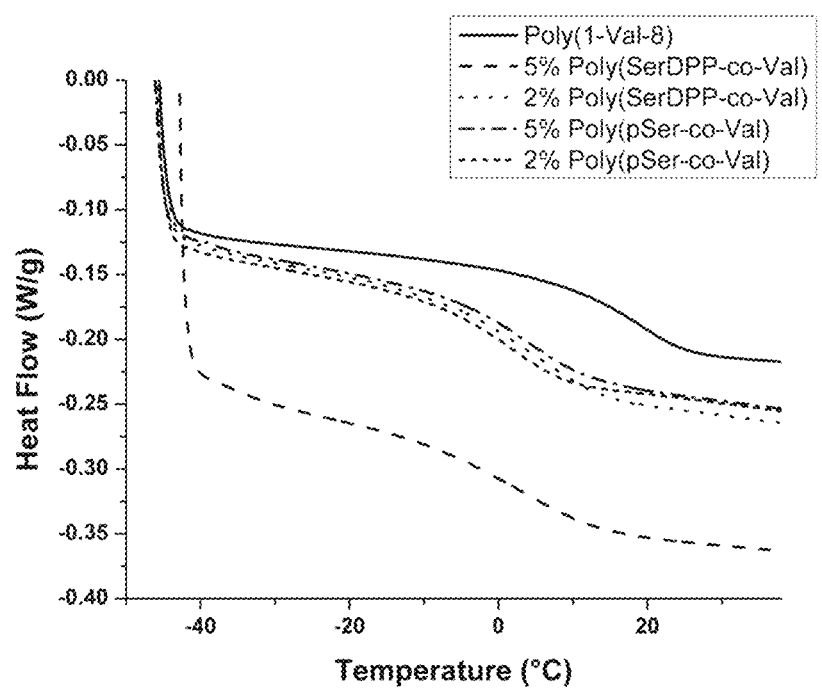

FIG. 12 is a graph showing the DSC curves used to determine the glass transition temperatures ($T_g$) of Poly(1,8-Val), 5% Poly(SerDPP-co-Val), 2% Poly(SerDPP-co-Val), 5% Poly(pSer-co-Val) and 2% Poly(pSer-co-Val). $T_g$ of the phosphate functionalized polymers do not show significant change after deprotection because of the low functionality on the polymer backbone chains.

Figure 13:
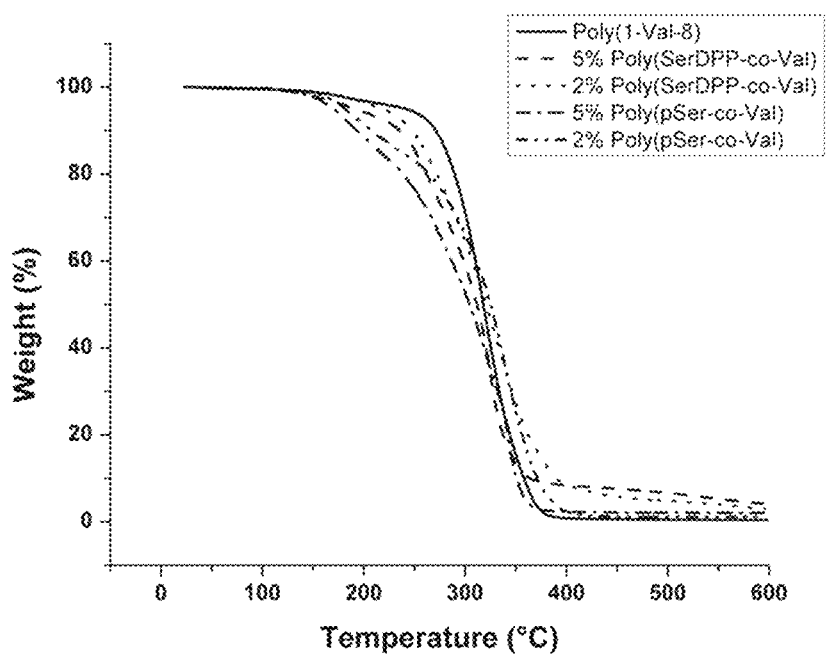

FIG. 13 is a graph showing thermogravimetric analysis curves used to determine the decomposition temperature ($T_d$) of Poly(1,8-Val), 5% Poly(SerDPP-co-Val), 2% Poly(SerDPP-co-Val), 5% Poly(pSer-co-Val) and 2% Poly(pSer-co-Val). A slight decrease in the decomposition temperature is observed after deprotection of the diphenyl groups.

Figure 14A:
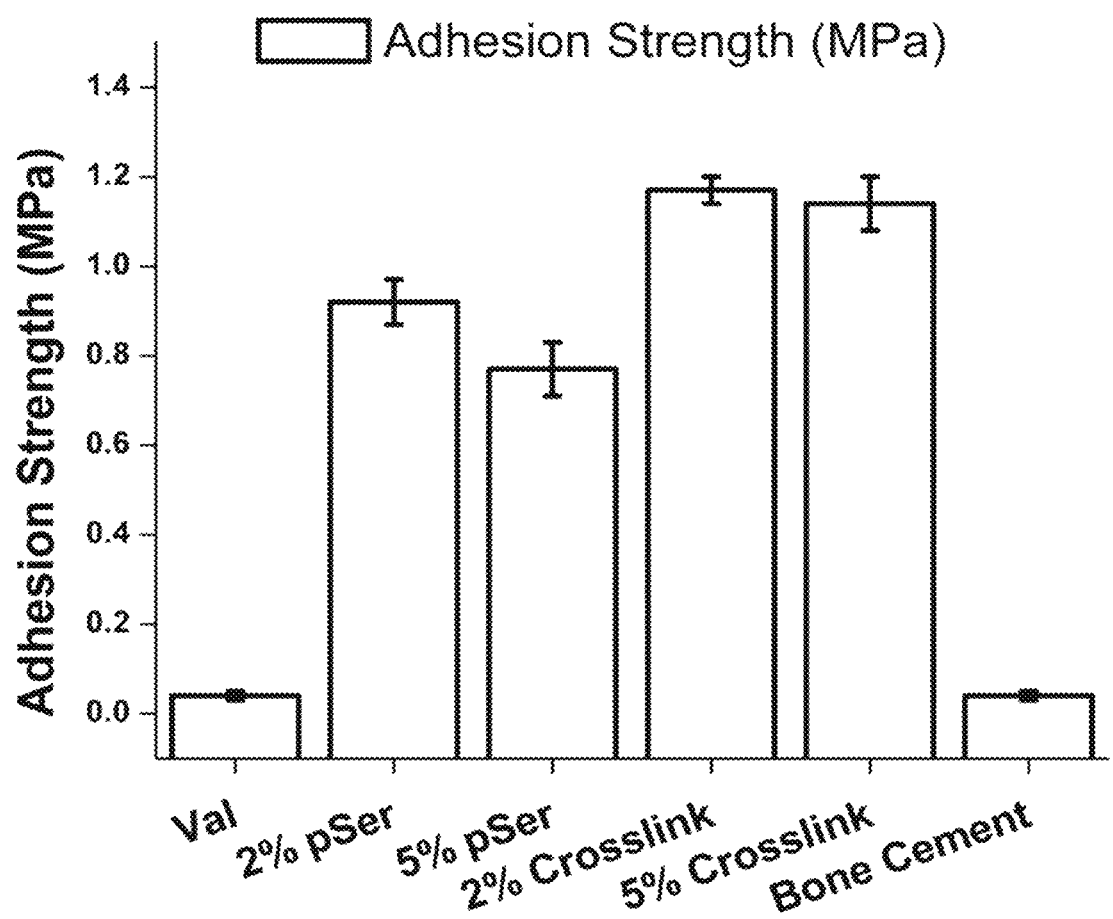
Figure 14B:
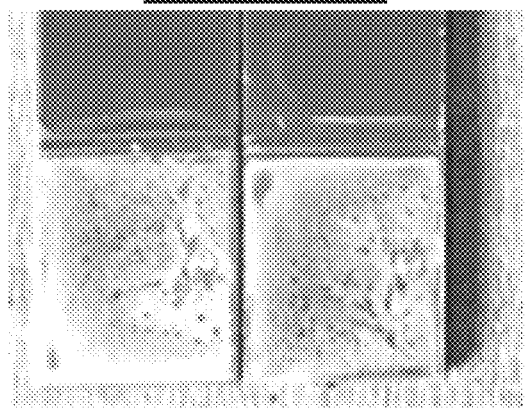
Figure 14C:
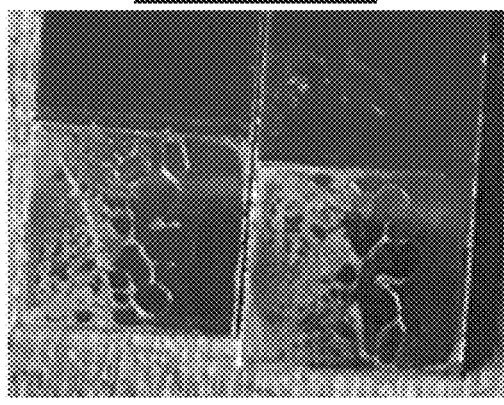
Figure 14D:
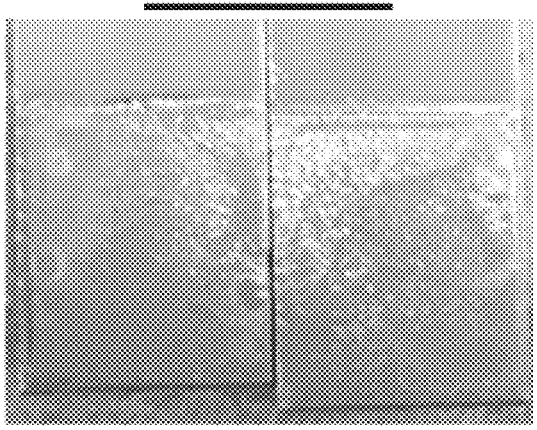
Figure 14E:
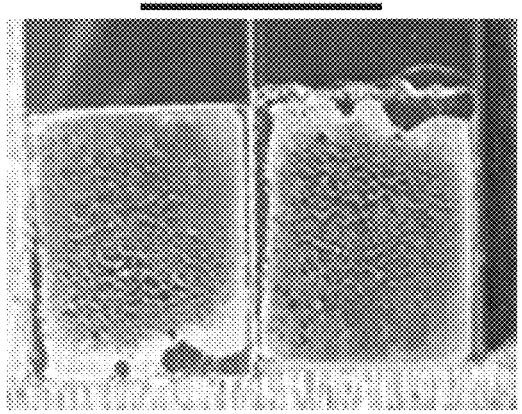
Figure 14F:
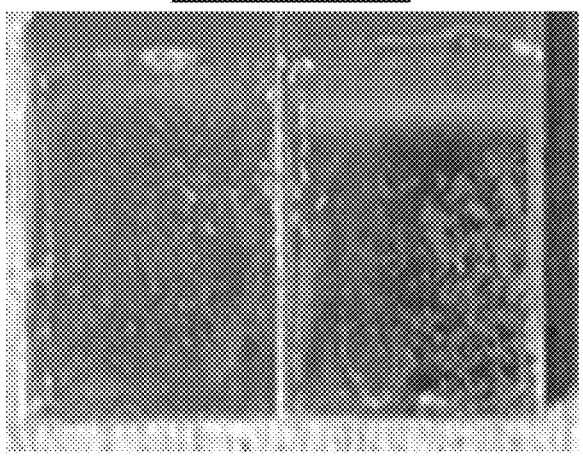
Figure 14G:
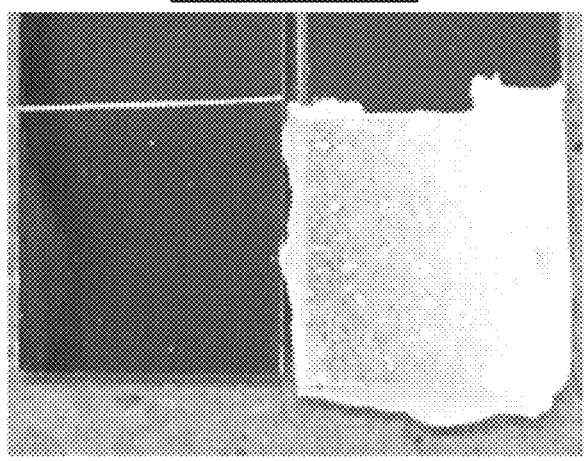

FIGS. 14A-G show the results of lap sheer adhesion studies done on aluminum adherends at room temperature. FIG. 14A is a graph showing adhesion strength for Val—Poly(1-Val-8); 2% and 5% pSer—2% and 5% Poly(pSer-co-Val) respectively; 2% and 5% Crosslink—2% and 5% Poly(pSer-co-Val) crosslinked with 0.3 eq. of Ca$^{2+}$ and a commercially available Bone cement (Simplex P). Adhesion strengths were calculated from average of 10 replicates (n=10) and reported with standard errors. Aluminum adherends show cohesive failure for all samples: Poly(1-Val-8) (FIG. 14B), 2% Poly(pSer-co-Val) (FIG. 14C), 5% Poly (pSer-co-Val) (FIG. 14D), 2% Poly(pSer-co-Val) crosslinked with 0.3 eq. Ca$^{2+}$ (FIG. 14E), 5% Poly(pSer-co-Val) crosslinked with 0.3 eq. Ca$^{2+}$ (FIG. 14F), and Poly(methyl methacrylate) bone cement (FIG. 14G).

Figure 15A:
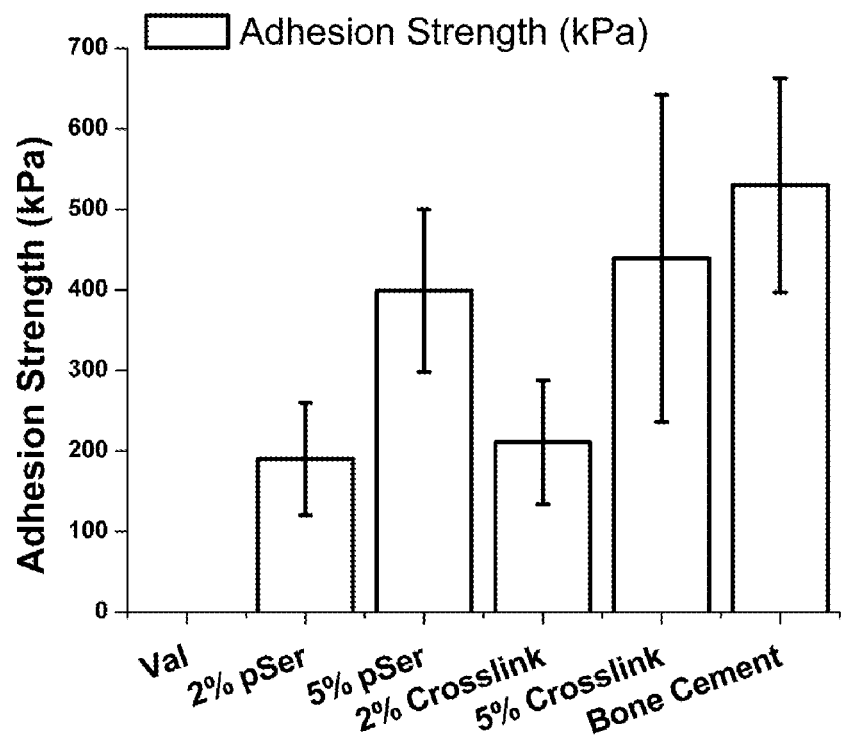
Figure 15B:
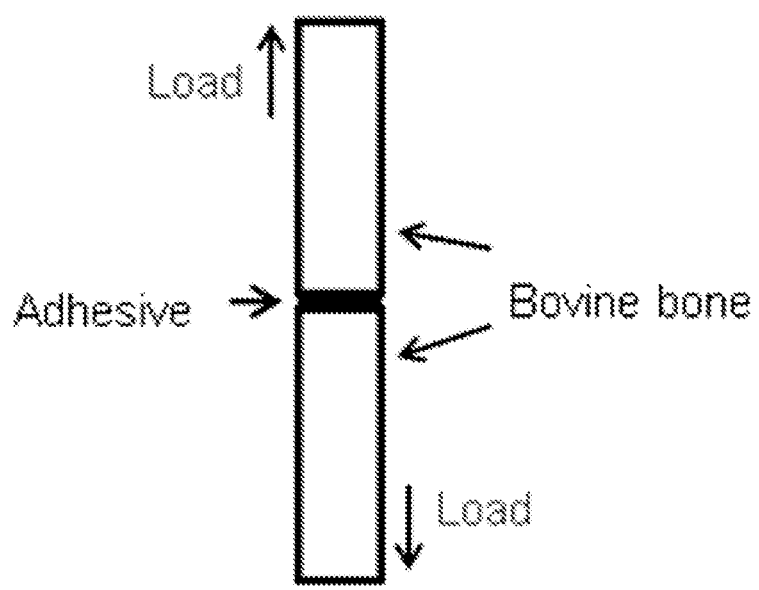
Figure 15C:
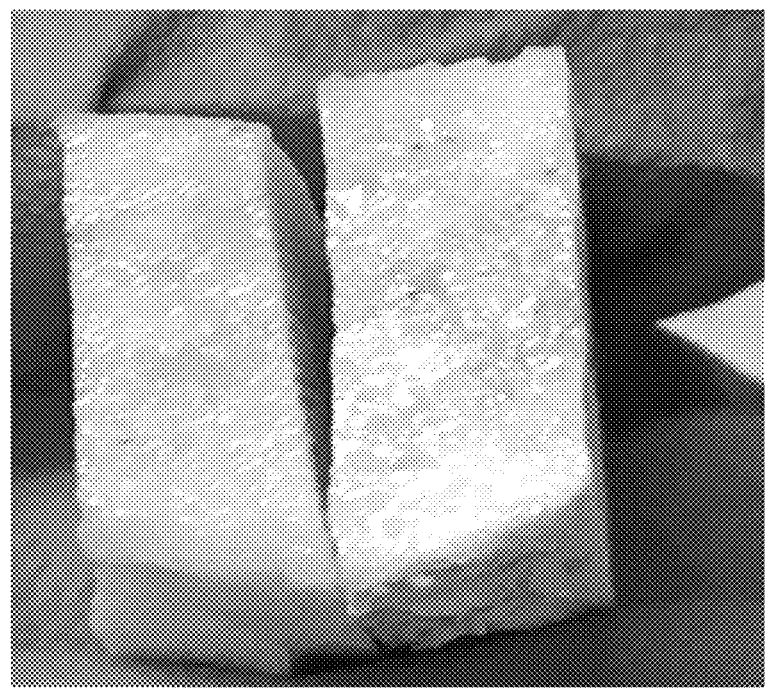

FIGS. 15A-C relate to comparative adhesions strength measurements measuring end-to-end adhesion on bovine bone at room temperature. FIG. 15A is a graph showing the results of end-to-end adhesion tests done on bovine bone at room temperature using Val—Poly(1-Val-8); 2% and 5% pSer—2% and 5% Poly(pSer-co-Val) respectively; 2% and 5% Crosslink—2% and 5% Poly(pSer-co-Val) crosslinked with 0.3 eq. of Ca$^{2+}$, and cement—commercially available PMMA bone cement (Simplex P) (adhesion strengths were calculated from average of 3 replicates (n=3) and reported with standard errors); FIG. 15B is a schematic showing an end-to-end adhesion on bovine bone sample; and FIG. 15C is an image showing cohesive failure of 5% Poly(pSer-co-Val) crosslinked with 0.3 eq. of Ca$^{2+}$.

Figure 16:
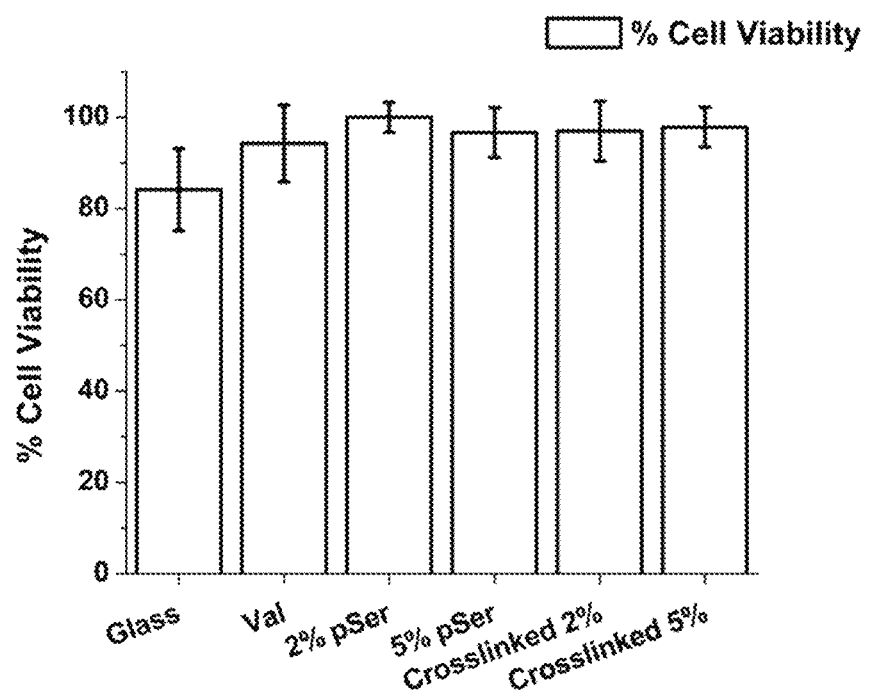

FIG. 16 is a graph showing normalized cell viability of MC3T3 cells on polymers.

Figure 17:
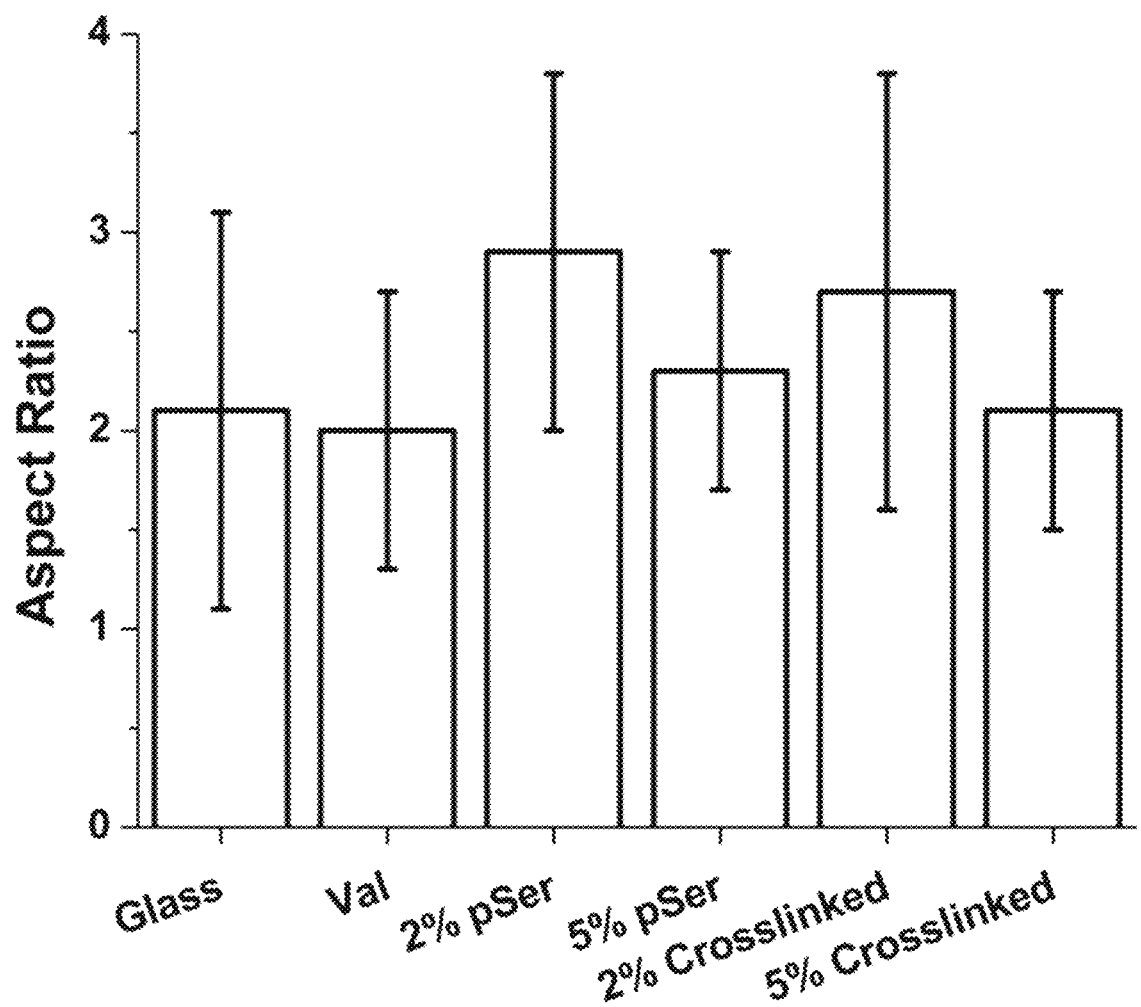

FIG. 17 is a graph showing comparative aspect ratios on different polymers. MC3T3 cells show similar spreading behavior on all samples.

Figure 18:
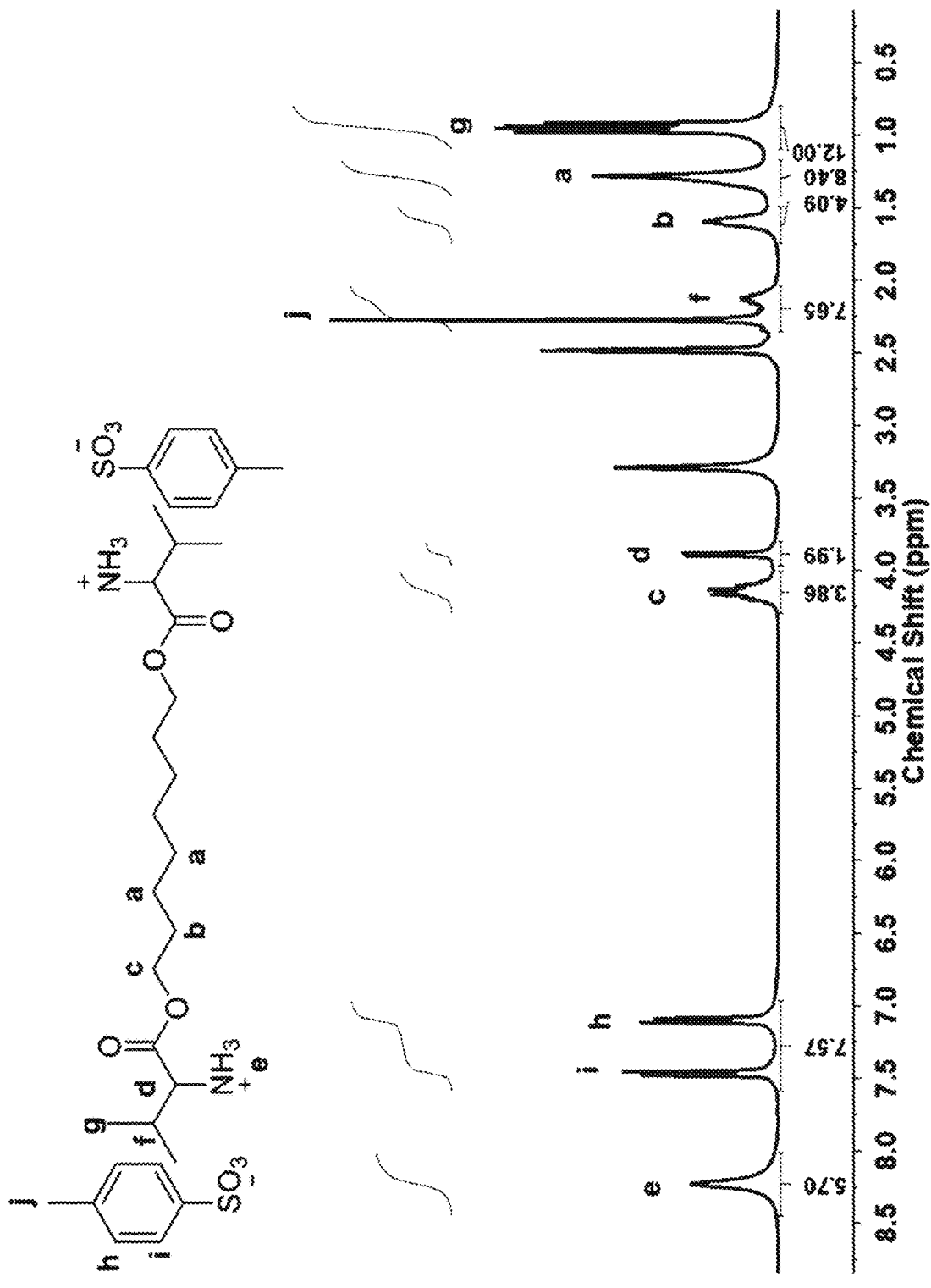

FIG. 18 is a $^1$H NMR spectra of di-p-toluenesulfonic acid salt of bis(L-valine)-1,8-octanyl diester (M1) (DMSO-$d_6$, 300 MHz, 30° C.).

Figure 19:
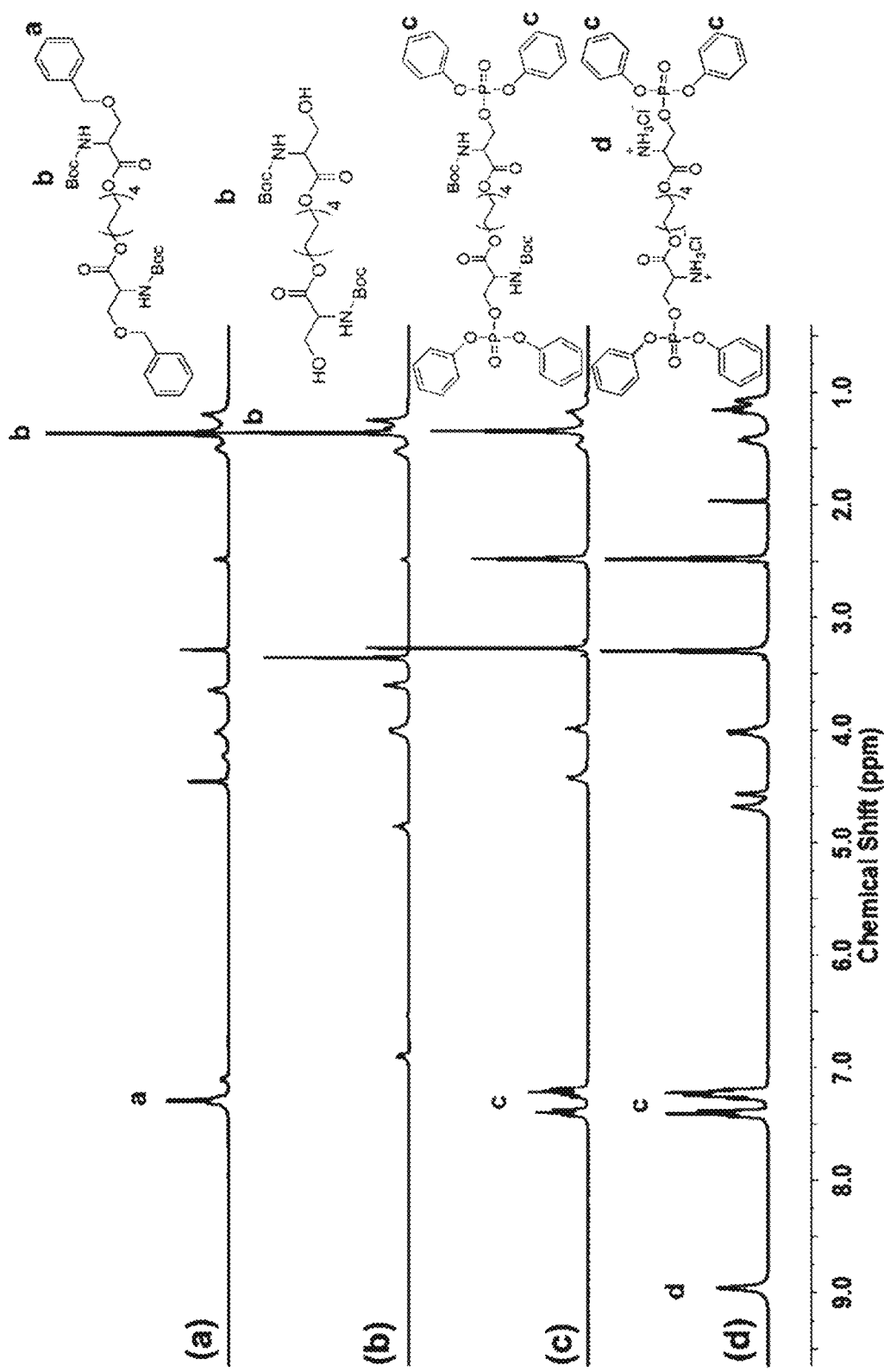

FIG. 19 is a graphic comparison showing $^1$H NMR spectra of phosphoserine monomer synthesis for (a) bis-N-boc-O-benzyl(l-serine)-1,8-octanyl diester (M2), (b) bis-N-boc(l-serine)-1,8-octanyl diester (M3), (c) bis-N-boc-O-diphenylphosphate(l-serine)-1,8-octanyl diester (M4), (d) dihydrochloride salt of bis-O-diphenylphosphate(l-serine)-1,8-octanyl diester (M5) (DMSO-$d_6$, 300 MHz, 30° C.).

Figure 20:
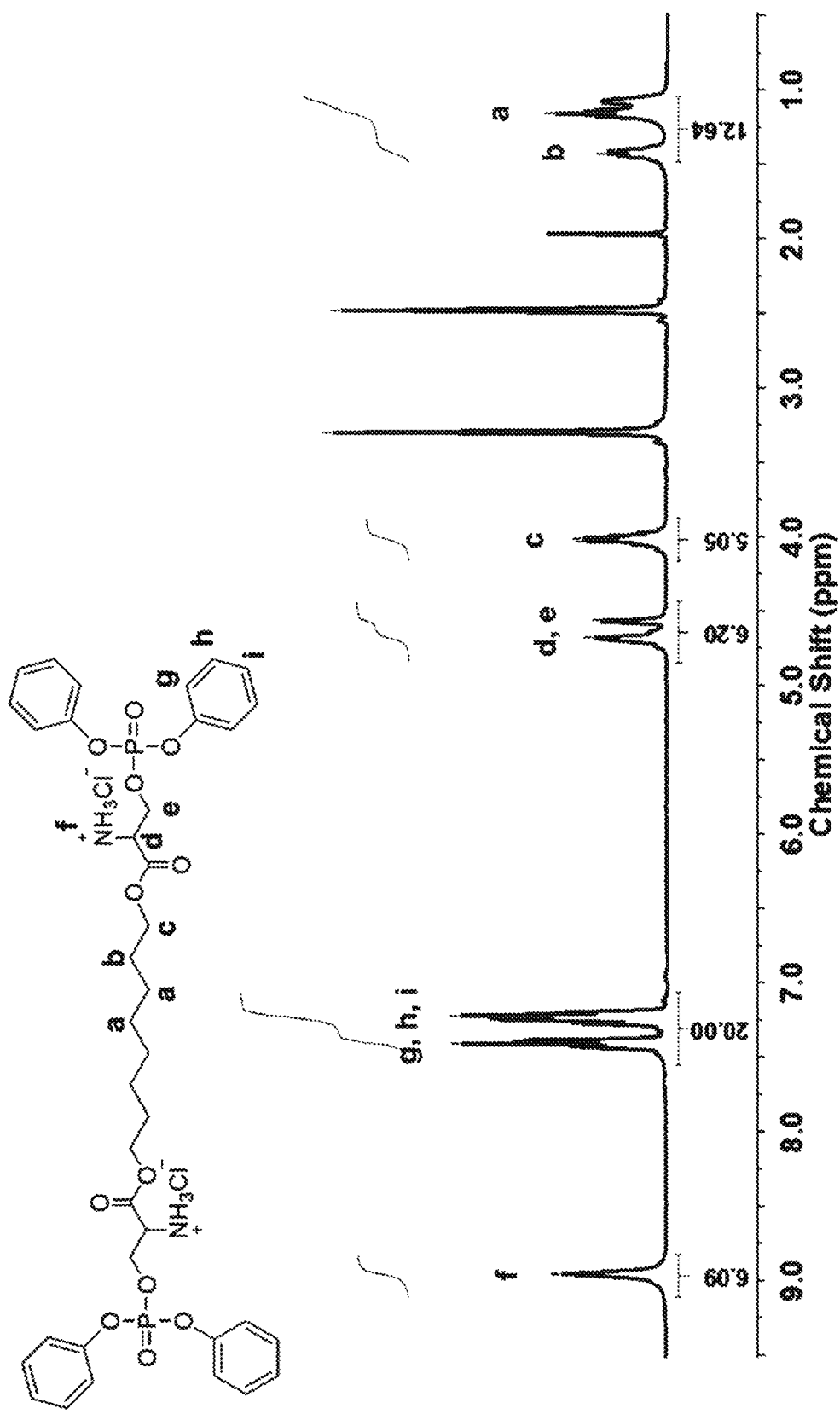

FIG. 20 is a $^1$H NMR spectra of dihydrochloride salt of bis-O-diphenylphosphate(L-serine)-1,8-octanyl diester (M5) (DMSO-$d_6$, 300 MHz, 30° C.).

Figure 21:
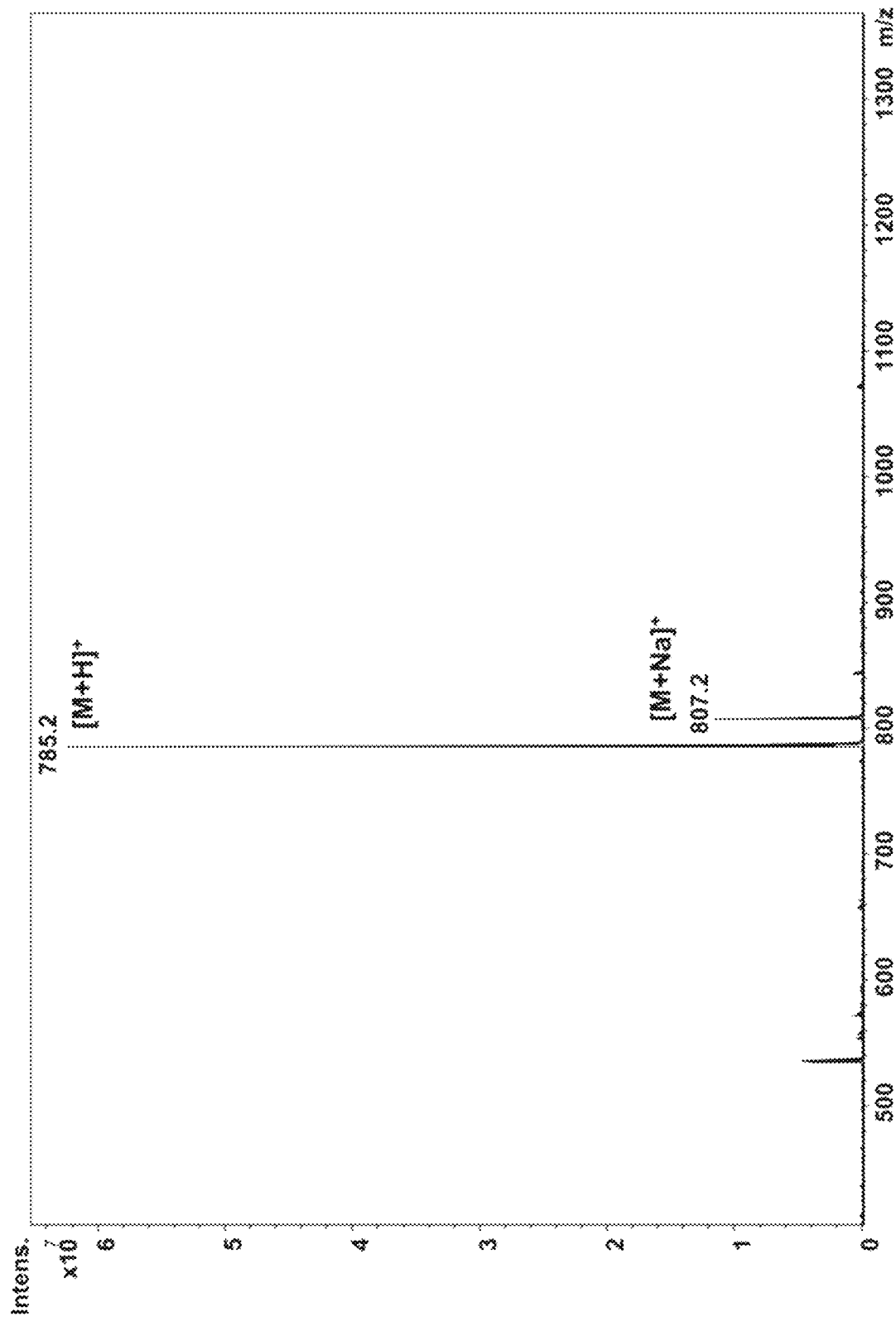

FIG. 21 is an ESI-Mass spectra of dihydrochloride salt of bis-O-diphenylphosphate(L-serine)-1,8-octanyl diester (M5)

Figure 22:
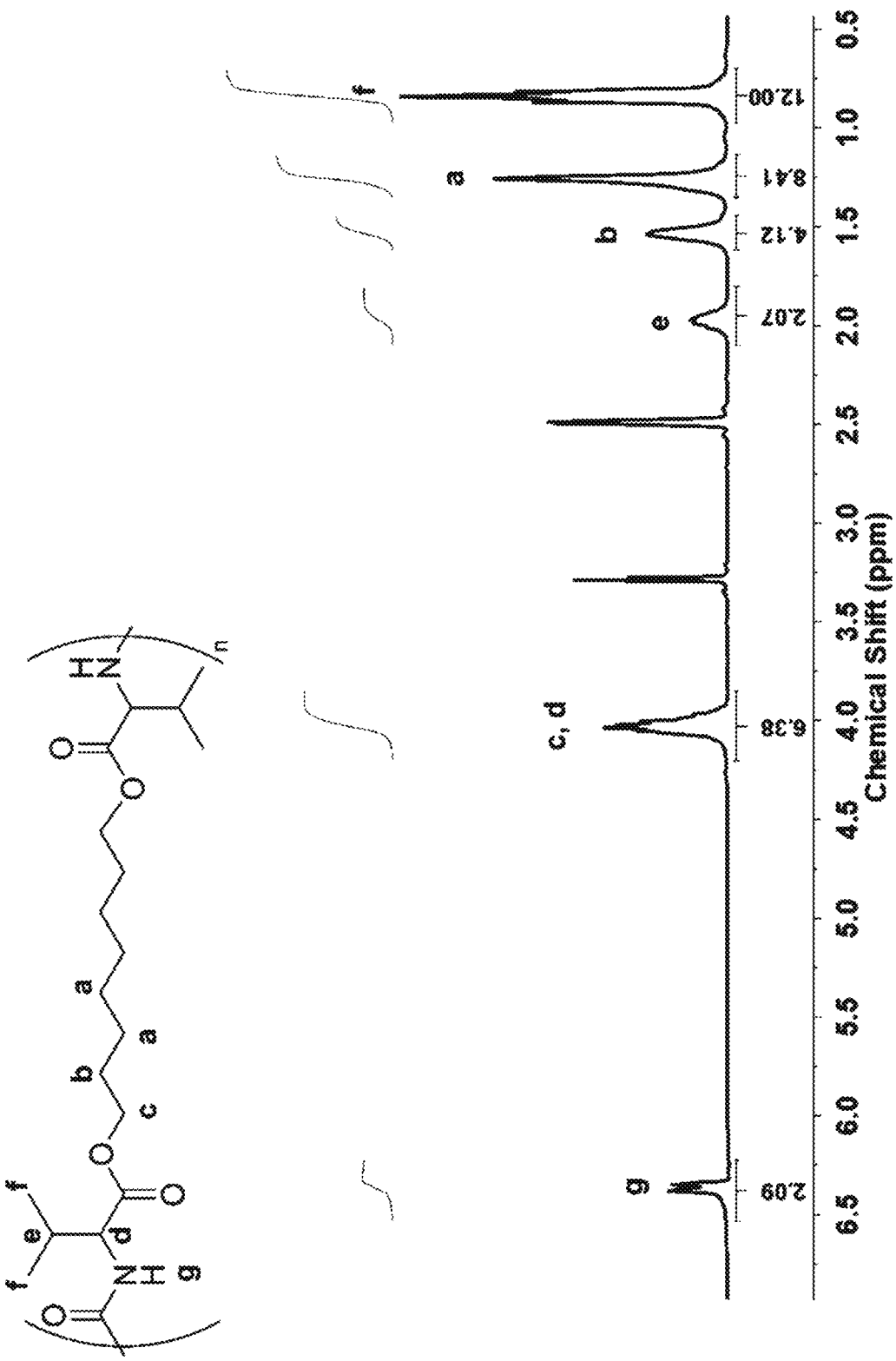

FIG. 22 is a $^1$H NMR spectra of Poly(1-Val-8) (DMSO-$d_6$, 500 MHz, 30° C.).

FIG. 23 is a $^{13}$C NMR spectra of Poly(1-Val-8) (DMSO-$d_6$, 300 MHz, 30° C.).

Figure 24:
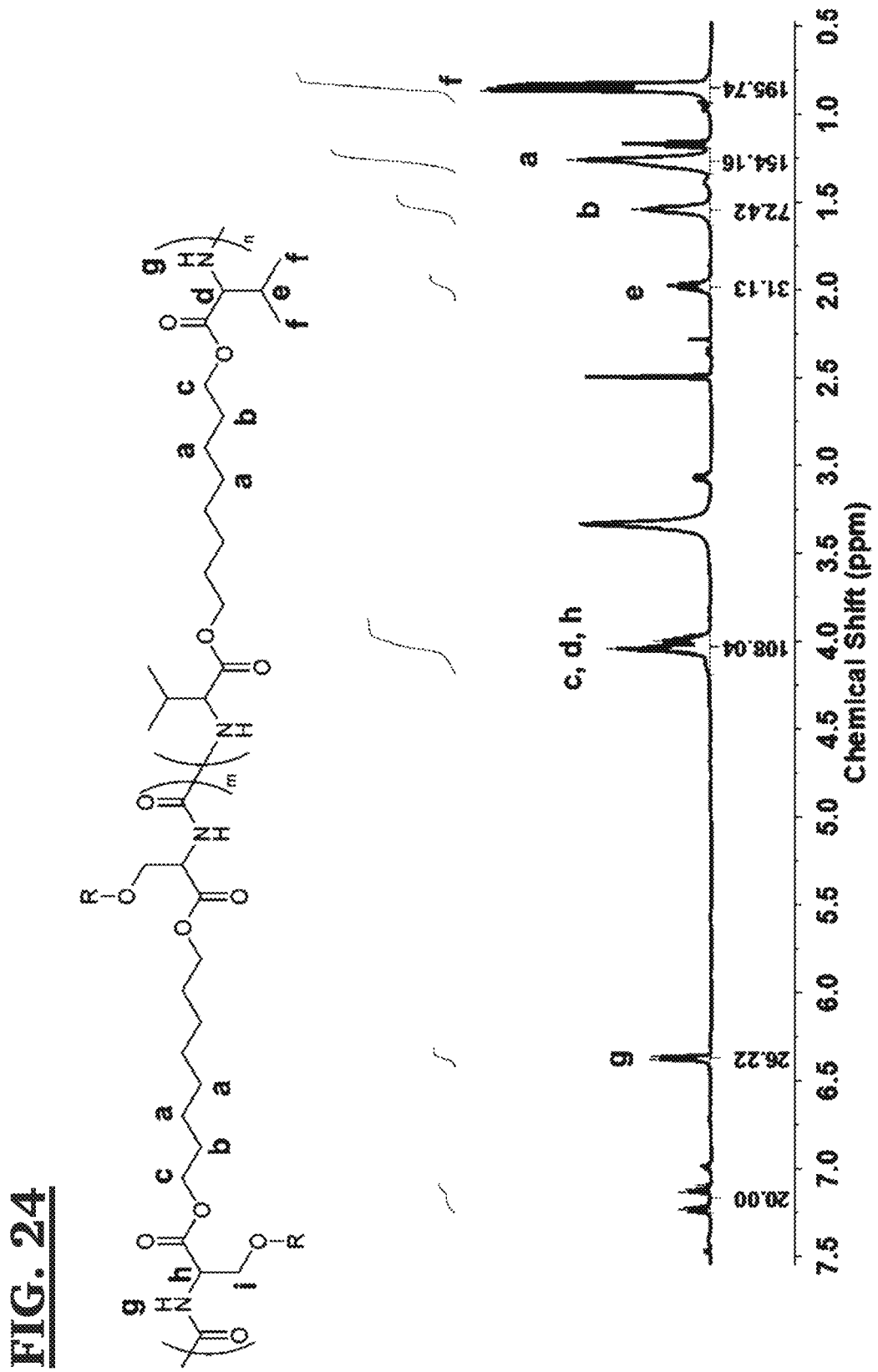

FIG. 24 is a $^1$H NMR spectra of 5% Poly(SerDPP-co-Val) (DMSO-$d_6$, 500 MHz, 30° C.).

Figure 25:
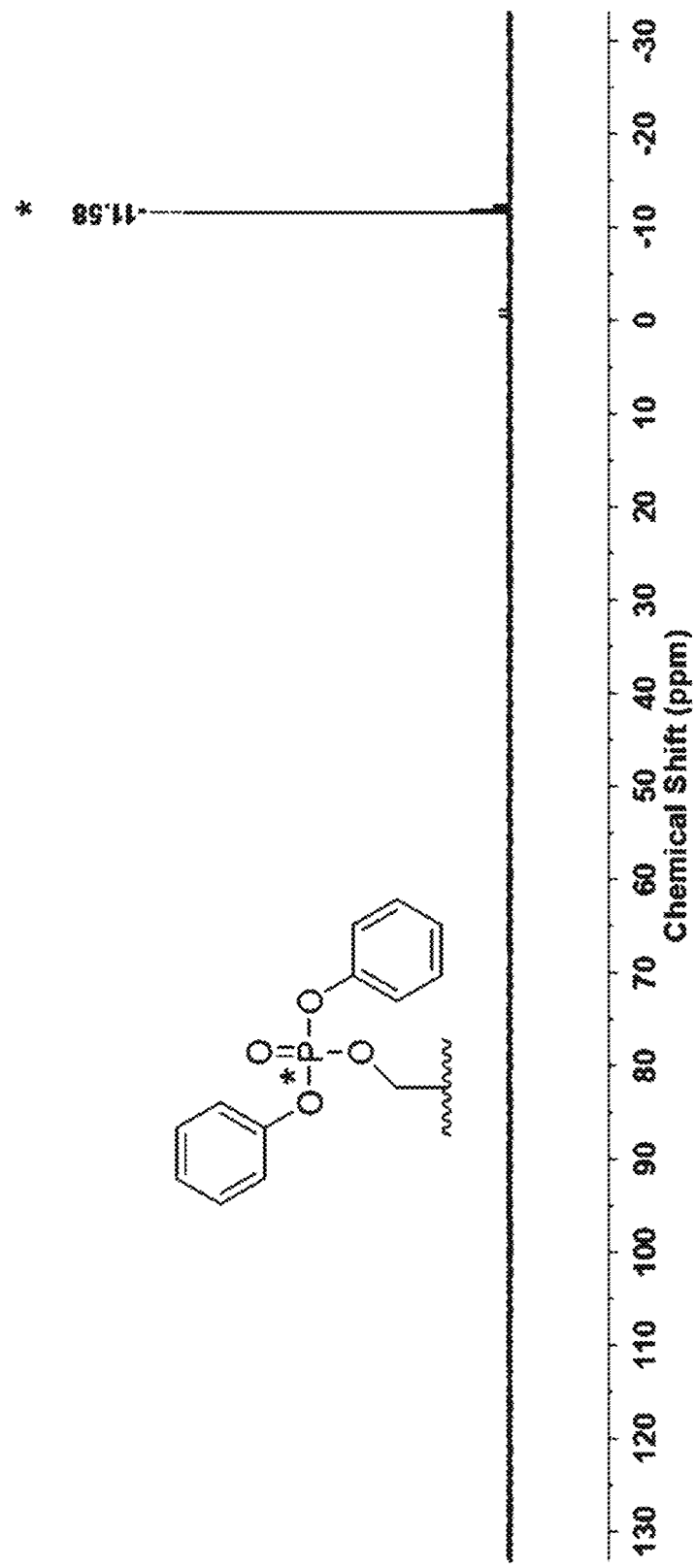

FIG. 25 is a $^{31}$P NMR spectra of 5% Poly(SerDPP-co-Val) (DMSO-$d_6$, 500 MHz, 30° C.).

Figure 26:
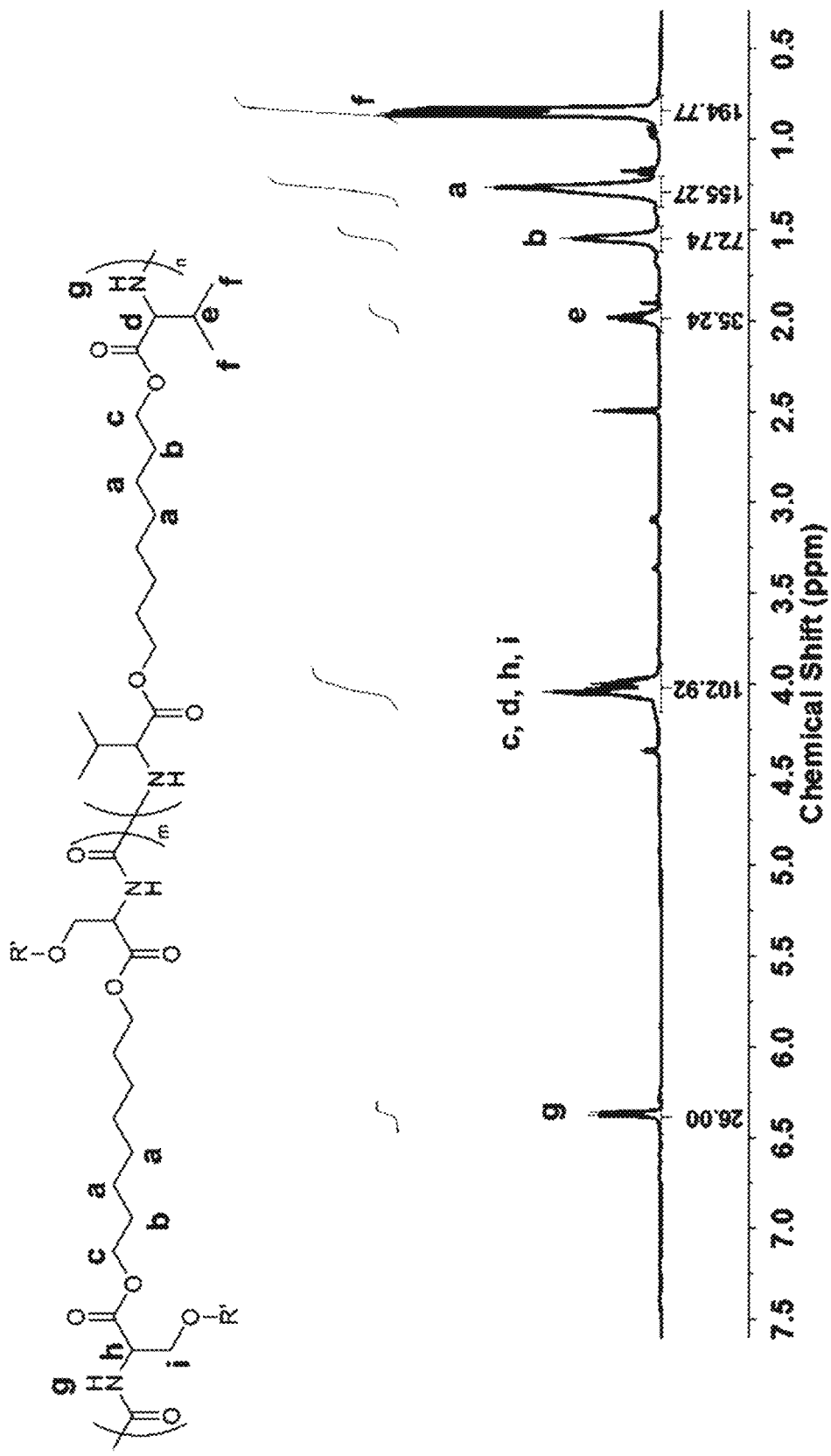

FIG. 26 is a $^1$H NMR spectra of 5% Poly(pSer-co-Val) (DMSO-$d_6$, 500 MHz, 30° C.).

Figure 27:
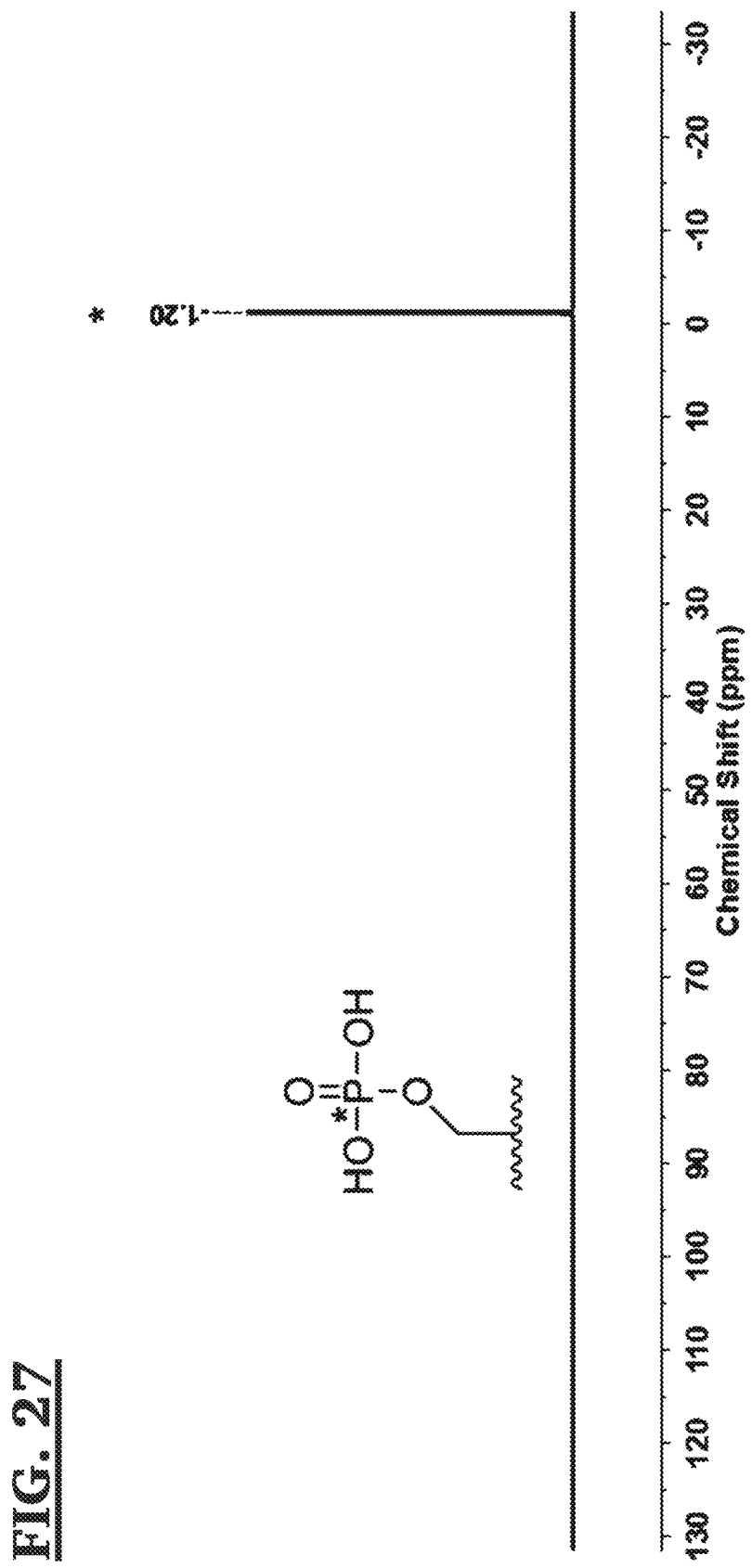

FIG. 27 is a $^{31}$P NMR spectra of 5% Poly(pSer-co-Val) (DMSO-$d_6$, 500 MHz, 30° C.).

DETAILED DESCRIPTION OF THE ILLUSTRATIVE EMBODIMENTS

In various aspects, the present invention provides a novel phosphate functionalized amino acid-based poly(ester urea) adhesive, which is strong, degradable, and resorbable, as well as related methods for its synthesis and its use. As set forth above, these adhesives are formed from phosphate functionalized, amino acid-based PEU polymers and/or copolymers that are_crosslinked using one or more divalent metal crosslinking agents. They have been found particularly effective in bonding bone to either bone or metal and have demonstrated adhesive strengths on bone samples that were significant (439±203 KPa) and comparable to commercially available poly(methyl methacrylate) bone cement (530±133 KPa). It is believed that these phosphate functionalized PEU polymers and copolymers have significant potential as orthopaedic adhesives, scaffold materials for spinal cord injury and orthopaedic repairs in the presence of growth peptides like OGP or BMP-2 and are degradable in vitro and in vivo.

In a first aspect, the present invention is directed to a phosphate functionalized amino acid-based poly(ester urea) adhesive formed from one or more amino acid-based PEU polymers and/or copolymers having phosphate functional groups, and a crosslinking agent. These amino acid-based PEU polymers and/or copolymers have a PEU polymer backbone, having one or more side chains comprising a phosphate group, and are composed of a variety or amino acid-based polyester segments, each comprising the residue of two or three amino acids separated by from about 1 to about 60 carbon atoms, and joined to each other by urea bonds.

In some embodiments, these polyester monomer segments will each contain the residue of two or more amino acids selected from alanine (ala—A), glycine (gly—G), isoleucine (ile—I), leucine (leu—L), methionine (met—M), phenylalanine (phe—F), serine (ser—S), threonine (thr—T), tryptophan (trp—W), tyrosine (tyr—Y), and valine (val—V) separated by a linear carbon chain of from 2 to about 20 carbons in length or a branched carbon chain of from about 2 to about 60 carbon atoms in length. In some embodiments, each of these polyester monomer segments may have two of the same amino acids, but in some other embodiments, some or all of these polyester monomer segments may have two different amino acids. In some of these embodiments, at least some of these polyester monomer segments will comprise the residue of one or more phosphorylated L-serine, threonine, or tyrosine molecules separated by from about 2 to about 20 carbon atoms. In some of these embodiments, these polyester monomer segments will comprise the residue of two valine or isoleucine molecules separated by from about 2 to about 20 carbon atoms.

As set forth above, in some embodiments, the amino acid residues forming the polyester monomer segments are separated by a linear carbon chain of from about 2 to about 20 carbon atoms or a branched carbon chain of from about 2 to about 60 carbon atoms. In some embodiments, the amino acid residues forming the polyester monomer segments are separated by a linear carbon chain of from about 3 to about 20 carbon atoms, in other embodiments, from about 4 to about 20 carbon atoms, in other embodiments, from about 6 to about 20 carbon atoms, in other embodiments, from about 8 to about 20 carbon atoms, in other embodiments, from about 10 to about 20 carbon atoms, in other embodiments, from about 2 to about 18 carbon atoms, in other embodiments, from about 2 to about 16 carbon atoms, in other embodiments, from about 2 to about 14 carbon atoms, in other embodiments, from about 2 to about 12 carbon atoms. In some embodiments, the amino acid residues forming the polyester monomer segments are separated by a branched carbon chain of from about 5 to about 60 carbon atoms, in other embodiments, from about 10 to about 60 carbon atoms, in other embodiments, from about 15 to about 60 carbon atoms, in other embodiments, from about 8 to about 20 carbon atoms, in other embodiments, from about 20 to about 60 carbon atoms, in other embodiments, from about 2 to about 50 carbon atoms, in other embodiments, from about 2 to about 40 carbon atoms, in other embodiments, from about 2 to about 30 carbon atoms, in other embodiments, from about 2 to about 20 carbon atoms. In some embodiments, the amino acid residues forming the polyester monomer segments are separated by 8 carbon atoms.

In one or more embodiments, some of the polyester monomer segments have the formula:

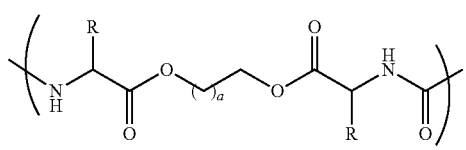

(VII)

where R is —CH$_3$, —H, —CH(CH$_3$)CH$_2$CH$_3$, —CH$_2$CH(CH$_3$)$_2$, —(CH$_2$)$_2$SCH$_3$, —CH$_2$Ph-, —CH(OH)CH$_3$, —CH$_2$—C=CH—NH-Ph, —CH$_2$-Ph-OH, —CH(CH$_3$)$_2$; and a is an integer from 1 to 20.

In one or more embodiments, some of the polyester monomer segments have the formula:

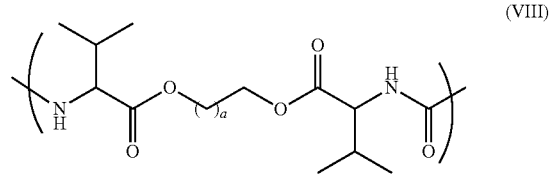

(VIII)

where a is an integer from 1 to 20. In one or more of these embodiments a is 7.

In one or more embodiments, some of the polyester monomer segments may have the formula:

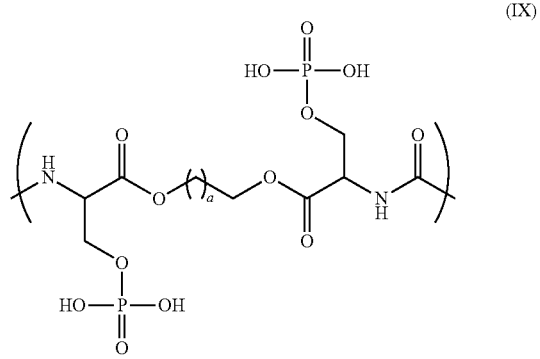

(IX)

where a is an integer from 1 to 20.

In various embodiments, from about 1 mole percent to about 30 mole percent of the polyester monomer segments forming the phosphate functionalized amino acid-based poly(ester urea) adhesive of the present invention will have at least one phosphate side chain. In some embodiments, from about 2 mole percent to about 25 mole percent, in other embodiments, from about 2 mole percent to about 20 mole percent, in other embodiments, from about 2 mole percent to about 15 mole percent, in other embodiments, from about 2 mole percent to about 12 mole percent, in other embodiments, from about 2 mole percent to about 10 mole percent of the polyester monomer segments forming the phosphate functionalized amino acid-based poly(ester urea) adhesive of the present invention will have at least one phosphate side chain.

In one or more embodiments, the phosphate functionalized amino acid-based poly(ester urea) adhesive of the present invention is a copolymer comprising one or more first amino acid based polyester monomer segments having at least one phosphate side chain and one or more second amino acid based polyester monomer segments as described above that do not have a phosphate side chain. In one or more of these embodiments, the first amino acid based polyester monomer segments of the present invention will comprise the residue of two phosphorylated L-serine molecules separated by a linear carbon chain of from about 1 to about 20 carbon atoms. In some of these embodiments, the first amino acid based polyester monomer segments of the present invention will have the formula IX, shown above.

In some of these embodiments, the second amino acid based polyester monomer segments will comprise the residue of two alanine (ala—A), glycine (gly—G), isoleucine (ile—I), leucine (leu—L), methionine (met—M), phenylalanine (phe—F), threonine (thr—T), tryptophan (trp—W), tyrosine (tyr—Y), or valine (val—V) molecules separated by a carbon chain of from 2 to about 20 carbons in length as described above. In some other of these embodiments, second amino acid based polyester monomer segments will comprise the residue of three or four of these amino acid molecules separated by a branched carbon chain of from 3 to about 60 carbons in length as described above. In various embodiments, these segments may have the formula VII or VIII, above. In some embodiments, the second amino acid based polyester monomer segments will comprise the residue of two valine or two isoleucine molecules separated by from 1 to 20 carbon atoms, as described above. In some embodiments, the second the first amino acid based polyester monomer segments will comprise the residue of two valine molecules separated by eight carbon atoms.

As will be apparent, the first and second amino acid based polyester monomer segments are connected to each other by urea bonds. It is expected that the first amino acid based polyester monomer segments will comprise from about 0.5 mole percent to about 20 mole percent of the phosphate functionalized amino acid-based poly(ester urea) copolymer. In some embodiments, the first amino acid based polyester monomer segments will comprise from about 1 mole percent to about 20 mole percent, in other embodiments, from about 2 mole percent to about 20 mole percent, in other embodiments, from about 4 mole percent to about 20 mole percent, in other embodiments, from about 1 mole percent to about 15 mole percent, in other embodiments, from about 1 mole percent to about 10 mole percent, in other embodiments, from about 2 mole percent to about 8 mole percent of the phosphate functionalized amino acid-based poly(ester urea) copolymer of the present invention.

In various embodiments, these phosphate functionalized amino acid-based poly(ester urea) copolymers will have the formula:

where R is —$CH_3$, H, —$CH(CH_3)CH_2CH_3$, —$CH_2CH(CH_3)_2$, —$(CH_2)_2SCH_3$, —$CH_2Ph$-, —$CH(OH)CH_3$, —$CH_2$—C=CH—NH-Ph, —$CH_2$-Ph-OH, —$CH(CH_3)_2$; a is an integer from 1 to 20; m is a mole percent of from about 1% to about 20%; and n is a mole percent from about 80% to about 99%.

In some these embodiments, a is an integer from 2 to 20, in other embodiments from 2 to 20, in other embodiments from 4 to 20, in other embodiments from 6 to 20, in other embodiments from 8 to 20, in other embodiments from 2 to 18, in other embodiments from 2 to 14, and in other embodiments from 2 to 10. In some these embodiments, m is a mole percent from 2% to 20%, in other embodiments, from 4 to 20, in other embodiments, from 6 to 20, in other embodiments, from 8 to 20, in other embodiments, from 2 to 16, in other embodiments, from 2 to 14, and in other embodiments, from 2 to 12. In some these embodiments, n is a mole percent from 84 to 99, in other embodiments from 88 to 99, in other embodiments, from 92 to 99, in other embodiments, from 96 to 99, in other embodiments, from 80 to 97, in other embodiments, from 80 to 93, in other embodiments, from 80 to 90, and in other embodiments, from 80 to 85.

As set forth above, phosphate functionalized amino acid-based poly(ester urea) adhesive of the present invention further comprises the residue of a divalent metal crosslinking agent. (See, FIG. 1). The term "metal" as applied herein to the crosslinking agent should be understood to include alkali earth metals like calcium and magnesium. Suitable divalent metals may include, without limitation, calcium, magnesium, strontium, barium, zinc and combinations thereof.

In various embodiments, the molar ratio of the phosphate functionalized amino acid-based poly(ester urea) polymers and/or copolymers to divalent metal ions crosslinking the adhesive is from about 1:1 to about 10:1. In some embodiments, the molar ratio of the phosphate functionalized amino

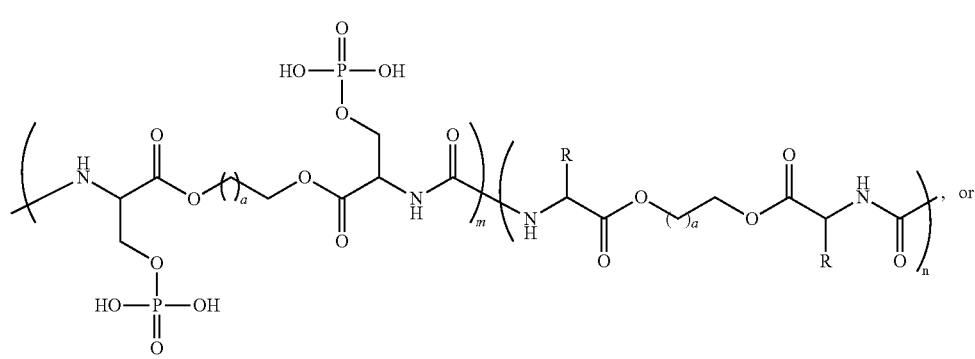

(V)

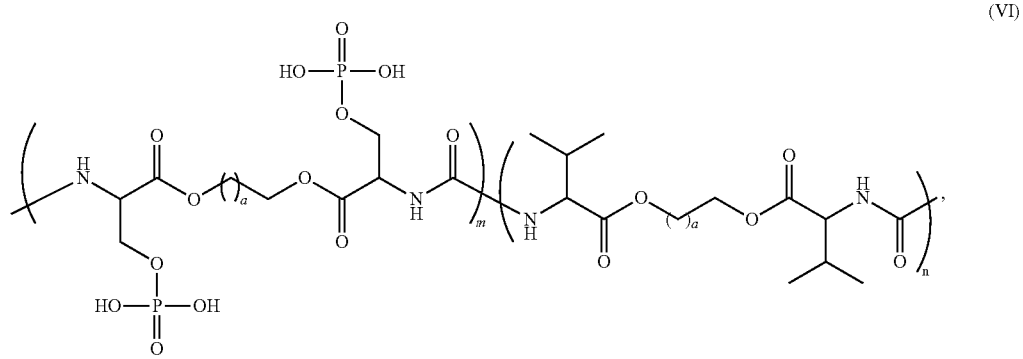

(VI)

acid-based poly(ester urea) polymers or copolymers to divalent metal ions is from about 2:1 to about 10:1, in other embodiments, from about 4:1 to about 10:1, in other embodiments, from about 6:1 to about 10:1, in other embodiments, from about 1:1 to about 8:1, in other embodiments, from about 1:1 to about 6:1, in other embodiments, from about 1:1 to about 4:1, in other embodiments, from about 2:1 to about 8:1, and in other embodiments, from about 3:1 to about 7:1.

In a second aspect, the present invention is directed to a method for making the phosphate functionalized amino acid-based poly(ester urea) adhesive described above. In general outline, the method involves forming an amino acid-based PEU polymer and/or copolymer from a variety of polyester monomers, at least some of which have phosphate side groups, and combining it with a crosslinking agent containing a divalent metal salt to form a phosphate functionalized amino acid-based poly(ester urea) adhesive.

As set forth above, some of the amino acid-based polyester monomers used to form the amino acid-based PEU polymer and/or copolymer are comprised of two alanine (ala—A), glycine (gly—G), isoleucine (ile—I), leucine (leu—L), methionine (met—M), phenylalanine (phe—F), threonine (thr—T), tryptophan (trp—W), tyrosine (tyr—Y), or valine (val—V) molecules separated by a carbon chain of from 1 to about 20 carbons in length. In some embodiments, these amino acid-based polyester monomers will have two of the same amino acids, but this is not required and embodiments having two different amino acids are possible and within the scope of the invention. In various embodiments, the amino acids forming these amino acid-based polyester monomers used to form the amino acid-based PEU polymers and/or copolymers are separated by a linear carbon chain of from about 2 to about 20 carbon atoms or a branched carbon chain of from about 2 to about 60 carbon atoms, as described above. These amino acid-based polyester monomers form part of the amino acid-based PEU polymer and/or copolymer used to form the phosphate functionalized amino acid-based poly(ester urea) adhesive described above, but do not include the adhesive phosphate side chains.

In one or more embodiments, these amino acid-based polyester monomers may comprise two valine molecules separated by from about 1 to about 20 carbon atoms. In some embodiments, these amino acid-based polyester monomers may have the formula:

(II)

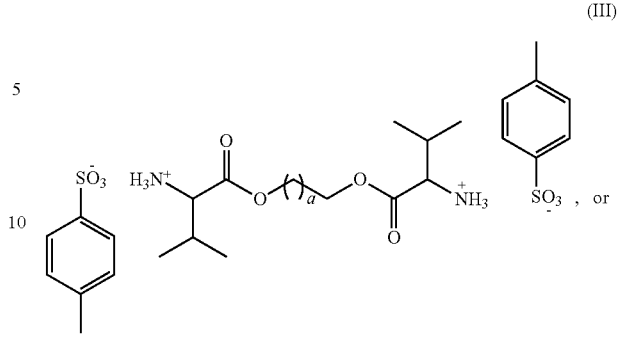

(III)

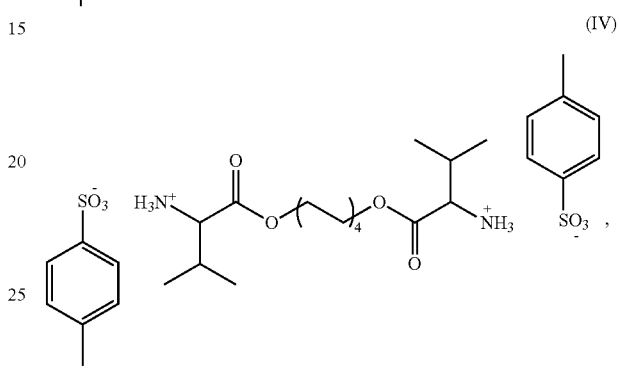

(IV)

where R is —CH$_3$, H, —CH(CH$_3$)CH$_2$CH$_3$, —CH$_2$(CH$_3$)$_2$, —(CH$_2$)$_2$SCH$_3$, —CH$_2$Ph-, —CH(OH)CH$_3$, —CH$_2$—C=CH—NH-Ph, —CH$_2$-Ph-OH, —CH(CH$_3$)$_2$ and a is an integer from 1 to 20.

In various embodiments, these amino acid-based polyester monomers may be formed from the reaction of the selected amino acids with a polyol as shown in Scheme 1.

Scheme 1

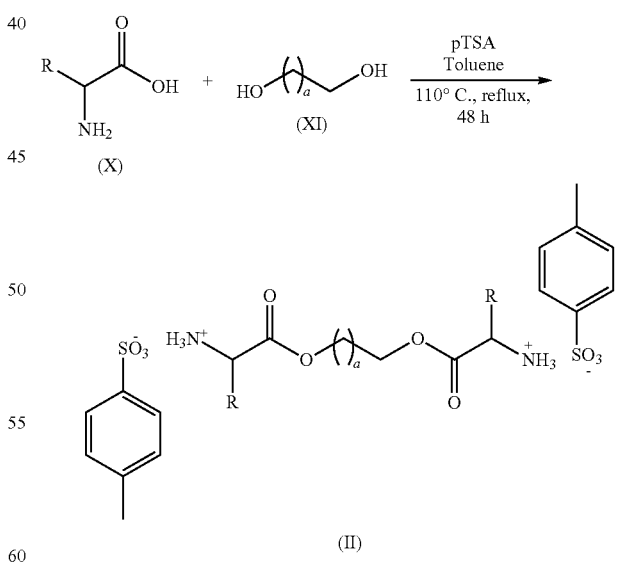

In the embodiment shown in Scheme 1, the selected amino acids are alanine, glycine, isoleucine, leucine, methionine, phenylalanine, threonine, tryptophan, tyrosine, and/or valine (R=—CH$_3$, H, —CH(CH$_3$)CH$_2$CH$_3$, —CH$_2$CH(CH$_3$)$_2$, —(CH$_2$)$_2$SCH$_3$, —CH$_2$Ph-, —CH(OH)CH$_3$, —CH$_2$—C=CH—NH-Ph, —CH$_2$-Ph-OH, or —CH (CH$_3$)$_2$) is reacted with a C$_1$-C$_{20}$ diol, but the invention is not so limited. In various embodiments, the selected amino acids may be reacted with a linear or branched polyol having from 2 to 60 carbon atoms. In various embodiments, the polyol may be a diol, triol, or tetraol. The polyol shown in Scheme 1 above is a diol having from 2 to 20 carbon atoms. In some of these embodiments, the polyol is a diol having from 2 to 17 carbon atoms, in other embodiments, from 2 to 13 carbon atoms, in other embodiments, from 2 to 10 carbon atoms, in other embodiments, from 10 to 20 carbon atoms. Suitable polyols may include, without limitation, 1,6-hexanediol, 1,8-octanediol, 1,9-nonanediol, 1,10-decanediol, 1,11-undecanediol, 1,12-dodecanediol, 1,13-tridecanediol, 1,14-tetradecanediol, 1,15-pentadecanediol, 1,16-hexadecanediol, 1,17-heptadecanediol, 1,18-octadecanediol, 1,19-nonadecanediol, 1,20-icosanediol, 2-butene-1,4-diol, 3,4-dihydroxy-1-butene, 7-octene-1,2-diol, 3-hexene-1,6-diol, 1,4-butynediol, trimethylolpropane allyl ether, 3-allyloxy-1,2-propanediol, 2,4-hexadiyne-1,6-diol, 2-hydroxymethyl-1,3-propanediol, 1,1,1-Tris(hydroxymethyl)propane, 1,1,1-tris(hydroxymethyl)ethane, pentaerythritol, di(trimethylolpropane) dipentaerythritol and combinations thereof. In the embodiments, the polyol may be 1,6-hexanediol and is commercially available from Sigma Aldrich Company LLC (St. Louis, Mo.) or Alfa Aesar (Ward Hill, Mass.).

The reaction of the polyol with the amino acid to create these amino acid-based polyester monomers can be achieved in any number of ways generally known to those of skill in the art. Generally, a condensation reaction at temperatures exceeding the boiling point of water involving a slight molar excess (~2.1 eq.) of the acid relative to the hydoxy groups is sufficient to enable the reaction to proceed.

In the reaction shown in Scheme 1, the amino acid starting material and the polyol are dissolved in a suitable solvent with a suitable acid and heated to a temperature of from 110° C. to about 114° C. and refluxed for from about 20 hours to about 48 hours to form the salt of a monomer having two or more amino acid residues separated by from about 2 to about 60 carbon atoms, depending upon the polyol used. One of ordinary skill in the art will be able to select a suitable acid without undue experimentation. In some embodiments, the acid used may be p-toluene sulfonic acid monohydrate. One of ordinary skill in the art will also be able to select a suitable solvent without undue experimentation. Suitable solvents include without limitation, toluene, dichloromethane, chloroform, dimethylformamide (DMF) or combinations thereof. In some embodiments, the solvent used is toluene.

As will be apparent to those of skill in the art, steps should be taken to protect the amine groups on the monomer intermediates to prevent transamidation. In the reaction of Scheme 1, the presence of toluene sulphonic acid (pTSA) is necessary to protonate the amine on the amino acid and ensure that trans amidation reactions do not occur at higher conversions. The invention is not limited to the method shown Scheme 1, however, and one of ordinary skill in the art will be able to select a suitable counter-ion to prevent trans amidation without undue experimentation. Materials capable of producing suitable protecting counter-ions may include without limitation, p-toluene sulfonic acid monohydrate, chlorides, bromides, acetates, trifluoroacetate, or combinations thereof.

In some embodiments, the crude product of the reaction shown in Scheme 1 may be purified using any means known in the art for that purpose. In some embodiments, the crude product is purified by first vacuum filtering the crude product to remove the residual solvent and decolorizing it in activated carbon to remove any residual salts or unreacted monomers. It is then recrystallized from boiling water or a 1:1 mixture of water and alcohol from 1 to 10 times to produce a purified product.

As set forth above, the amino acid-based PEU polymers and/or copolymers forming phosphate functionalized amino acid-based poly(ester urea) adhesives of the present invention further comprise the residues of phosphorylated amino acid-based polyester monomers. These monomers are similar in overall structure to the amino acid-based polyester monomers described above but instead of (or in addition to) containing alanine, glycine, isoleucine, leucine, methionine, phenylalanine, threonine, tryptophan, tyrosine, or valine amino acid molecules, the phosphorylated amino acid-based polyester monomers contain one or more serine, threonine, or tyrosine molecules that have been functionalized with protected phosphate groups.

In one or more embodiments, these phosphorylated amino acid-based polyester monomers may have the formula:

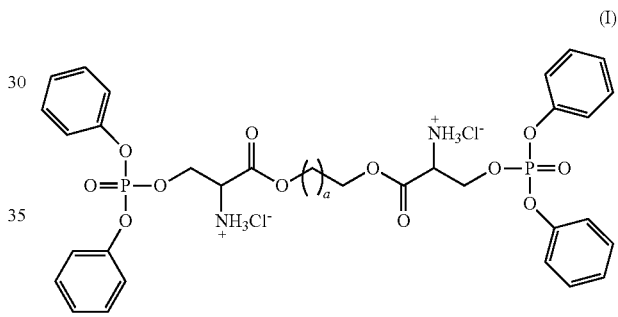

(I)

where a is an integer from about 1 to about 60, as set forth above. As with the non-phosphorylated amino acid-based monomers described above, steps should be taken to protect the amine groups on the monomer to prevent transamidation. Again, one of ordinary skill in the art will be able to select a suitable counter-ion to prevent trans amidation without undue experimentation. Materials capable of producing suitable protecting counter-ions may include without limitation, p-toluene sulfonic acid monohydrate, chlorides, bromides, acetates. trifluoroacetate, or combinations thereof.

In addition, steps should be taken to protect the OH groups on the phosphate group in order to prevent side reactions at these OH groups. One ordinary skill in the arts will know how to attached protecting groups to prevent these side reactions. In some embodiments, phenyl groups are used as protecting groups as shown in formula I, but the invention is not so limited and other suitable protecting groups may be used.

In one or more embodiment, the phosphorylated amino acid-based polyester monomers may be formed via a condensation reaction between protected serine, threonine, or tyrosine molecules and any of the polyols identified above with respect to the non-phosphorylated amino acid-based polyester monomers, followed by the addition of a protected phosphate group. In some embodiments, phosphorylated amino acid-based polyester monomers may be formed from a Boc and benzyl protected serine molecule and a C$_2$-C$_{20}$ diol as shown in Scheme 2, below.

Scheme 2

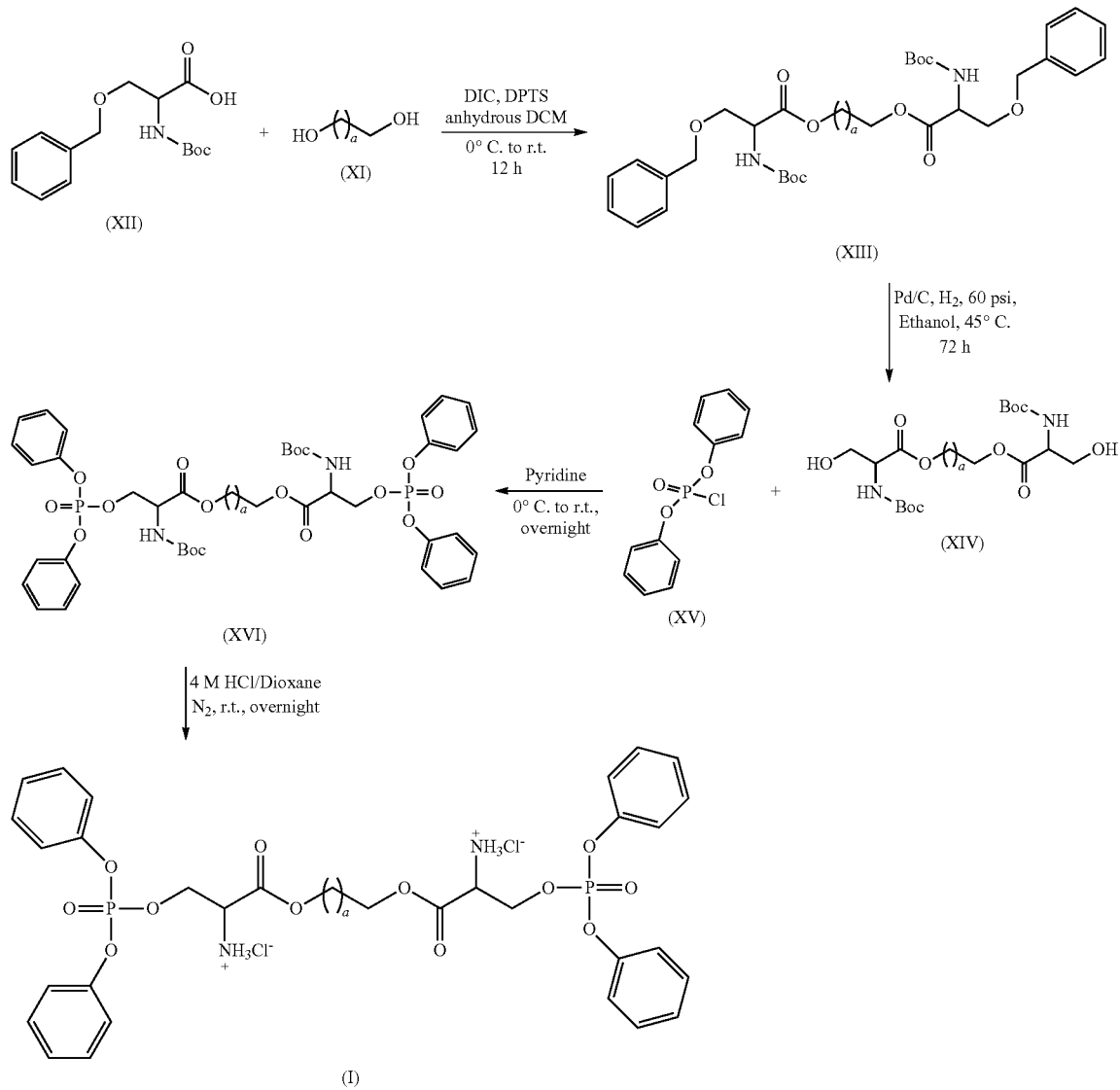

where a is an integer from 1 to 19.

In the embodiments shown in Scheme 2, the starting materials (XI), (XII) and an activating agent like pyridinium 4-toluenesulfonate (DPTS) are dissolved in a suitable solvent such as dichloromethane, chloroform, dioxane is a suitable reaction vessel under an inert atmosphere. The solution is then cooled to a temperature of from about −20° C. to about 20° C. and a coupling such as N,N'-Diisopropylcarbodiimide (DIC) is added. This reaction produces the Boc and benzyl protected serine-based polyester intermediary (XIII). In the second reaction shown in Scheme 2, this Boc and benzyl protected serine-based polyester intermediary (XIII) is dissolved in a suitable solvent, such as ethanol isopropanol protonated using a hydrogenation bottle and a palladium on carbon catalyst to form the bis-N-boc(l-serine) polyester intermediary (XIV). In a third reaction, protected phosphate groups are added to the t bis-N-boc(l-serine) polyester intermediary (XIV) by dissolving it in a suitable solvent, such as pyridine and reacting it with diphenylphosphoryl chloride (XV) to produce a bis-N-boc-O-diphenylphosphate(l-serine) polyester intermediary (XVI).

Finally, the bis-N-boc-O-diphenylphosphate(l-serine) polyester intermediary (XVI) is deprotected and protonated using an acid, such as trifluoroacetic acid or sulfuric acid to produce the corresponding phosphorylated amino acid-based polyester monomer (I).

As set forth above, the amino acid-based polyester monomers, at least some of which contain phenyl protected phosphate groups are reacted with a PEU forming compound to produce the phosphorylated amino acid-based PEU polymers and/or copolymers used in the amino acid-based PEU polymer adhesives of the present invention. As used herein, the term "PEU forming compound" refers to a compound capable of placing a carboxyl group between two amine groups, thereby forming a urea bond and includes, without limitation, triphosgene, diphosgene, or phosgene. As set forth above, diphosgene (a liquid) and triphosgene (a solid crystal) are understood to be more suitable than phosgene because they are generally appreciated as safer substitutes to phosgene, which is a toxic gas. The reaction of an amino acid-based polyester monomers with triphosgene, diphosgene or phosgene to create an amino acid-based PEU polymer or copolymer can also be achieved in any number of ways generally known to those of skill in the art.

In some embodiments, the phosphorylated amino acid-based PEU polymers and/or copolymers used in the amino acid-based PEU polymer adhesives of the present invention may be formed from phosphorylated amino acid-based polyester monomer and non-phosphorylated amino acid-based polyester monomers as shown in Scheme 3, below.

where R=—CH$_3$, H, —CH(CH$_3$)CH$_2$CH$_3$, —CH$_2$CH(CH$_3$)$_2$, —(CH$_2$)$_2$SCH$_3$, —CH$_2$Ph-, —CH(OH)CH$_3$, —CH$_2$—C=CH—NH-Ph, —CH$_2$-Ph-OH, or —CH(CH$_3$)$_2$; R' is a diphenylphosphoryl group; each a is an integer from 1 to 20; m is a mole percent of from about 1% to about 20%; and n is a mole percent from about 80% to about 99%.

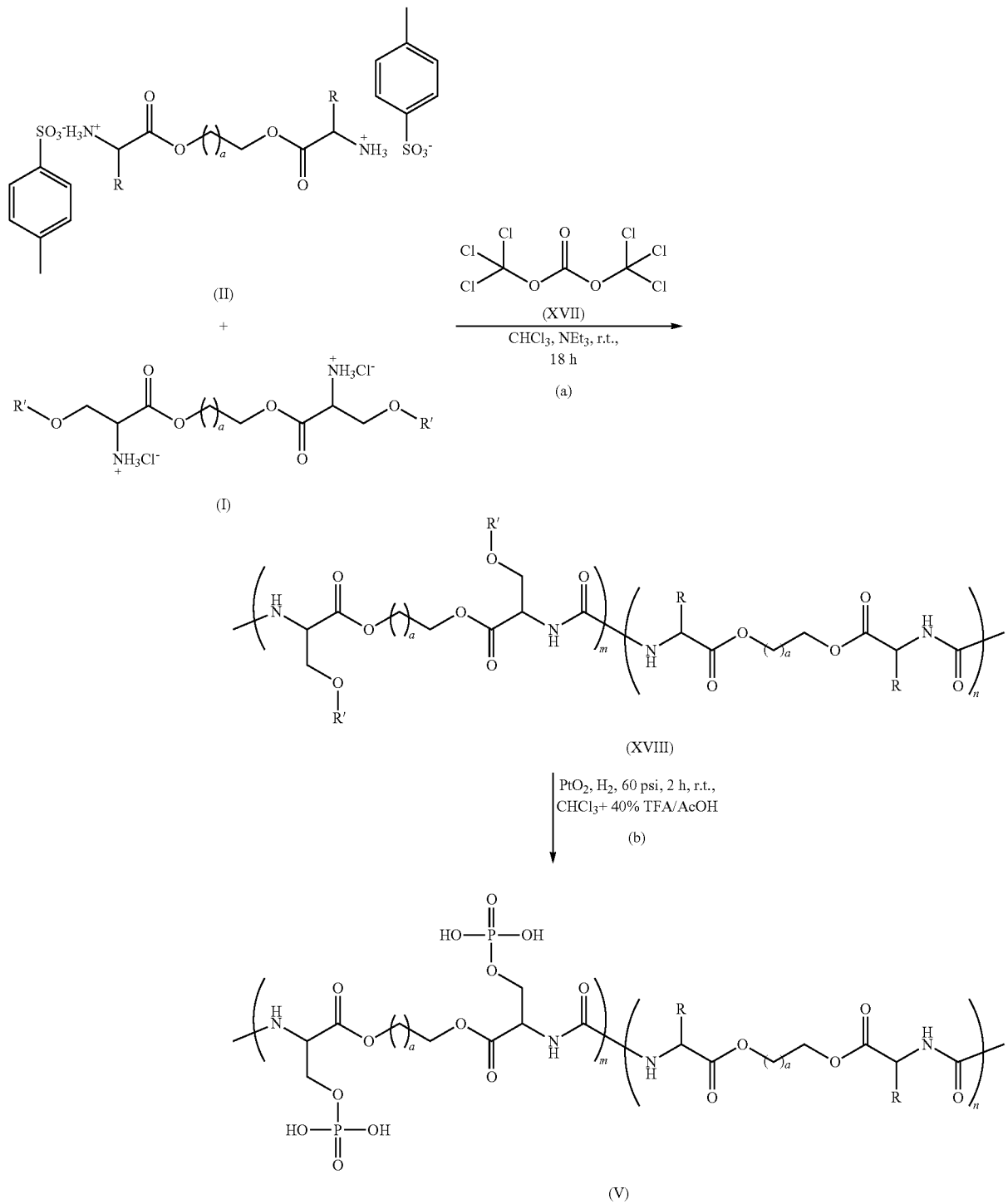

In various embodiments, the protected polyester monomers (I, II) are combined at a molar ratio of phosphorylated amino acid-based polyester monomer (II) to non-phosphorylated amino acid-based polyester monomers (I) of from about 1:99 to about 1:5, in other embodiments, from about 1:80 to about 1:70, in other embodiments, from about 1:60 to about 1:50, in other embodiments, from about 1:40 to about 1:30, in other embodiments, from about 1:20 to about 1:15, and in other embodiments, from about 1:10 to about 1:8.

In Step (a) of Scheme 3, the protected polyester monomers (I, II) are polymerized using an interfacial polymerization method to form an amino acid-based PEU copolymer having diphenylphosphoryl side groups (XVIII). As used herein interfacial polymerization refers to polymerization that takes place at or near the interfacial boundary of two immiscible fluids. In these embodiments, the protected polyester monomers (I, II) are combined in a desired molar ratio with a first fraction of a suitable organic water soluble base such as triethylamine, sodium carbonate, potassium carbonate, sodium bicarbonate, or potassium bicarbonate and dissolved in water using mechanical stirring and a warm water bath (approximately 35° C.). In one or more these embodiments, the reaction is then cooled to a temperature of from about −10° C. to about 2° C. and an additional fraction of an organic water soluble base such as sodium carbonate, potassium carbonate, sodium bicarbonate, or potassium bicarbonate is dissolved in water and then added to the reaction mixture. The reaction may be cooled by any means known in the art for that purpose, including, without limitation, ice baths, water baths, or recirculating coolers.

Next, a first fraction of a PEU forming compound such as triphosgene (XVII) diphosgene or phosgene is dissolved in a suitable solvent, such as distilled chloroform or dichloromethane, and is then added to the reaction mixture. In Step (a) of Scheme 3, the PEU forming compound is diphosgene. One of ordinary skill will be able to select a suitable solvent for the PEU forming compound without undue experimentation. After a period of from about 2 to about 60 minutes, a second fraction of the PEU forming compound (such as triphosgene, diphosgene or phosgene) is dissolved in a suitable solvent, such as distilled chloroform or dichloromethane, and added dropwise to the reaction mixture over a period of from about 0.5 to about 6 hours to produce a crude PEU copolymer containing segments having diphenylphosphoryl side groups and non-phoshphorylated PEU segments. The crude product of Step (a) of Scheme 3 may be purified using any means known in the art for that purpose. In some embodiments, the crude product of Step (a) of Scheme 3 may be purified by transferring it into a separatory funnel and precipitating it into boiling water.

In Step (b) of Scheme 3, the diphenyl protecting groups on the amino acid-based PEU copolymer having diphenylphosphoryl side groups (XVIII) are deprotected by hydrogenolysis in the presence of a metal catalyst, such as $PtO_2$ to form the phosphorylated amino acid-based PEU polymers and/or copolymers (V) used in the amino acid-based PEU polymer adhesives of the present invention. In the reaction shown in Step (b) of Scheme 3, the amino acid-based PEU copolymer having diphenylphosphoryl side groups (XVIII) was dissolved in a suitable solvent such as dichloromethane and trifluoroacetic acid (TFA)/acetic acid (AcOH). A metal catalyst, such as $PtO_2$, is then added to the polymer solution in a hydrogenation bomb reactor in the presence of $H_2$ (60 psi) to form the phosphorylated amino acid-based PEU polymers and/or copolymers (V) used in the amino acid-based PEU polymer adhesives of the present invention. The crude product of Step (b) of Scheme 3 may be purified using any means known in the art for that purpose. In some embodiments, the crude product of Step (b) of Scheme 3 may be purified by transferring it into a separatory funnel and precipitating it into boiling water. (See generally, Examples 7-12)

To form the amino acid-based PEU polymer adhesives of the present invention, the phosphorylated amino acid-based PEU polymers and/or copolymers described above must be combined with a crosslinking agent shortly before application to the surfaces to be bonded. As set forth above, suitable crosslinking agents will comprise a solution containing divalent metal ions. (See, FIG. 1). Suitable divalent metals may include, without limitation, calcium, magnesium, strontium, barium, zinc, and combinations thereof. In various embodiments, the crosslinking agent may comprise a solution containing divalent ions of calcium or magnesium.

In various embodiments, the molar ratio of the phosphate functionalized amino acid-based poly(ester urea) polymers and/or copolymers to divalent metal ions in the crosslinking agents is from about 1:1 to about 10:1. In some embodiments, the molar ratio of the phosphate functionalized amino acid-based poly(ester urea) polymers or copolymers to the divalent metal ions in the crosslinking agents is from about 2:1 to about 10:1, in other embodiments, from about 4:1 to about 10:1, in other embodiments, from about 6:1 to about 10:1, in other embodiments, from about 1:1 to about 8:1, in other embodiments, from about 1:1 to about 6:1, in other embodiments, from about 1:1 to about 4:1, in other embodiments, from about 2:1 to about 8:1, and in other embodiments, from about 3:1 to about 7:1.

In a third aspect, the present invention is directed to a method for bonding bone to bone or bone to metal using the phosphate functionalized amino acid-based poly(ester urea) adhesive described above. In these embodiments, the bone and/or metal surfaces are first cleaned and prepared using any applicable method. Next, a phosphorylated amino acid-based PEU polymer and/or copolymer is prepared as set forth above. Shortly before the surfaces are to be bonded, an amount of a crosslinking agent, as described above, is mixed into the phosphorylated amino acid-based PEU polymer and/or copolymer to begin the crosslinking reaction. The mixture is then applied to one or more of the surfaces to be bonded and the surfaces are pressed together and held in place as the polymer continues to crosslink. As the polymer fully crosslinks, the surfaces will become fully adhered to each other.

Experimental

PEU copolymers based on phosphorylated serine (pSer) and valine amino acids were synthesized and characterized for their physical properties. The pSer content incorporated in the copolymer was 2% and 5%. The solubility of these polymers in ethanol makes them more clinically relevant and show strong possibility for further development as bone adhesives. Their adhesion strengths were studied before and after crosslinking with $Ca^{2+}$ by lap shear adhesion on aluminum substrates and end-to-end adhesion on bovine bone substrates.

Scheme 4 represents the synthesis of Poly(pSer-co-Val) used for these experiments. The first step of polymer synthesis involved the solution polymerization of di-p-toluene-sulfonic acid salt of bis(L-Valine)-1,8-octanyl diester (1-Val-8) monomer and a diphenyl protected phosphoserine monomer, to produce poly(serine diphenylphosphate-co-valine) (Poly(SerDPP-co-Val)). The second step involved hydrogenolysis deprotection of poly(SerDPP-co-Val) to obtain the phosphate functionalized copolymer, poly(phosphoserine-co-valine) (poly(pSer-co-Val)).

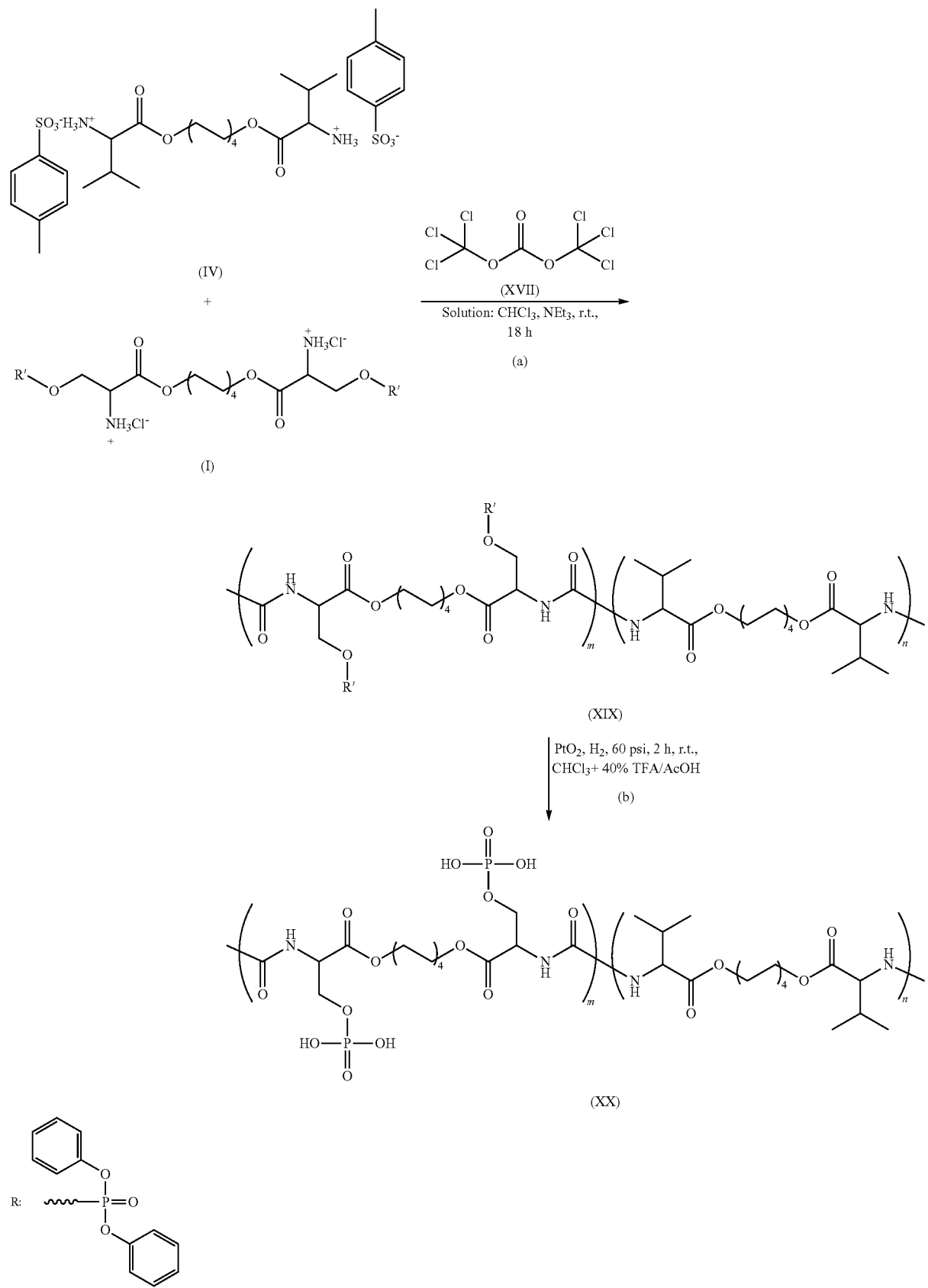

Figure 2A:
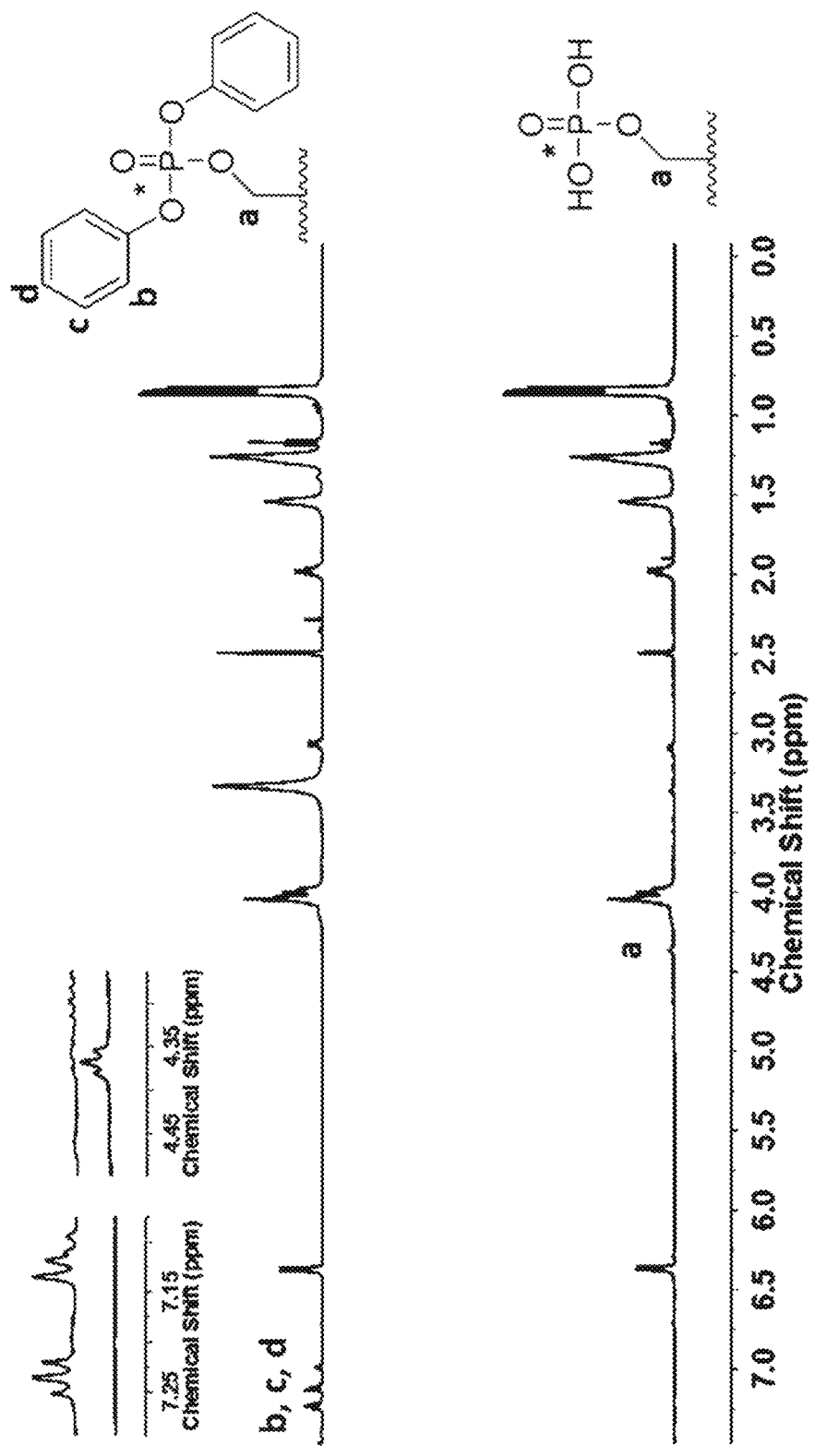
FIGS. 2A-B are charts showing $^1$H NMR spectra of 5% Poly(SerDPP-co-Val) (upper) and 5% Poly(pSer-co-Val) (lower) (FIG. 2A) and $^{31}$P NMR spectra of 5% Poly(Ser-DPP-co-Val) (upper) and 5% Poly(pSer-co-Val) (lower), referenced to 85% $H_3PO_4$ as external standard (FIG. 2B).
Figure 2B:
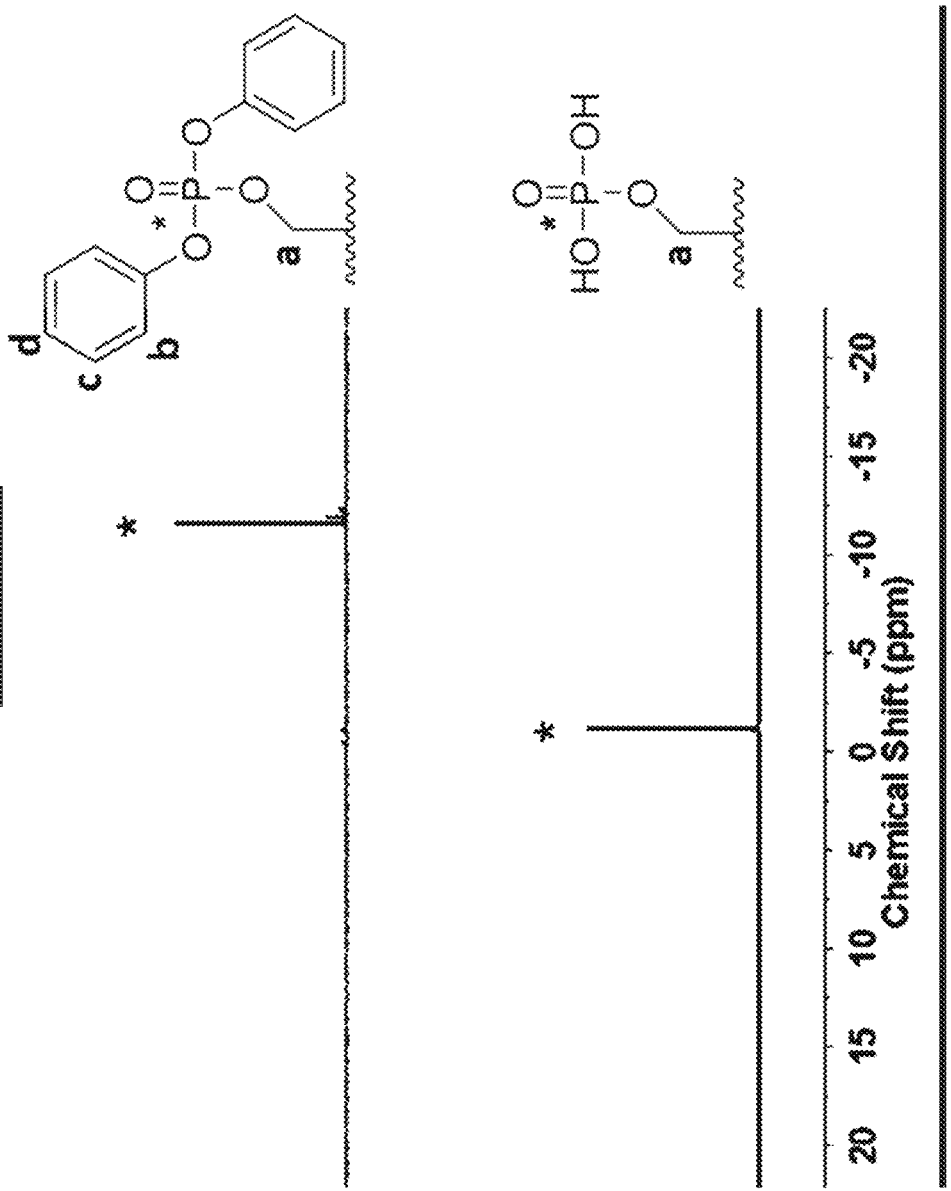

In these experiments, copolymers with 2% and 5% pSer content were synthesized and noted as 2% poly(pSer-co-Val) and 5% poly(pSer-co-Val), respectively. The actual amount of serine monomer incorporated into the polymer was found to be less than the feed amount as measured by $^1$H NMR spectroscopy. A plausible justification is the presence of four bulky phenyl groups on the monomer. This tends to lower the reactivity of the serine monomer resulting in low incorporation of serine content. From the $^1$H NMR spectra of 5% Poly(pSer-co-Val), the phenyl protecting groups show peaks in the aromatic region δ=7.06-7.34 ppm. The successful deprotection of these phenyl groups after hydrogenolysis was confirmed by the loss of aromatic peaks. The proton environments on the methylene attached directly to the protected phosphate group have a resonance around δ=4.0 ppm which shifts slightly downfield to δ=4.37 ppm after deprotection (FIG. 2A). The removal of the protecting phenyl groups was also confirmed from $^{13}$C NMR spectra. The aromatic peaks at δ=~120-130 ppm in 5% Poly(Ser-DPP-co-Val) disappear after deprotection in 5% Poly(pSer-co-Val) (FIGS. 3 and 4). $^{31}$P NMR spectra also verify complete deprotection of the phenyl groups. 5% Poly(Ser-DPP-co-Val) have a characteristic phosphorus peak at δ=−11.58 ppm which shifts to δ=−1.20 ppm after deprotection. (FIG. 2B).

The attenuated total internal reflection infrared spectroscopy (ATR-IR), show the presence and conservation of phosphate groups before and after deprotection of the diphenyl groups. The P—O—H bond has a characteristic IR peak in the range of 700-500 cm$^{-1}$ while P═O bond has a characteristic peak between 1200-1100 cm$^{-1}$. The P—O characteristic peak for Poly(SerDPP-co-Val) is seen around ~675 cm$^{-1}$ which shows a slight shift to ~710 cm$^{-1}$ after deprotection. The P═O bond shows a characteristic peak ~1040 cm$^{-1}$ before and after deprotection. None of these two characteristic phosphate stretching peaks are prominent in the 1-Val-8 polymer (Poly(1-Val-8)) (FIG. 5). The $^1$H NMR spectra for 2% copolymer resembles that of the 5% copolymer except the integration values are different (FIGS. 6 and 7). The $^{13}$C and $^{31}$P NMR spectra for the 2% copolymers also have similar δ (ppm) as that of 5% copolymers (FIGS. 8-11).

PEUs were characterized to determine their physical properties like decomposition temperature ($T_d$) by Thermogravimetric Analysis (TGA), glass transition temperature ($T_g$) by Differential Scanning Calorimetry (DSC), number average molecular weight ($M_n$), weight average molecular weight ($M_w$) and polydispersity ($Đ_M$) by SEC. Surface energies of these polymers were determined from contact angles of 5 different liquids of known surface energies to calculate the polar and dispersive components of the polymer surface energy by the following equation (see, Stakleff, K. S.; Lin, F.; Smith Callahan, L. A.; Wade, M. B.; Esterle, A.; Miller, J.; Graham, M.; Becker, M. L., Resorbable, amino acid-based poly(ester urea)s crosslinked with osteogenic growth peptide with enhanced mechanical properties and bioactivity. *Acta Biomater* 2013, 9, (2), 5132-42; and Yu, J. Y.; Lin, F.; Lin, P. P.; Gao, Y. H.; Becker, M. L., Phenylalanine-Based Poly(ester urea): Synthesis, Characterization, and in vitro Degradation. *Macromolecules* 2014, 47, (1), 121-129, the disclosures of which are incorporated herein by reference in their entirety).

$$\frac{(1 + \cos\theta_{LP})\gamma_L}{2\sqrt{\gamma_L^d}} = \sqrt{\gamma_S^d} + \sqrt{\frac{\gamma_L^p}{\gamma_L^d}} \cdot \sqrt{\gamma_S^p} \quad \text{(Equation 1)}$$

where, $\theta_{LP}$—Contact angle between polymer and the liquid; $\gamma_L$—Liquid surface tension; $\gamma_L^d$—Dispersive component of liquid surface tension; $\gamma_L^p$—Polar component of liquid surface tension; $\gamma_S^p$—Polar component of the polymer surface energy; $\gamma_S^d$—Dispersive component of polymer surface energy. The total surface energy of the polymer $\gamma_P$ (mJ m$^{-2}$) is the sum of the polar and dispersive components calculated from Equation 1. Table 1 summarizes the physical properties of the polymers. The molecular masses of the poly(pSer-co-Val) were not determined to prevent blocking of the SEC columns because of the adhesive nature of the polymer. The hydrogenolysis reaction in the presence of PtO$_2$ catalyst is highly selective and site specific so polymer degradation was not expected to occur during this reaction.

TABLE 1

Physical properties of the poly(ester urea)s

| | $T_g$ [° C.][a] | $T_d$ [° C.] | $M_n$ [KDa] | $M_w$ [KDa] | $Đ_M$[b] | Surface Energy $\gamma_P$ [mJ m$^{-2}$][c] |
|---|---|---|---|---|---|---|
| Poly(1,8-Val) | 19 | 285 | 4.3 | 13.9 | 3.2 | 29.0 ± 0.6 |
| 2% Poly(SerDPP-co-Val) | 8 | 266 | 7.7 | 10.5 | 1.4 | 32.4 ± 1.0 |
| 5% Poly(SerDPP-co-Val) | 5 | 269 | 6.5 | 9.3 | 1.4 | 37.0 ± 1.7 |
| 2% Poly(pSer-co-Val) | 2 | 175 | / | / | / | 35.8 ± 0.7 |
| 5% Poly(pSer-co-Val) | 3 | 161 | / | / | / | 33.5 ± 1.5 |

[a] $T_g$ determined by DSC;
[b] $Đ_M$ determined from SEC after purification by precipitation in water;
[c] Surface energy determined by The Owens/Wendt method from contact angle of 5 different liquids on the polymer film.

Poly(pSer-co-Val)s show slightly lower glass transition temperatures than poly(SerDPP-co-Val). The presence of the bulky phenyl groups on the protected polymer makes the chains stiff and hinders their movement while after deprotection the chains become more flexible and flow freely showing a slight drop in the respective $T_g$ (FIG. 12). Both the protected and deprotected polymers possess decomposition temperatures above 150° C. (FIG. 13). The molecular masses of all the polymers are comparable which avoids deviation in adhesion strength due to molecular mass effects. The molecular mass distribution ($Đ_m$) is slightly lower than what is expected of a step growth polymerization reaction for poly(SerDPP-co-Val) because during purification the polymer undergoes fractionation narrowing the Đ$_m$. Total surface energies of the polymers along with their polar and dispersive components are tabulated in Table 2.

TABLE 2

Polymer Surface Energies

| Components | P(1-Val-8) | 2% P(SerDPP-co-Val) | 5% P(SerDPP-co-Val) | 2% P(pSer-co-Val) | 5% P(pSer-co-Val) |
|---|---|---|---|---|---|
| $\gamma_S^p$ | 9.6 ± 0.4 | 12.6 ± 0.7 | 13.0 ± 1.2 | 21.2 ± 0.5 | 19.4 ± 1.0 |
| $\gamma_S^d$ | 19.4 ± 0.4 | 19.8 ± 0.7 | 24.0 ± 1.2 | 14.6 ± 0.5 | 14.1 ± 1.1 |
| $\gamma_P$ | 29.0 ± 0.6 | 32.4 ± 1.0 | 37.0 ± 1.7 | 35.8 ± 0.7 | 33.5 ± 1.5 |

Both the 2% and 5% Poly(pSer-co-Val) have polar and dispersive components for surface energy. The presence of polar component is indicative of surface polar groups that play a significant role in surface adhesion. The surface energies of the 2% and 5% polymers are comparable with each other and are higher than Poly(1-Val-8). Since the percentage of functional groups on the polymers was small we did not see an appreciable change in surface energies between the 2% and 5% functionalization.

Lap Shear Adhesion Test on Aluminum Substrate

Lap shear adhesion is a common method used to determine the strength of adhesive materials and their mode of failure. (See, Example 14) Adhesive strength of the polymer was studied under lap shear configuration at room temperature on aluminum adherends. Lap shear adhesion test was performed on 2% and 5% Poly(pSer-co-Val) with and without crosslinking with $Ca^{2+}$. Poly(1-Val-8) was used as one of the controls to prove the significance of phosphate groups in adhesion. Commercially available PMMA bone cement was used as another control for comparison with Poly(pSer-co-Val). The results of lap shear adhesion test are summarized in FIG. 14A.

Figure 1:
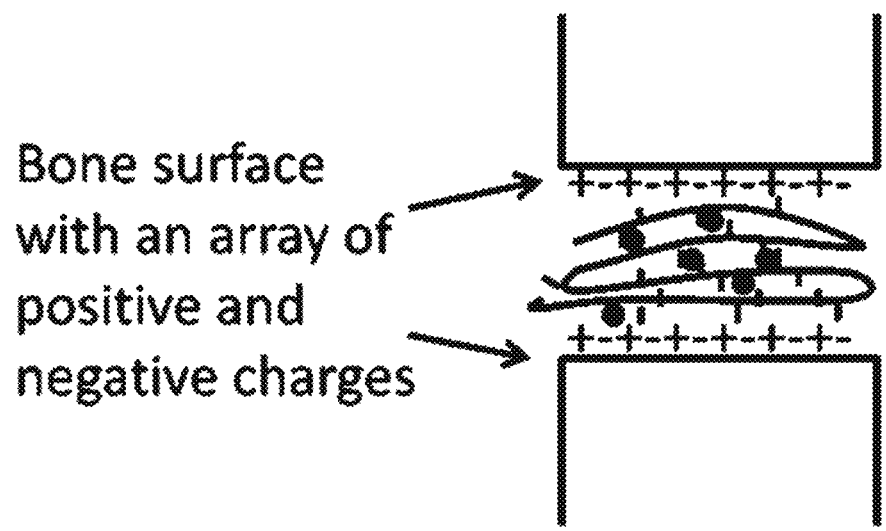
FIG. 1 is a schematic diagram showing how phosphate groups ( ) on Poly(pSer-co-Val) interact with positive charges on the bone surface promoting adhesion to the bone. $Ca^{2+}$ from calcium iodide (cross-linking agent) interact with phosphate groups in the bulk of the polymer giving rise to cohesive forces.
Figure 1:
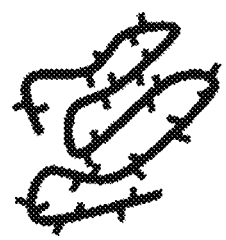

The adhesion strength of poly(1-Val-8) was 0.04±0.16 MPa and the PMMA bone cement was 0.04±0.01 MPa. The low adhesion strength for bone cement is expected because poly(methyl methacrylate) does not have adhesive properties. PMMA bone cements have high modulus and are essentially used as fillers for bone and teeth. Poly(pSer-co-Val) show improved adhesion strength compared to the control samples which could arise from electrostatic or hydrogen bonding interactions between the phosphate groups and the aluminum surface. The adhesion strengths of 2% and 5% poly(pSer-co-Val) are 0.92±0.18 MPa and 0.77±0.09 MPa respectively (FIG. 14A). Previous studies on caddisfly silk have shown that crosslinking with $Ca^{2+}$ impart strength to the fiber and the crystalline β-sheet structure collapses if the divalent cations are removed suggesting the significance of $Ca^{2+}$ in the system. (See, Addison, J. B.; Ashton, N. N.; Weber, W. S.; Stewart, R. J.; Holland, G. P.; Yarger, J. L., beta-Sheet nanocrystalline domains formed from phosphorylated serine-rich motifs in caddisfly larval silk: a solid state NMR and XRD study. *Biomacromolecules* 2013, 14, (4), 1140-8; Addison, J. B.; Weber, W. S.; Mou, Q.; Ashton, N. N.; Stewart, R. J.; Holland, G. P.; Yarger, J. L., Reversible assembly of beta-sheet nanocrystals within caddisfly silk. *Biomacromolecules* 2014, 15, (4), 1269-75, the disclosure of which are incorporated herein by reference in their entirety. Our hypothesis is that phosphate groups on the polymer backbone chain will interact with $Ca^{2+}$ in the crosslinking agent resulting in physical crosslinking which will improve cohesive forces within the polymer bulk further increasing the adhesive strength compared to their uncrosslinked counterparts (FIG. 1). Adhesion strength is the result of combined effects of both adhesive and cohesive forces within a system. To test our hypothesis we chose calcium iodide as the source of $Ca^{2+}$ for our system.

Both 2% and 5% $Ca^{2+}$ crosslinked poly(pSer-co-Val) showed an increase in the adhesion strengths compared to their uncrosslinked counterparts. The adhesion strengths of crosslinked 2% poly(pSer-co-Val) and crosslinked 5% poly (pSer-co-Val) are 1.17±0.19 MPa and 1.14±0.02 MPa respectively (FIG. 14A). Our results demonstrate the strong affinity of the phosphate functionalized polymers on the aluminum substrates. Cohesive failure is when the adhesive is stuck on both the adherends after failure. If the adhesive cleanly detaches from one adherend and sticks to the other after failure, it is called adhesive failure. The mode of failure is important in determining the commercial potential of an adhesive. For most adhesives, cohesive failure is desirable. Interestingly, all the samples exhibit cohesive failure except the bone cement which failed adhesively (FIGS. 14B-G). This result is not surprising considering the fact that bone cements are not adhesive in nature but only serve as a support medium for the bone. The results of the adhesion studies on metal suggests that incorporation of even small percentage of phosphate groups on the polymer backbone show significant improvement in the adhesion strength on metal substrate. Also, crosslinking of the phosphate groups with divalent cations further enhances the adhesion strength via electrostatic interaction.

End-to-End Adhesion Test on Bovine Bone

The adhesion strengths of poly(pSer-co-Val) on bovine bone samples were also tested to demonstrate its potential application as a bone adhesive. (See, Example 15) Bones have an array of positive and negative charges on the surface. The basic building block of bone is hydroxyapatite with the chemical structure of $Ca_5(PO_4)_3(OH)$. FIG. 15A summarizes the adhesion strengths of the polymers on bovine bone. The controls for this study were the same as that for the metal substrate. Poly(1-Val-8) had absolutely no adhesion to the bone surface. All the samples failed before performing the tests. Poly(pSer-co-Val) show increased adhesion strengths compared to Poly(1-Val-8) control. 2% Poly(pSer-co-Val) showed adhesion strength of 190±70 KPa and 5% Poly(pSer-co-Val) showed adhesion strength of 399±101 KPa.

An increase in adhesion strength was observed after adding 0.3 eq. of $Ca^{2+}$ as crosslinking agent. The adhesion strength of crosslinked 2% Poly(pSer-co-Val) increased to 211±77 KPa while that of crosslinked 5% Poly(pSer-co-Val) increased to 439±203 KPa. The increase in adhesion strength of the phosphate functionalized polymer compared to that of the control polymer proves the significance of the presence of phosphate groups. It is also notable that incorporation of a small percentage of phosphate functionality brings an appreciable change in adhesion. The adhesion strength of 5% poly(pSer-co-Val) is comparable to commercially available bone cement (530±133 KPa) which suggests that poly(pSer-co-Val) has strong potential for further development into bone adhesives. All the samples showed cohesive failure except for the bone cement which showed adhesive failure.

In Vitro Cell Viability and Spreading Assay

The cell viability of MC3T3 cells was calculated using at least 40 images for each sample and normalized to 2%

Poly(pSer-co-Val). (See, Examples 16 and 17) The viability of cells on glass, poly(1-Val-8), 2% and 5% poly(pSer-co-Val), 2% and 5% crosslinked poly(pSer-co-Val) was (84±9)%, (94±8)%, (100±3)%, (97±5)%, (97±7)% and (98±4)% respectively (See, FIG. 16). The low cell viability on glass could be attributed to handling and seeding errors. High cell viabilities (>95%) on the functionalized polymers prove that the phosphate functionality is non-toxic to the cells. The cytoskeletal structure or spreading behavior of MC3T3 cells on all samples was similar. The cells were stained blue (DAPI) for nuclei, green (Alexa Fluor 488) for focal adhesion points and rhodamine phalloidin (red) for actin filaments. The aspect ratio of the cells on all samples were fairly close (~2-3), which proves that the functionalized polymers behaved similar to the controls (FIG. 17).

Phosphate functionalized PEU copolymers were designed and created to mimic the properties of caddisfly adhesive silk. These copolymers are ethanol soluble which provides a suitable delivery mechanism and makes them suitable for medical applications. The copolymers showed maximum adhesion strength of 1.17±0.19 MPa on metal substrates after crosslinking with $Ca^{2+}$. The adhesive strengths of copolymers on bone samples were significant (439±203 KPa) and comparable to commercially available poly(methyl methacrylate) bone cement (530±133 KPa). The phosphate functionalized copolymers demonstrated improved and significant adhesion strength compared to the valine polymer analogs demonstrating that the phosphate groups play a key role in promoting adhesion. In all cases the copolymers showed cohesive failure. The phosphate functionalized copolymers have significant potential as orthopaedic adhesives, scaffold materials for spinal cord injury and orthopaedic repairs in the presence of growth peptides like OGP or BMP-2. PEUs are degradable in vitro and in vivo.

EXAMPLES

The following examples are offered to more fully illustrate the invention, but are not to be construed as limiting the scope thereof. Further, while some of examples may include conclusions about the way the invention may function, the inventor do not intend to be bound by those conclusions, but put them forth only as possible explanations. Moreover, unless noted by use of past tense, presentation of an example does not imply that an experiment or procedure was, or was not, conducted, or that results were, or were not actually obtained. Efforts have been made to ensure accuracy with respect to numbers used (e.g., amounts, temperature), but some experimental errors and deviations may be present. Unless indicated otherwise, parts are parts by weight, molecular weight is weight average molecular weight, temperature is in degrees Centigrade, and pressure is at or near atmospheric.

Materials and Methods

L-valine, p-toluene sulfonic acid monohydrate, toluene, 1,8-octanediol, anhydrous dichloromethane (DCM), Pd/C, $PtO_2$, ethanol, diphenylphosphoryl chloride (99%), anhydrous pyridine, 4M HCl/Dioxane solution, chloroform, trimethylamine and acetic acid were purchased from Sigma Aldrich. N-Boc-O-Bzl-L-Serine was purchased from Ark Pharm, Inc. N,N-Diisopropyl carbodiimide (DIC) was purchased from Oakwood Chemicals. Triphosgene was purchased from TCI America. 4-(dimethyl amino) pyridinium 4-toluenesulfonate (DPTS) was synthesized according to literature procedure. Chloroform was dried over $CaH_2$ overnight, distilled and stored in dark before use. All chemicals were used as received unless noted otherwise.

$^1H$, $^{13}C$ and $^{31}P$ NMR spectra of monomers and polymers were recorded on a Varian NMR Spectrophotometer (300 MHz and 500 MHz respectively). Chemical shifts (δ) were reported in ppm and referenced to residual solvent resonances ($^1H$ NMR, DMSO-$d_6$: δ=2.50 ppm and $^{13}C$ NMR, DMSO-$d_6$: δ=39.50 ppm). Abbreviations of multiplicities are denoted as s—singlet, d—doublet, m—multiplet, q—quartet, dd—double doublet, td—triple doublet. Attenuated Total Internal Reflection Infrared (ATR-IR) Spectra of polymers were recorded on Shimadzu Miracle 10 ATR-FTIR equipped with a quartz crystal window. A small piece of polymer, enough to cover the crystal window was used for the measurements. Electrospray Ionization Mass spectrum (ESI-MS) of monomer was recorded on Bruker HCTultra II quadrupole ion trap (QIT) mass spectrometer (Billerica, Mass.) equipped with an ESI source. Molecular weights and PDI ($Đ_M$) of the polymers were determined by Size exclusion chromatography on TOSOH ECOSEC HLC-8320GPC using DMF (0.1 M LiBr salt solution) as eluent at a flow rate of 0.5 mL/min at 50° C. equipped with a refractive index detector. The glass transition temperature ($T_g$) of polymers was determined by Differential Scanning Calorimetry (DSC, TA Q200) at a scanning rate of 10° C./min for 5 cycles from −50° C. to 60° C. The decomposition temperatures of polymers ($T_d$) were determined using Thermogravimetric Analysis (TGA, TA Q500) at a heating rate of 10° C./min from 25° C. to 600° C.

Example 1

Synthesis of di-p-toluenesulfonic acid salt of bis(l-Valine)-1,8-octanyl diester (M1)

L-Valine (27.5 gm, 0.234 mol), 1,8-Octanediol (15 gm, 0.102 mol), p-toluenesulfonic acid monohydrate (46.57 gm, 0.190 mol) were weighed in a 500 ml round bottom flask along with toluene equipped with a dean stark trap, condenser and a magnetic stir bar. The solution was heated to reflux for 48 h under stirring. After the product cooled down to ambient temperature it was dissolved in hot water and stirred with carbon black to remove any colored impurities. The monomer was further subjected to 3 recrystallizations in water to yield 40 gm (yield=65%) of white powder as pure product. $^1H$ NMR (300 MHz, DMSO-d6, δ): 0.95 (dd, J=6.96 Hz, 10.48 Hz, 12H; $CH_3$), 1.21 (d, J=45.71 Hz, 8H; $CH_2$), 1.54 (m, 4H, $CH_2$), 2.02-2.20 (m, 2H, CH), 2.31 (d, J=19.91 Hz, 6H; $CH_3$), 3.90 (d, J=4.56 Hz, 2H; CH), 3.98-4.40 (m, J=6.53 Hz, 10.83 Hz, 17.18 Hz, 4H; $CH_2$), 7.29 (dd, J=7.97 Hz, 110.42 Hz, 4H; CH), 8.23 (br s, 6H, NH). See FIG. 18.

Example 2

Synthesis of bis-N-boc-O-benzyl(l-serine)-1,8-octanyl diester (M2)

N-boc-O-benzyl-l-serine (15 gm, 50.79 mmol), 1,8-octanediol (3.09 gm, 21.16 mmol) and DPTS (1.06 gm, 4.23 mmol) were dissolved in 30 ml of anhydrous DCM under $N_2$. The reaction flask was then immersed in an ice bath and DIC (7.62 ml, 48.67 mmol) was quickly injected into the flask under $N_2$ at 0° C. The reaction was left stirring overnight under inert atmosphere while the temperature gradually increased to room temperature. The reaction solution was filtered to remove the urea crystals and concentrated under vacuum. The oily product was dissolved in CHCl$_3$ and washed with 5% HCl solution twice and once with DI water, dried over anhydrous Na$_2$SO$_4$, filtered and concentrated in vacuo. A light yellow colored oil (13.38 gm, yield=89%) was obtained by silica gel column chromatography with hexane/ethyl acetate (2.65/1, v/v) as eluents. $^1$H NMR (300 MHz, DMSO-d6, δ): 1.20 (s, 4H, CH$_2$), 1.37 (s, 22H, CH$_3$), 1.50 (m, 4H, CH$_2$), 3.53-3.77 (m, 4H, CH$_2$), 3.85-4.13 (m, 4H, CH$_2$), 4.24 (dd, J=5.55 Hz, 12.80 Hz, 2H; CH), 4.46 (s, 4H, CH$_2$), 7.09 (d, J=7.92 Hz, 2H; CH), 7.19-7.40 (m, 12H, Ar H). See FIG. 19.

Example 3

Synthesis of bis-N-boc(l-serine)-1,8-octanyl diester (M3)

M2 (11 gm, 15.69 mmol) was dissolved in 30 ml of ethanol in a hydrogenation bottle. 1.3 gm of Pd/C catalyst was added to the polymer solution and subjected to hydrogenolysis under 60 psi H$_2$ pressure with slight heating (~35° C.) for 48 h. The solution was centrifuged at 5000 rpm for 30 min. The supernatant was filtered, concentrated and dried under vacuum to obtain colorless oil as product (8.5 gm, yield=77%). $^1$H NMR (300 MHz, DMSO-d6, δ): 1.20 (s, 4H, CH$_2$), 1.37 (s, 22H, CH$_3$), 1.53 (m, 4H, CH$_2$), 3.65 (t, J=5.44 Hz, 4; CH$_2$), 3.8-4.19 (m, 4H, CH$_2$), 6.91 (d, J=8.02 Hz, 2H; CH). See, FIG. 19.

Example 4

Synthesis of bis-N-boc-O-diphenylphosphate(l-serine)-1,8-octanyl diester (M4)

M3 (9 gm, 3.40 mmol) was dissolved in about 15 ml of pyridine under nitrogen and immersed in an ice bath for 15 min. Diphenylphosphoryl chloride (10.21 gm, 8 ml, 6.72 mmol) was slowly added to the reaction solution under nitrogen. The reaction was stirred overnight while the reaction temperature gradually increases to room temperature. About 30 ml of CHCl$_3$ was added to the reaction flask to dissolve the product. The solution was washed once with 100 ml of DI water, 100 ml of 1M HCl and finally 2×100 ml of DI water. The organic phase was dried over anhydrous Na$_2$SO$_4$ and further dried under vacuum until a yellowish solid product was obtained. The yellow solid was subsequently recrystallized 3 times in isopropanol to obtain white powder as pure product (8.8 gm, yield=52%). $^1$H NMR (300 MHz; DMSO-d6, δ): 1.17 (s, 4H, CH$_2$), 1.35 (s, 22H, CH$_3$), 1.47 (m, 4H, CH$_2$), 3.99 (t, J=6.36 Hz, 6H; CH$_2$), 4.42 (d, J=6.11 Hz, 4H; CH$_2$), 7.23 (dd, J=7.61 Hz, 15 Hz, 8H; Ar H), 7.4 (t, J=7.85 Hz, 12H; Ar H). See, FIG. 19.

Example 5

Synthesis of dihydrochloride salt of bis-O-diphenylphosphate(l-serine)-1,8-octanyl diester (M5)

4M HCl/Dioxane solution (40 ml) was added to M4 (8.8 gm) and stirred overnight under nitrogen. The solution was concentrated and freeze dried to remove solvent. The light yellow solid obtained after freeze drying was washed with ethyl acetate and dried to get light yellow powder as pure product (8.8 gm, yield=100%). $^1$H NMR (300 MHz, DMSO-d6, δ): 1.16 (t, J=7.05 Hz, 4H; CH$_2$), 1.43 (m, 4H, CH$_2$), 4.02 (t, J=6.20 Hz, 4H; CH$_2$), 4.68 (s, 6H, CH$_2$), 7.24 (dd, J=7.94 Hz, 15.66 Hz, 8H, Ar H), 7.41 (t, J=7.29 Hz, 12H; Ar H), 8.96 (br s, 6H, NH). See FIGS. 19 and 20. ESI-MS (m/z): Theoretical: 784.74; Calculated: [M+H]+=785.2. See, FIG. 21.

Example 6

Synthesis of 1,8-octanediol-l-valine poly(ester urea) (Poly(1-Val-8))

A solution polymerization was carried out by dissolving the di-p-toluenesulfonic acid salt of bis(L-Valine)-1,8-Octanyl-diester (M1) (13.74 g, 20 mmol, 1 eq.) and triethylamine (12.55 ml, 90 mmol, 4.5 eq.) in 40 mL of chloroform in a 500 mL three neck round bottom flask equipped with a magnetic stir bar and a pressure equalizing addition funnel. Triphosgene (2.37 g, 8 mmol, 0.4 eq.) was then dissolved in 15 mL of freshly distilled chloroform and added dropwise under nitrogen at room temperature. The reaction continued for 12 h after which an additional aliquot of triphosgene (0.45 g, 1.5 mmol, 0.08 eq.) dissolved in 15 mL of chloroform was added to the flask dropwise. The reaction was stirred for an additional 8 h. The polymer was purified by precipitation in hot water and dried under vacuum. $^1$H NMR (500 MHz, DMSO-d$_6$, δ): 0.86 (m, 12H, CH$_3$), 1.26 (s, 8H, CH$_2$), 1.54 (s, 4H, CH$_2$), 1.98 (dd, J=6.69 Hz, 11.73 Hz, 2H; CH), 3.78-4.21 (m, 6H, CH$_2$, CH), 6.37 (d, J=8.89 Hz, 2H; NH). 13.9 KDa. See, FIG. 22. $^{13}$C NMR (500 MHz, DMSO-d$_6$, δ): 19.39 (C4), 25.69 (C2), 28.55 (C2), 28.97 (C2), 30.91 (C2), 58.13 (C2), 64.52 (C2), 157.96 (NH—C=O), 172.84 (O—C=O). ATR-IR (v): 1650-1690 cm$^{-1}$ (s, C=O urea stretch), 1735-1750 cm$^{-1}$ (s, C=O ester stretch), 3300-3500 cm$^{-1}$ (m, N—H urea stretch). Đ$_M$=3.2, M$_n$=4.3 KDa, M$_w$=13.9 KDa. See, FIG. 23.

Example 7

Synthesis of Poly(serine diphenylphosphate-co-valine) (Poly(SerDPP-co-Val)

The copolymer was synthesized via a solution polymerization similar to P(1-Val-8). Typically, both the monomers (20 mmol, 1 eq.) and triethylamine (90 mmol, 4.5 eq.) were dissolved in 40 mL of freshly distilled CHCl$_3$ under N$_2$ in a 500 mL three neck round bottom flask equipped with a magnetic stirrer. Triphosgene (8 mmol, 0.4 eq.) was dissolved in 15 mL of distilled chloroform and added dropwise to the flask under nitrogen at room temperature. The reaction continued for 12 h and then additional aliquot of triphosgene (1.5 mmol, 0.075 eq in 10 mL of chloroform) was added dropwise to the flask. The reaction continued for another 8 h after which the reaction solution was transferred to a separatory funnel and precipitated dropwise in hot water. After the water cools to ambient temperature, the polymer was washed in water at room temperature overnight and finally dried under vacuum to obtain white polymer as product.

Example 8

Synthesis of 5% Poly(SerDPP-co-Val)

Theoretical monomer feed ratio—pSer/Val (M5/M1)=15/85: $^1$H NMR (500 MHz, DMSO-d$_6$, δ): Actual Monomer ratio=5/95, δ=0.85 (dd, J=6.76 Hz, 13.63 Hz, 195H; CH$_3$), 1.26 (d, J=11.12 Hz, 154H; CH$_2$), 1.54 (m, 72H, CH$_2$), 1.98

(dd, J=6.56 Hz, 12.58 Hz, 31H; CH), 3.93-4.14 (m, 137H, CH$_2$, CH), 6.37 (d, J=8.91 Hz, 38H; NH), 7.06-7.18 (m, 26H, Ar H), 7.19-7.34 (m, 12H, Ar H). $^{13}$C NMR (500 MHz, DMSO-d$_6$, δ): 19.4 (C4), 25.69 (C4), 28.55 (C4), 30.90 (C2), 58.15 (C4), 64.53 (C4), 120.34 (Ar C), 123.08 (Ar C), 129.31 (Ar C), 157.97 (NH—C═O), 172.85 (O—C═O). See, FIG. 24. $^{31}$P NMR (500 MHz, DMSO-d$_6$, 85% H$_3$PO$_4$ external reference, δ): 11.58 ppm. ATR-IR (v): 1650-1690 cm$^{-1}$ (s, C═O urea stretch), 1735-1750 cm$^{-1}$ (s, C═O ester stretch), 3300-3500 cm$^{-1}$ (m, N—H urea stretch), ~4040 cm$^{-1}$ (w, P═O stretch), ~675 cm$^{-1}$ (w, P—O stretch). Đ$_M$=1.4, M$_n$=7.7 KDa, M$_w$=10.5 KDa. See FIG. 25.

Example 9

Synthesis of 2% Poly(SerDPP-co-Val)

Theoretical monomer feed ratio—pSer/Val (M5/M1)=10/90: $^1$H NMR spectra resonances are similar to 5% P(SerDPP-co-Val) with different integration values. See FIGS. 6, 24. Actual Monomer ratio=2/98. $^{13}$C and $^{31}$P NMR spectra and ATR-IR spectra corresponds with that of 5% Poly(SerDPP-co-Val). Đ$_M$=1.4, M$_n$=6.5 KDa, M$_w$=9.3 KDa. See FIGS. 3, 6, 8, and 24.

Example 10

Synthesis of Poly(phospho serine-co-valine) (Poly(pSer-co-Val)

The diphenyl protecting groups were deprotected by hydrogenolysis in the presence of PtO$_2$ catalyst to synthesize phosphate functionalized copolymers as mimics of caddisfly silk. Typically, Poly(SerDPP-co-Val) (1.00 g) was dissolved in 50 mL CHCl$_3$: 40% TFA/AcOH (4:1) solution. PtO$_2$ (1.1 eq of SerDPP) as a catalyst was added to the polymer solution in a hydrogenation bomb reactor and the reaction was carried out in the presence of H$_2$ (60 psi) at room temperature for 2 h. The solution was filtered and concentrated under vacuum. The pure polymer was obtained as white solid after precipitation in hot water and dried under vacuum.

Example 11

5% Poly(pSer-co-Val)

0.9 g, yield=90%. $^1$H NMR (500 MHz, DMSO-d$_6$, δ): 0.85 (dd, J=6.76 Hz, 13.61 Hz, 194H; CH$_3$), 1.26 (s, 155H, CH$_2$), 1.54 (m, 72H, CH$_2$), 1.98 (td, J=6.72 Hz, 13.39 Hz, 35H; CH), 3.87-4.18 (m, 102H, CH$_2$, CH), 4.37 (t, J=6.48 Hz, 2H; CH$_2$), 6.37 (d, J=8.91 Hz, 26H, NH). $^{13}$C NMR (500 MHz, DMSO-d$_6$, δ): 19.4 (C4), 25.69 (C4), 28.55 (C4), 30.90 (C2), 58.15 (C4), 64.53 (C4), 157.97 (NH—C═O), 172.85 (O—C═O). See, FIG. 26. $^{31}$P NMR (500 MHz, DMSO-d$_6$, 85% H$_3$PO$_4$ external reference, δ): −1.20 ppm. See, FIG. 27. ATR-IR (v): 1650-1690 cm$^{-1}$ (s, C═O urea stretch), 1735-1750 cm$^{-1}$ (s, C═O ester stretch), 3300-3500 cm$^{-1}$ (m, N—H urea stretch), ~1040 cm$^{-1}$ (w, P═O stretch), ~710 cm$^{-1}$ (w, P—O stretch). See, FIG. 5.

Example 12

2% Poly(pSer-co-Val)

1 g, yield=100%. $^1$H NMR spectra resonances are similar to 5% Poly(pSer-co-Val) with different integration values. $^{13}$C and $^{31}$P NMR spectra and ATR-IR spectra corresponds with that of 5% Poly(pSer-co-Val). See FIGS. 4, 7, 9, and 26.

Example 13

Surface Energy Measurements

The contact angles of five different liquids were measured to calculate the respective surface energy for each of the polymers using the Owens/Wendt method. Liquids of known surface tension (water, glycerol, ethylene glycol, propylene glycol, and formamide) were used for the contact angle measurements. Polymer thin films were spin coated on ozone treated silicon wafers using 1% (w/v) solution of the polymers in ethanol at 2000 rpm for 1 min. The samples were dried at 70° C. under vacuum overnight. Measurements (n=3) were performed at room temperature for each sample and the standard deviation of the mean was calculated from independent measurements. The results are reported on Table 1 and 2, above.

Example 14

Lap Shear Adhesion Test on Aluminum Substrate

Lap shear adhesion tests were performed on aluminum substrates according to ASTM D1002 standard. Aluminum adherends 1.6 mm in thickness were cut into rectangular substrates 75 mm long×12.5 mm wide with a 6.5 mm diameter hole drilled 12.5 mm from one end into each adherend. For adhesion tests polymer solution in ethanol (30 μL, 300 mg in 1 mL ethanol) was applied to one end of the adherend. Another adherend was placed over it in a lap shear configuration with an overlap area of 1.56 cm$^2$. When crosslinkers were utilized, polymer solution (25 μL, 300 mg in 1 mL ethanol) and crosslinker solution (5 μL, 0.3 eq. per pSer group in 1 mL acetone) were mixed and applied to one end of the adherend. The adherends were pressed together and allowed to cure for 1 h at room temperature and 24 h at 75° C. and 1 h at room temperature before testing. Lap shear adhesion was performed using an Instron 5567 instrument with a load cell of 1000 N. The adherends were pulled apart at a speed of 1.3 mm/min until failure occurred. The adhesion strength (Pa) is obtained by dividing the maximum load at failure (N) by the area of adhesion (m$^2$). The results are reported in FIGS. 14A-G.

Example 15

End-to-End Adhesion Test on Bovine Bone Substrate

To study the adhesion characteristics of the Poly(pSer-co-Val) we performed end-to-end adhesion experiments on cortical bovine bone. Bovine bone samples were obtained from a local grocery store. The bones were cut into rectangular pieces of 2 cm long×0.6 cm width×0.4 cm thick on a bone saw. Subsequently, the test ends of the bone samples were sanded using a 320 grit sandpaper (3M Pro Grade Precision, X-fine) and the bones were kept in PBS solution 1 h prior to adhesive application. The polymer solution (30 μL, 300 mg in 1 mL ethanol) was applied on one end of bone and the second bone placed end-to-end over it. For crosslinked specimens, polymer solution (25 μL, 300 mg in 1 mL ethanol) and crosslinker solution (5 μL, 0.3 eq. per pSer group in 1 mL acetone) was applied to one bone and the second bone was placed in an end-to-end configuration. The bone samples were clipped together and wrapped in PBS soaked gauze for 24 h. The samples were then placed in an incubator at 37° C., 95% humidity and 5% $CO_2$ for 2 h before adhesion tests. Adhesion tests were performed on a Texture Analyzer (TA.XT.Plus) equipped with a 5 kg load cell. Bone samples were pulled apart at a speed of 1.3 mm/min until failure occurred. The adhesion strength (Pa) is obtained by dividing the maximum load at failure (N) by the area of adhesion ($m^2$). The results are reported in FIGS. 15A-C.

Example 16

In Vitro Cell Viability Study

Cell viability and spreading of MC3T3 cells was studied on the phosphate functionalized polymers at day 1 and day 3 respectively after seeding. Polymer films were spun coat from a 3% (w/v) solution in ethanol at 2000 rpm for 1 min on a 12 mm glass coverslips. The films were dried overnight at 80° C. under vacuum and carefully transferred to 12 well plates. Cells were rinsed with PBS prior to detaching with 1 mL of 0.05% trypsin/EDTA solution at 37° C., 95% humidity, 5% $CO_2$ for 5 mins. The trypsin/EDTA solution was deactivated by adding 5 mL of media and cells were collected by centrifugation at 4° C., 3000 rpm for 1 min. The media/trypsin solution was aspirated without disturbing the cell pellet and cells were resuspended in 5 mL fresh media. The cell density was counted using hemocytometer with trypan blue staining. The cells were seeded at a density of 6000 cells/$cm^2$. The well plates were mildly agitated to ensure even distribution of cells over the samples before incubation.

Cell viability was assessed by Live/Dead assay (Life Technologies). About 5 µL of Calcein AM (4 mM) and 10 µL of ethidium homodimer were added to 10 mL of DPBS to prepare the staining solution. Media was aspirated from all samples and rinsed with DPBS prior to adding 0.5 mL of staining solution to each well. The well plates were covered in aluminum foil and incubated at 37° C. for 10 mins before imaging. Images were taken on an Olympus fluorescence microscope equipped with a Hamamatsu orca R2CCD camera, FITC and TRITC filters at 4× magnification using CellSENS software. Cells stained green were considered live and the cells stained red were considered dead. Cells were counted in ImageJ software using cell counter plugin. The results are reported in FIG. 16.

Example 17

Cell Spreading Assay

For the spreading studies, cells were prefixed in a 1 mL media and 1 mL 3.7% paraformaldehyde (PFA) in CS buffer solution for 5 min at 37° C. on a dry block. After aspiration, the cells were fixed in 2 mL 3.7% PFA solution in CS buffer for 5 min at 37° C. The samples were then rinsed 3 times with 2 mL CS buffer followed by addition of 1.5 mL of Triton X-100 in CS buffer (0.5% v/v) in each well to permeabilize the cells for 10 mins at 37° C. The samples were rinsed 3 times with CS buffer. 2 mL of freshly prepared 0.1 wt % $NaBH_4$ in CS buffer was then added to each well for 10 min and room temperature to quench the aldehyde fluorescence, followed by aspiration and incubation in 5% donkey serum for 20 min at room temperature to block the non-specific binding. After aspiration the samples were incubated in 300 µL vinculin primary antibody Mouse in CS buffer (v/v 1:200) at 4° C. overnight. The samples were then rinsed 3 times with 1% donkey serum and stained with 50 µL rhodamine phalloidin (v/v 1:40) and Alexa Fluor 488 secondary antibody Mouse (v/v 1:200) solution on wax paper for 1 h at room temperature in dark. After washing the samples 3 times with CS buffer, the nuclei were stained using DAPI in CS buffer (6 µL/10 mL) for 20 min at room temperature in dark. The samples were rinsed 3 times with CS buffer to remove excess staining and viewed under Olympus fluorescence microscope equipped with a Hamamatsu orca R2CCD camera with FITC, TRITC and DAPI filters at 20× magnification. The results are reported in FIG. 17.

In light of the foregoing, it should be appreciated that the present invention significantly advances the art by providing a novel degradable and resorbable phosphorylated poly (ester-urea) (PEU) based adhesive (and related methods of making and using same) that is structurally and functionally improved in a number of ways. While particular embodiments of the invention have been disclosed in detail herein, it should be appreciated that the invention is not limited thereto or thereby inasmuch as variations on the invention herein will be readily appreciated by those of ordinary skill in the art. The scope of the invention shall be appreciated from the claims that follow.

What is claimed is:

1. A poly(ester urea) (PEU) based adhesive comprising:
   a PEU polymer backbone having one or more side chains comprising a phosphate group, wherein said phosphate group is covalently bonded to said one or more side chains through at least one carbon atom; and
   a crosslinking agent comprising a divalent metal salt.

2. The PEU based adhesive of claim 1 wherein said PEU polymer backbone comprises the residue of an amino acid selected from the group consisting of alanine (ala—A), glycine (gly—G), isoleucine (ile—I), leucine (leu—L), methionine (met—M), phenylalanine (phe—F), threonine (thr—T), tryptophan (trp—W), tyrosine (tyr—Y), or valine (val—V).

3. The PEU based adhesive of claim 1 wherein said PEU polymer backbone comprises the residue of one or more phosphorylated L-serine molecules.

4. The PEU based adhesive of claim 1 wherein said PEU polymer backbone having one or more side chains comprising a phosphate group further comprises:
   a residue of a first amino acid based polyester monomer comprising two phosphorylated amino acids separated by from 2 to 20 carbon atoms; and
   a residue of a second amino acid based polyester monomer comprising two amino acids separated by from 2 to 20 carbon atoms.

5. The PEU based adhesive of claim 4 wherein said first amino acid based polyester monomer comprises two phosphorylated L-serine molecules.

6. The PEU based adhesive of claim 4 wherein said first amino acid based polyester monomer has the formula:

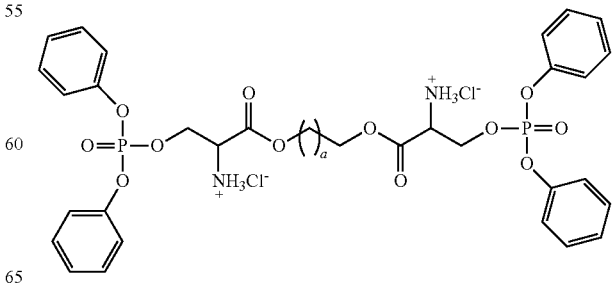

where a is an integer from about 1 to about 20.

7. The PEU based adhesive of claim 4 wherein said second amino acid based polyester monomer comprises two amino acids selected from the group consisting of alanine (ala—A), glycine (gly—G), isoleucine (ile—I), leucine (leu—L), methionine (met—M), phenylalanine (phe—F), threonine (thr—T), tryptophan (trp—W), tyrosine (tyr—Y), or valine (val—V).

8. The PEU based adhesive of claim 4 wherein said second amino acid based polyester monomer comprises valine or isoleucine.

9. The PEU based adhesive of claim 4 wherein said second amino acid based polyester monomer has the formula:

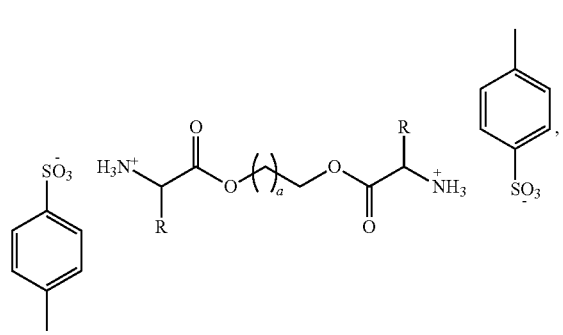

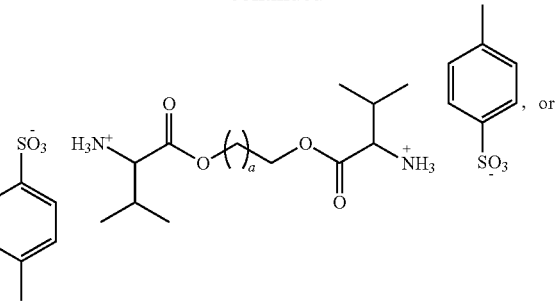

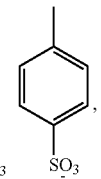

where R is —CH₃, H, —CH(CH₃)CH₂CH₃, —CH₂CH(CH₃)₂, —(CH₂)₂SCH₃, —CH₂Ph-, —CH(OH)CH₃, —CH₂—C=CH—NH-Ph, —CH₂-Ph-OH, —CH(CH₃)₂ and a is an integer from 1 to 20.

10. The PEU based adhesive of claim 1 having the formula:

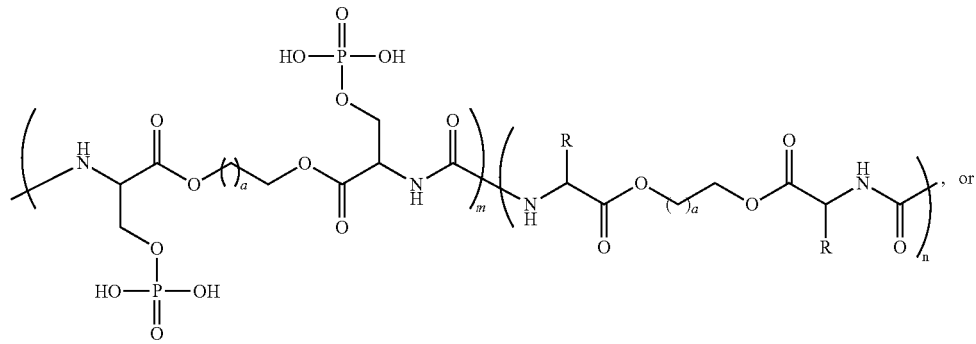

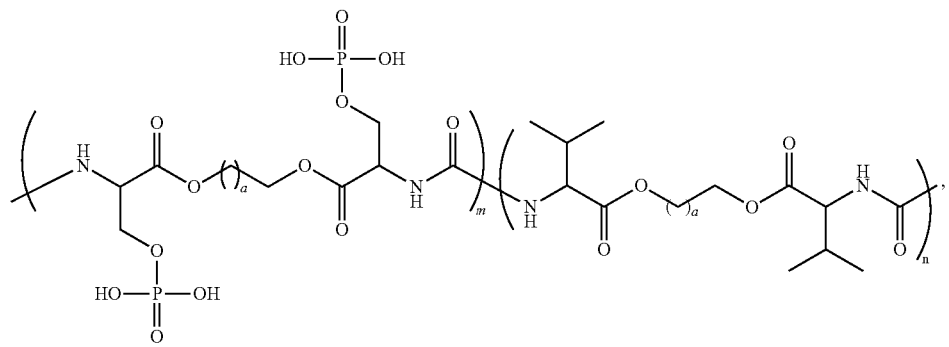

where R is —CH₃, H, —CH(CH₃)CH₂CH₃, —CH₂CH(CH₃)₂, —(CH₂)₂SCH₃, —CH₂Ph-, —CH(OH)CH₃, —CH₂—C=CH—NH-Ph, —CH₂-Ph-OH, —CH(CH₃)₂; a is an integer from 1 to 20; m is a mole percent of from about 1% to about 20%; and n is a mole percent from about 80% to about 99%.

11. The PEU based adhesive of claim 1 wherein said crosslinking agent is a divalent salt of a metal selected from the group consisting of calcium, magnesium, strontium, barium, zinc, and combinations thereof.

12. The PEU based adhesive of claim 1 wherein said crosslinking agent comprises from about 1 mole percent to about 20 mole percent of said PEU based adhesive.

13. A method of making the poly(ester urea) (PEU) based adhesive of claim 1 comprising:
A. preparing a PEU polymer having one or more side chains comprising a phosphate group, wherein said phosphate group is covalently bonded to said one or more side chains through at least one carbon atom;
B. adding a crosslinking agent comprising a divalent metal salt.

14. The method of claim 13 wherein molar ratio of said PEU polymer having one or more side chains comprising a phosphate group to said crosslinking agent comprising a divalent metal salt is from about 1:1 to about 10:1.

15. The method of claim 13 wherein said PEU polymer having one or more side chains comprising a phosphate group has the formula:

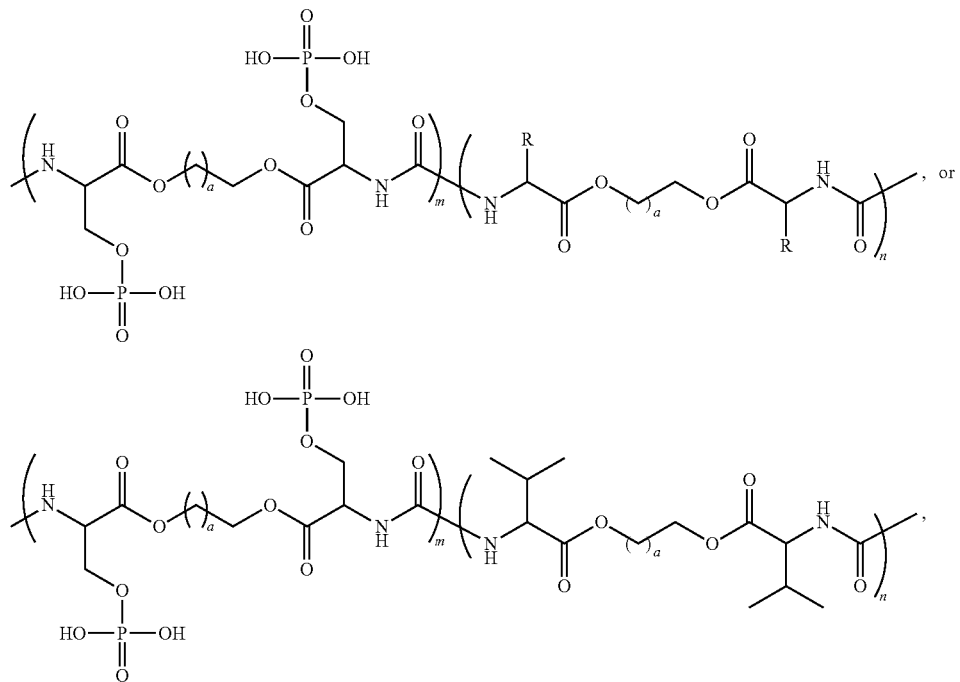

where R is —CH$_3$, H, —CH(CH$_3$)CH$_2$CH$_3$, —CH$_2$CH(CH$_3$)$_2$, —(CH$_2$)$_2$SCH$_3$, —CH$_2$Ph-, —CH(OH)CH$_3$, —CH$_2$—C=CH—NH-Ph, —CH$_2$-Ph-OH, —CH(CH$_3$)$_2$; a is an integer from 1 to 20; m is a mole percent of from about 1% to about 20%; and n is a mole percent from about 80% to about 99%.

16. The method of claim 13 wherein the step of preparing a PEU polymer (step A) further comprises:
1. preparing a first amino acid based polyester monomer comprising two phosphorylated amino acids separated by from 1 to 20 carbon atoms;
2. preparing a second amino acid based polyester monomer comprising two amino acids separated by from 2 to 20 carbon atoms;
3. reacting said first amino acid based polyester monomer and said second amino acid based polyester monomer with phosgene, diphosgene or triphosgene to introduce urea bonds between and among said first and second amino acid based polyester monomer to form the PEU polymer of step A.

17. The method of claim 16 wherein the said first amino acid based polyester monomer comprises two phosphorylated serine molecules separated by from 2 to 20 carbon atoms.

18. The method of claim 16 wherein the said second amino acid based polyester monomer comprises two amino acids selected from the group consisting of alanine (ala—A), glycine (gly—G), isoleucine (ile—I), leucine (leu—L), methionine (met—M), phenylalanine (phe—F), threonine (thr—T), tryptophan (trp—W), tyrosine (tyr—Y), or valine (val—V), separated by from 2 to 20 carbon atoms.

19. The method of claim 16 wherein the said second amino acid based polyester monomer comprises valine or isoleucine molecules.

20. A method of bonding bone to bone or bone to metal using the poly(ester urea) (PEU) based adhesive of claim 1 comprising:

A. preparing a first surface and second surface to be joined;

B. preparing a PEU polymer having one or more side chains comprising a phosphate group, wherein said phosphate group is covalently bonded to said one or more side chains through at least one carbon atom;

C. mixing a crosslinking agent comprising a divalent metal salt into the PEU polymer of step B to form the poly(ester urea) (PEU) based adhesive of claim 1;

D. applying the PEU polymer/crosslinking agent mixture of step C to one or both of said first and second surfaces to be joined;

E. placing said first and said second surfaces to be joined in contact with each other; and F. allowing the poly(ester urea) (PEU) based adhesive of claim 1 to crosslink, forming a bond between said first surface and said second surface.

\* \* \* \* \*